United States Patent
Brammer

(10) Patent No.: US 10,220,259 B2
(45) Date of Patent: *Mar. 5, 2019

(54) SYSTEM AND METHOD FOR CONTROLLING AN EXERCISE DEVICE

(71) Applicant: ICON Health & Fitness, Inc., Logan, UT (US)

(72) Inventor: Chase Brammer, Providence, UT (US)

(73) Assignee: ICON Health & Fitness, Inc., Logan, UT (US)

( * ) Notice: Subject to any disclaimer, the term of this patent is extended or adjusted under 35 U.S.C. 154(b) by 40 days.

This patent is subject to a terminal disclaimer.

(21) Appl. No.: 15/157,061

(22) Filed: May 17, 2016

(65) Prior Publication Data
US 2016/0256745 A1 Sep. 8, 2016

Related U.S. Application Data

(63) Continuation of application No. 13/734,970, filed on Jan. 5, 2013, now Pat. No. 9,339,691.
(Continued)

(51) Int. Cl.
A63B 24/00 (2006.01)
A63B 71/06 (2006.01)
(Continued)

(52) U.S. Cl.
CPC .......... *A63B 24/0087* (2013.01); *A63B 22/02* (2013.01); *A63B 22/04* (2013.01);
(Continued)

(58) Field of Classification Search
CPC ............ A63B 24/0075; A63B 2225/20; A63B 2024/0078; A63B 2024/0081; A63B 24/0084; A63B 2225/50; A63B 22/0235; A63B 24/0087; A63B 2022/002; A63B 2071/0691; A63B 2220/70; A63B 22/04; A63B 22/02; A63B 22/0605;
(Continued)

(56) References Cited

U.S. PATENT DOCUMENTS 321,388 A 6/1885 Ruebsam
348,493 A 8/1886 Greene
(Continued)

*Primary Examiner* — Joshua Lee
*Assistant Examiner* — Shila Jalalzadeh Abyaneh
(74) *Attorney, Agent, or Firm* — Maschoff Brennan

(57) ABSTRACT

In general, the present invention relates to exercise devices and systems that can receive and run workout programs that include control command subsets that control the moveable members of a plurality of different exercise devices. Exercise devices of the present invention are able to ignore the control command subset(s) that do not control their moveable member(s) and recognize the control command subset(s) that control their moveable member(s). Exercise devices of the present invention are further able to, if necessary, perform a sizing restriction to the relevant control command subset(s). Motivational content may also be modified in connection with or independently from a sizing restriction made to the control commands. The present invention also relates to a method for controlling one or more exercise device with a workout file that includes control command subsets that control the moveable members of a plurality of different exercise devices.

20 Claims, 9 Drawing Sheets

Related U.S. Application Data

(60) Provisional application No. 61/583,524, filed on Jan. 5, 2012.

(51) Int. Cl.
*A63B 22/06* (2006.01)
*A63B 22/02* (2006.01)
*A63B 22/04* (2006.01)
*G06F 19/00* (2018.01)
*A63B 22/00* (2006.01)
*A63B 21/22* (2006.01)

(52) U.S. Cl.
CPC ...... *A63B 22/0605* (2013.01); *A63B 24/0075* (2013.01); *A63B 71/0622* (2013.01); *G06F 19/3481* (2013.01); *A63B 21/225* (2013.01); *A63B 22/0023* (2013.01); *A63B 22/0056* (2013.01); *A63B 22/0076* (2013.01); *A63B 22/0235* (2013.01); *A63B 22/0242* (2013.01); *A63B 22/0664* (2013.01); *A63B 2022/002* (2013.01); *A63B 2024/009* (2013.01); *A63B 2071/068* (2013.01); *A63B 2071/0638* (2013.01); *A63B 2071/0644* (2013.01); *A63B 2225/20* (2013.01); *A63B 2225/50* (2013.01); *A63B 2230/062* (2013.01); *A63B 2230/30* (2013.01); *A63B 2230/75* (2013.01)

(58) Field of Classification Search
CPC ............ A63B 71/0622; A63B 2230/75; A63B 22/0242; A63B 2071/068; A63B 22/0664; A63B 21/225; A63B 2071/0644; A63B 22/0076; A63B 2230/062; A63B 22/0023; A63B 2024/009; A63B 2071/0638; A63B 2230/30; A63B 22/0056; Y10S 482/901; Y10S 482/90; G06F 19/3481
See application file for complete search history.

(56) References Cited

U.S. PATENT DOCUMENTS

| | | |
|---|---|---|
| 470,837 A | 3/1892 | Hart |
| 549,084 A | 10/1895 | Whitaker |
| 601,307 A | 3/1898 | Salisbury |
| 663,486 A | 12/1900 | Boren |
| 881,521 A | 3/1903 | Wilson |
| 1,020,777 A | 3/1912 | Peterson |
| 1,082,940 A | 12/1913 | Flora |
| 1,715,870 A | 6/1929 | Spain |
| 1,850,530 A | 3/1932 | Brown |
| 1,902,694 A | 3/1933 | Edwards |
| 1,928,089 A | 9/1933 | Blickman |
| 1,930,416 A | 10/1933 | Chauvot |
| 1,973,945 A | 9/1934 | Chavin |
| 2,413,841 A | 1/1947 | Minuto |
| 2,779,139 A | 1/1957 | Boettcher |
| 2,855,200 A | 10/1958 | Blickman |
| 2,874,971 A | 2/1959 | Devery |
| 2,906,532 A | 9/1959 | Echols |
| 3,127,171 A | 3/1964 | Noland et al. |
| 3,378,259 A | 4/1968 | Kupchinski |
| 3,394,934 A | 7/1968 | Petros |
| 3,408,067 A | 10/1968 | Armstrong |
| 3,424,005 A | 1/1969 | Brown |
| 3,432,164 A | 3/1969 | Deeks |
| 3,518,985 A | 7/1970 | Quinton |
| 3,589,715 A | 6/1971 | Mark |
| 3,592,466 A | 7/1971 | Parsons |
| 3,602,502 A | 8/1971 | Jaegar |
| 3,614,097 A | 10/1971 | Blickman |
| 3,659,845 A | 5/1972 | Quinton |
| 3,728,940 A | 4/1973 | Peterson |
| 3,731,917 A | 5/1973 | Townsend |
| 3,738,649 A | 6/1973 | Miller |
| 3,741,538 A | 6/1973 | Useldinger |
| 3,744,480 A | 7/1973 | Gause et al. |
| 3,744,712 A | 7/1973 | Papadopoulos |
| 3,744,794 A | 7/1973 | Gause et al. |
| 3,751,033 A | 8/1973 | Rosenthal |
| 3,767,195 A | 10/1973 | Dimick |
| 3,782,718 A | 1/1974 | Saylor |
| 3,802,698 A | 4/1974 | Burian et al. |
| 3,818,194 A | 6/1974 | Biro |
| 3,822,599 A | 7/1974 | Brentham |
| 3,826,491 A | 7/1974 | Elder |
| 3,834,696 A | 9/1974 | Spector |
| 3,845,756 A | 11/1974 | Olsson |
| 3,851,874 A | 12/1974 | Wilkin |
| 3,858,938 A | 1/1975 | Kristensson et al. |
| 3,859,840 A | 1/1975 | Gause |
| 3,874,657 A | 4/1975 | Niebojewski |
| 3,892,404 A | 7/1975 | Martucci |
| 3,902,480 A | 9/1975 | Wilson |
| 3,903,613 A | 9/1975 | Bisberg |
| 3,974,491 A | 8/1976 | Sipe |
| 4,020,795 A | 5/1977 | Marks |
| 4,026,545 A | 5/1977 | Schonenberger |
| 4,027,531 A | 6/1977 | Dawson |
| 4,066,257 A | 1/1978 | Moller |
| 4,071,235 A | 1/1978 | Zent |
| 4,082,267 A | 4/1978 | Flavell |
| 4,112,928 A | 9/1978 | Putsch |
| 4,120,294 A | 10/1978 | Wolfe |
| 4,120,924 A | 10/1978 | Rainville |
| 4,151,988 A | 5/1979 | Nabinger |
| 4,204,673 A | 5/1980 | Speer, Sr. |
| 4,220,996 A | 9/1980 | Searcy |
| 4,236,239 A | 11/1980 | Imgruth et al. |
| 4,239,092 A | 12/1980 | Janson |
| 4,248,476 A | 2/1981 | Phelps |
| 4,274,625 A | 6/1981 | Gaetano |
| 4,278,095 A | 7/1981 | Lapeyre |
| 4,278,249 A | 7/1981 | Forrest |
| 4,298,893 A | 11/1981 | Holmes |
| 4,300,761 A | 11/1981 | Howard |
| 4,301,808 A | 11/1981 | Taus |
| 4,322,609 A | 3/1982 | Kato |
| 4,323,237 A | 4/1982 | Jungerwirth |
| 4,337,529 A | 6/1982 | Morokawa |
| 4,354,676 A | 10/1982 | Ariel |
| 4,355,645 A | 10/1982 | Mitani et al. |
| 4,358,105 A | 11/1982 | Sweeney, Jr. |
| 4,378,111 A | 3/1983 | Tsuchida et al. |
| 4,383,714 A | 5/1983 | Ishida |
| 4,389,047 A | 6/1983 | Hall |
| 4,408,613 A | 10/1983 | Relyea |
| 4,422,635 A | 12/1983 | Herod |
| 4,423,630 A | 1/1984 | Morrison |
| 4,423,864 A | 1/1984 | Wiik |
| 4,480,831 A | 11/1984 | Muller-Deinhardt |
| 4,493,561 A | 1/1985 | Bouchet |
| 4,495,560 A | 1/1985 | Sugimoto et al. |
| 4,504,055 A | 3/1985 | Wells |
| 4,504,968 A | 3/1985 | Kaneko et al. |
| 4,512,566 A | 4/1985 | Bicocchi |
| 4,512,567 A | 4/1985 | Phillips |
| 4,515,988 A | 5/1985 | Bayer et al. |
| 4,519,603 A | 5/1985 | Decloux |
| 4,529,196 A | 7/1985 | Logan |
| 4,533,136 A | 8/1985 | Smith et al. |
| 4,537,396 A | 8/1985 | Hooper |
| 4,542,897 A | 9/1985 | Melton |
| 4,544,152 A | 10/1985 | Taitel |
| 4,549,044 A | 10/1985 | Durham |
| 4,555,108 A | 11/1985 | Monteiro |
| 4,556,216 A | 12/1985 | Pitkanen |
| 4,566,461 A | 1/1986 | Lubell et al. |
| 4,569,518 A | 2/1986 | Fulks |
| 4,571,682 A | 2/1986 | Silverman et al. |
| 4,573,449 A | 3/1986 | Warnke |
| 4,577,860 A | 3/1986 | Matias et al. |
| 4,577,865 A | 3/1986 | Shishido |

(56) References Cited

U.S. PATENT DOCUMENTS

| | | |
|---|---|---|
| 4,586,495 A | 5/1986 | Petrofsky |
| 4,591,147 A | 5/1986 | Smith et al. |
| 4,592,544 A | 6/1986 | Smith et al. |
| 4,602,779 A | 7/1986 | Ogden |
| 4,625,962 A | 12/1986 | Street |
| 4,630,817 A | 12/1986 | Buckley |
| 4,634,127 A | 1/1987 | Rockwell |
| 4,635,928 A | 1/1987 | Ogden et al. |
| 4,637,605 A | 1/1987 | Ritchie |
| 4,642,769 A | 2/1987 | Petrofsky |
| 4,643,418 A | 2/1987 | Bart |
| 4,647,037 A | 3/1987 | Donohue |
| 4,651,446 A | 3/1987 | Yukawa et al. |
| 4,659,074 A | 4/1987 | Taitel et al. |
| 4,659,078 A | 4/1987 | Blome |
| 4,664,646 A | 5/1987 | Rorabaugh |
| 4,665,388 A | 5/1987 | Ivie et al. |
| 4,671,257 A | 6/1987 | Kaiser et al. |
| 4,678,182 A | 7/1987 | Nakao et al. |
| 4,679,786 A | 7/1987 | Rodgers |
| 4,679,787 A | 7/1987 | Guilbault |
| 4,687,195 A | 8/1987 | Potts |
| 4,702,475 A | 10/1987 | Elstein et al. |
| 4,708,337 A | 11/1987 | Shyu |
| 4,708,338 A | 11/1987 | Potts |
| 4,708,837 A | 11/1987 | Baxter et al. |
| 4,709,917 A | 12/1987 | Yang |
| 4,709,918 A | 12/1987 | Grinblat |
| 4,711,447 A | 12/1987 | Mansfield |
| 4,714,244 A | 12/1987 | Kolomayets et al. |
| 4,720,099 A | 1/1988 | Carlson |
| 4,720,789 A | 1/1988 | Hector et al. |
| 4,726,581 A | 2/1988 | Chang |
| 4,726,582 A | 2/1988 | Fulks |
| 4,728,099 A | 3/1988 | Pitre |
| 4,729,558 A | 3/1988 | Kuo |
| 4,730,828 A | 3/1988 | Lane |
| 4,730,829 A | 3/1988 | Carlson |
| 4,743,009 A | 5/1988 | Beale |
| 4,750,738 A | 6/1988 | Dang |
| 4,757,495 A | 7/1988 | Decker et al. |
| 4,759,540 A | 7/1988 | Yu et al. |
| 4,763,284 A | 8/1988 | Carlin |
| 4,765,613 A | 8/1988 | Voris |
| 4,770,411 A | 9/1988 | Armstrong et al. |
| 4,771,148 A | 9/1988 | Bersonnet |
| 4,771,577 A | 9/1988 | Abe |
| 4,774,679 A | 9/1988 | Carlin |
| 4,776,582 A | 10/1988 | Ramhorst |
| 4,786,049 A | 11/1988 | Lautenschlager |
| 4,786,050 A | 11/1988 | Geschwender |
| 4,789,153 A | 12/1988 | Brown |
| 4,790,522 A | 12/1988 | Drutchas |
| 4,790,528 A | 12/1988 | Nakao et al. |
| 4,798,377 A | 1/1989 | White |
| 4,805,901 A | 2/1989 | Kulick |
| 4,813,665 A | 3/1989 | Carr |
| 4,813,743 A | 3/1989 | Mizelle |
| 4,814,661 A | 3/1989 | Ratzlaff et al. |
| 4,817,938 A | 4/1989 | Nakao et al. |
| 4,817,939 A | 4/1989 | Augspurger et al. |
| 4,817,940 A | 4/1989 | Shaw et al. |
| 4,818,234 A | 4/1989 | Redington |
| 4,819,818 A | 4/1989 | Simkus |
| 4,824,104 A | 4/1989 | Bloch |
| 4,826,153 A | 5/1989 | Schalip |
| 4,828,257 A | 5/1989 | Dyer et al. |
| 4,828,522 A | 5/1989 | Santos |
| 4,828,713 A | 5/1989 | McDonald et al. |
| 4,830,363 A | 5/1989 | Kennedy |
| 4,832,332 A | 5/1989 | Dumbser |
| 4,837,157 A | 6/1989 | Turnell et al. |
| 4,838,543 A | 6/1989 | Armstrong et al. |
| 4,840,372 A | 6/1989 | Oglesby et al. |
| 4,842,266 A | 6/1989 | Sweeney, Sr. |
| 4,842,274 A | 6/1989 | Oosthuizen |
| 4,844,449 A | 7/1989 | Truslaske |
| 4,844,450 A | 7/1989 | Rodgers, Jr. |
| 4,846,693 A | 7/1989 | Baer |
| 4,848,737 A | 7/1989 | Ehrenfield |
| 4,855,942 A | 8/1989 | Bianco |
| 4,860,763 A | 8/1989 | Schminke |
| 4,863,157 A | 9/1989 | Mendel et al. |
| 4,866,704 A | 9/1989 | Bergman |
| 4,867,442 A | 9/1989 | Matthews |
| 4,869,497 A | 9/1989 | Stewart et al. |
| 4,889,108 A | 12/1989 | Bond et al. |
| 4,889,131 A | 12/1989 | Salem et al. |
| 4,891,785 A | 1/1990 | Donohoo |
| 4,900,013 A | 2/1990 | Rodgers, Jr. |
| 4,904,829 A | 2/1990 | Berthaud et al. |
| 4,905,330 A | 3/1990 | Jacobs |
| 4,907,795 A | 3/1990 | Shaw et al. |
| 4,907,973 A | 3/1990 | Hon |
| 4,911,427 A | 3/1990 | Matsumoto et al. |
| 4,912,638 A | 3/1990 | Pratt, Jr. |
| 4,913,396 A | 4/1990 | Dalebout et al. |
| 4,913,423 A | 4/1990 | Farran |
| 4,919,418 A | 4/1990 | Miller |
| 4,921,247 A | 5/1990 | Sterling |
| 4,925,183 A | 5/1990 | Kim |
| 4,925,189 A | 5/1990 | Braeunig |
| 4,927,136 A | 5/1990 | Leask |
| 4,930,770 A | 6/1990 | Baker |
| 4,934,692 A | 6/1990 | Owens |
| 4,934,694 A | 6/1990 | Mcintosh |
| 4,938,469 A | 7/1990 | Crandell |
| 4,938,474 A | 7/1990 | Sweeney et al. |
| 4,949,993 A | 8/1990 | Stark et al. |
| 4,959,713 A | 9/1990 | Morotomi et al. |
| 4,976,424 A | 12/1990 | Sargeant et al. |
| 4,976,435 A | 12/1990 | Shatford |
| 4,983,847 A | 1/1991 | Bryan |
| 4,986,534 A | 1/1991 | Meier et al. |
| 4,986,689 A | 1/1991 | Drutchas |
| 4,992,190 A | 2/1991 | Shtarkman |
| 4,998,725 A | 3/1991 | Watterson et al. |
| 5,000,440 A | 3/1991 | Lynch |
| 5,001,632 A | 3/1991 | Hall Tipping |
| 5,002,271 A | 3/1991 | Gonzales |
| 5,015,926 A | 5/1991 | Casler |
| 5,020,794 A | 6/1991 | Englehardt et al. |
| 5,020,795 A | 6/1991 | Airy et al. |
| 5,027,303 A | 6/1991 | Witte |
| 5,029,801 A | 7/1991 | Dalebout et al. |
| 5,031,455 A | 7/1991 | Cline |
| 5,034,576 A | 7/1991 | Dalebout et al. |
| 5,035,418 A | 7/1991 | Harabayashi |
| RE33,662 E | 8/1991 | Blair et al. |
| 5,037,089 A | 8/1991 | Spagnuolo |
| 5,039,088 A | 8/1991 | Shifferaw |
| 5,039,089 A | 8/1991 | Lapcevic |
| 5,039,091 A | 8/1991 | Johnson |
| 5,046,382 A | 9/1991 | Steinberg |
| 5,052,375 A | 10/1991 | Stark |
| 5,052,684 A | 10/1991 | Kosuge et al. |
| 5,054,774 A | 10/1991 | Belsito |
| 5,062,632 A | 11/1991 | Dalebout et al. |
| 5,067,710 A | 11/1991 | Watterson et al. |
| 5,078,152 A | 1/1992 | Bond et al. |
| 5,086,385 A | 2/1992 | Launey et al. |
| 5,088,729 A | 2/1992 | Dalebout |
| 5,089,960 A | 2/1992 | Sweeney, Jr. |
| 5,104,119 A | 4/1992 | Lynch |
| 5,104,120 A | 4/1992 | Watterson et al. |
| 5,109,778 A | 5/1992 | Berkowitz et al. |
| 5,113,427 A | 5/1992 | Ryoichi et al. |
| 5,114,391 A | 5/1992 | Pitzen et al. |
| 5,117,674 A | 6/1992 | Howard |
| 5,118,112 A | 6/1992 | Bregman et al. |
| 5,137,501 A | 8/1992 | Mertesdorf |
| 5,142,358 A | 8/1992 | Jason |
| 5,145,475 A | 9/1992 | Cares |
| 5,145,481 A | 9/1992 | Friedebach |

(56) References Cited

U.S. PATENT DOCUMENTS

| | | |
|---|---|---|
| 5,149,084 A | 9/1992 | Dalebout et al. |
| 5,152,210 A | 10/1992 | Chen |
| 5,158,093 A | 10/1992 | Shvartz |
| 5,162,029 A | 11/1992 | Schine |
| 5,167,159 A | 12/1992 | Lucking |
| 5,167,850 A | 12/1992 | Shtarkman |
| 5,171,196 A | 12/1992 | Lynch |
| 5,176,602 A | 1/1993 | Roberts |
| 5,180,347 A | 1/1993 | Chen |
| 5,180,351 A | 1/1993 | Ehrenfried |
| 5,180,647 A | 1/1993 | Rowland et al. |
| 5,186,471 A | 2/1993 | Vancraeynest |
| 5,192,255 A | 3/1993 | Dalebout et al. |
| 5,192,257 A | 3/1993 | Panasewicz |
| 5,195,935 A | 3/1993 | Fencel |
| 5,201,772 A | 4/1993 | Maxwell |
| 5,202,424 A | 4/1993 | Vlassara et al. |
| 5,204,670 A | 4/1993 | Stinton |
| 5,205,800 A | 4/1993 | Grant |
| 5,206,671 A | 4/1993 | Eydelman et al. |
| 5,207,628 A | 5/1993 | Graham |
| 5,213,555 A | 5/1993 | Hood |
| 5,226,866 A | 7/1993 | Engel et al. |
| 5,230,672 A | 7/1993 | Brown et al. |
| 5,230,673 A | 7/1993 | Maeyama et al. |
| 5,233,520 A | 8/1993 | Kretsch et al. |
| 5,234,392 A | 8/1993 | Clark |
| 5,234,395 A | 8/1993 | Miller et al. |
| 5,240,417 A | 8/1993 | Smithson et al. |
| 5,243,998 A | 9/1993 | Silverman et al. |
| 5,246,411 A | 9/1993 | Rackman |
| 5,254,066 A | 10/1993 | Brown et al. |
| 5,256,115 A | 10/1993 | Scholder |
| 5,257,084 A | 10/1993 | Marsh |
| 5,260,870 A | 11/1993 | Tsuchiya et al. |
| 5,261,864 A | 11/1993 | Fitzpatrick |
| 5,267,925 A | 12/1993 | Boyd |
| 5,269,081 A | 12/1993 | Gray |
| 5,269,519 A | 12/1993 | Malone |
| 5,277,678 A | 1/1994 | Friedebach et al. |
| 5,290,205 A | 3/1994 | Densmore et al. |
| 5,292,293 A | 3/1994 | Schumacher |
| 5,299,810 A | 4/1994 | Pierce et al. |
| 5,301,154 A | 4/1994 | Suga |
| 5,306,220 A | 4/1994 | Kearney |
| 5,308,296 A | 5/1994 | Eckstein |
| 5,308,300 A | 5/1994 | Chino et al. |
| 5,309,355 A | 5/1994 | Lockwood |
| 5,313,942 A | 5/1994 | Platzker |
| 5,314,389 A | 5/1994 | Dotan |
| 5,314,391 A | 5/1994 | Potash et al. |
| 5,316,534 A | 5/1994 | Dalebout et al. |
| 5,318,487 A | 6/1994 | Golen et al. |
| 5,318,491 A | 6/1994 | Houston |
| 5,323,650 A | 6/1994 | Fullen et al. |
| 5,323,784 A | 6/1994 | Shu |
| 5,328,420 A | 7/1994 | Allen |
| 5,328,422 A | 7/1994 | Nichols |
| 5,335,188 A | 8/1994 | Brisson |
| 5,336,146 A | 8/1994 | Piaget et al. |
| RE34,728 E | 9/1994 | Hall-Tipping |
| 5,352,166 A | 10/1994 | Chang |
| 5,352,167 A | 10/1994 | Ulicny |
| 5,354,251 A | 10/1994 | Sleamaker |
| 5,357,696 A | 10/1994 | Gray |
| 5,358,461 A | 10/1994 | Bailey, Jr. |
| 5,361,091 A | 11/1994 | Hoarty et al. |
| 5,361,778 A | 11/1994 | Seitz |
| 5,362,069 A | 11/1994 | Hall-Tipping |
| 5,362,298 A | 11/1994 | Brown et al. |
| 5,364,271 A | 11/1994 | Aknin et al. |
| 5,368,532 A | 11/1994 | Farnet |
| 5,372,564 A | 12/1994 | Spirito |
| 5,375,068 A | 12/1994 | Palmer et al. |
| 5,377,171 A | 12/1994 | Schlup |
| 5,377,258 A | 12/1994 | Bro |
| 5,382,207 A | 1/1995 | Skowronski et al. |
| 5,382,209 A | 1/1995 | Pasier |
| 5,383,827 A | 1/1995 | Stern |
| 5,385,519 A | 1/1995 | Hsu |
| 5,385,520 A | 1/1995 | Lepine et al. |
| 5,387,164 A | 2/1995 | Brown, Jr. |
| 5,391,080 A | 2/1995 | Bernacki |
| 5,396,340 A | 3/1995 | Ishii et al. |
| 5,403,252 A | 4/1995 | Leon et al. |
| 5,407,402 A | 4/1995 | Brown et al. |
| 5,409,435 A | 4/1995 | Daniels |
| 5,410,471 A | 4/1995 | Alyfuku et al. |
| 5,410,472 A | 4/1995 | Anderson |
| 5,417,222 A | 5/1995 | Dempsey et al. |
| 5,417,643 A | 5/1995 | Taylor |
| 5,419,562 A | 5/1995 | Cromarty |
| 5,421,801 A | 6/1995 | Davies, III et al. |
| 5,431,612 A | 7/1995 | Holden |
| 5,433,679 A | 7/1995 | Szymczak et al. |
| 5,435,799 A | 7/1995 | Lundin |
| 5,437,289 A | 8/1995 | Liverance |
| 5,445,583 A | 8/1995 | Habing |
| 5,451,922 A | 9/1995 | Hamilton |
| 5,452,269 A | 9/1995 | Cherdak |
| 5,454,772 A | 10/1995 | Rodden |
| 5,456,262 A | 10/1995 | Birnbaum |
| 5,456,648 A | 10/1995 | Edinburg |
| 5,462,051 A | 10/1995 | Oka et al. |
| 5,462,503 A | 10/1995 | Benjamin et al. |
| 5,462,504 A | 10/1995 | Trulaske et al. |
| 5,466,200 A | 11/1995 | Ulrich et al. |
| 5,469,740 A | 11/1995 | French et al. |
| 5,472,205 A | 12/1995 | Bouton |
| 5,474,077 A | 12/1995 | Suga |
| 5,474,090 A | 12/1995 | Begun et al. |
| 5,476,428 A | 12/1995 | Potash et al. |
| 5,476,430 A | 12/1995 | Lee et al. |
| 5,478,295 A | 12/1995 | Fracchia |
| 5,482,472 A | 1/1996 | Garoni et al. |
| 5,484,362 A | 1/1996 | Skowronski et al. |
| 5,484,389 A | 1/1996 | Stark |
| 5,486,001 A | 1/1996 | Baker |
| 5,489,249 A | 2/1996 | Brewer et al. |
| 5,493,127 A | 2/1996 | Lloyd et al. |
| 5,499,956 A | 3/1996 | Habing et al. |
| 5,510,828 A | 4/1996 | Lutterbach |
| 5,512,025 A | 4/1996 | Dalebout et al. |
| 5,512,029 A | 4/1996 | Barnard |
| 5,516,334 A | 5/1996 | Easton |
| 5,518,471 A | 5/1996 | Hettinger et al. |
| 5,519,189 A | 5/1996 | Gibisch |
| 5,520,599 A | 5/1996 | Chen |
| 5,524,110 A | 6/1996 | Danneels et al. |
| 5,524,637 A | 6/1996 | Erickson |
| 5,527,239 A | 6/1996 | Abbondanza |
| 5,527,245 A | 6/1996 | Dalebout et al. |
| 5,535,664 A | 7/1996 | Rokowski |
| 5,538,486 A | 7/1996 | France et al. |
| 5,542,420 A | 8/1996 | Goldman |
| 5,542,672 A | 8/1996 | Meredith |
| 5,547,439 A | 8/1996 | Rawls et al. |
| 5,569,120 A | 10/1996 | Anjanappa et al. |
| 5,572,643 A | 11/1996 | Judson |
| 5,576,951 A | 11/1996 | Lockwood |
| 5,577,186 A | 11/1996 | Mann, II et al. |
| 5,577,981 A | 11/1996 | Jarvik |
| 5,577,985 A | 11/1996 | Miller |
| 5,580,249 A | 12/1996 | Jacobsen et al. |
| 5,582,563 A | 12/1996 | Fan |
| 5,584,700 A | 12/1996 | Feldman et al. |
| 5,584,779 A | 12/1996 | Knecht |
| 5,584,784 A | 12/1996 | Wu |
| 5,585,561 A | 12/1996 | Bahl et al. |
| 5,585,583 A | 12/1996 | Owen |
| 5,586,962 A | 12/1996 | Hallmark |
| 5,590,128 A | 12/1996 | Maloney et al. |
| 5,590,181 A | 12/1996 | Hogan et al. |
| 5,591,104 A | 1/1997 | Andrus et al. |

(56) References Cited

U.S. PATENT DOCUMENTS

| | | |
|---|---|---|
| 5,591,908 A | 1/1997 | Reid |
| 5,598,849 A | 2/1997 | Browne |
| 5,600,310 A | 2/1997 | Whipple, III et al. |
| 5,605,336 A | 2/1997 | Gaoiran |
| 5,613,216 A | 3/1997 | Galler |
| 5,618,245 A | 4/1997 | Trulaske et al. |
| 5,618,250 A | 4/1997 | Butz |
| 5,619,412 A | 4/1997 | Hapka |
| 5,619,991 A | 4/1997 | Sloane |
| 5,626,539 A | 5/1997 | Piaget |
| 5,638,343 A | 6/1997 | Ticknor |
| 5,643,142 A | 7/1997 | Salerno et al. |
| 5,643,146 A | 7/1997 | Stark et al. |
| 5,643,147 A | 7/1997 | Huang |
| 5,645,509 A | 7/1997 | Brewer et al. |
| 5,645,513 A | 7/1997 | Haydocy et al. |
| 5,652,304 A | 7/1997 | Calderon et al. |
| 5,652,824 A | 7/1997 | Hirayama et al. |
| 5,655,945 A | 8/1997 | Jani |
| 5,655,997 A | 8/1997 | Greenberg et al. |
| 5,659,691 A | 8/1997 | Durward et al. |
| 5,662,557 A | 9/1997 | Watterson et al. |
| 5,665,031 A | 9/1997 | Hsieh |
| 5,667,459 A | 9/1997 | Su |
| 5,669,833 A | 9/1997 | Stone |
| 5,672,140 A | 9/1997 | Watterson et al. |
| 5,674,156 A | 10/1997 | Watterson et al. |
| 5,674,453 A | 10/1997 | Watterson et al. |
| 5,676,138 A | 10/1997 | Zawilinski |
| 5,676,624 A | 10/1997 | Watterson et al. |
| 5,685,804 A | 11/1997 | Whan-Tong et al. |
| 5,690,582 A | 11/1997 | Ulrich et al. |
| 5,690,852 A | 11/1997 | Saito et al. |
| 5,693,004 A | 12/1997 | Carlson et al. |
| 5,695,400 A | 12/1997 | Fennell, Jr. et al. |
| 5,697,834 A | 12/1997 | Heumann et al. |
| 5,702,323 A | 12/1997 | Poulton |
| 5,704,875 A | 1/1998 | Tanabe |
| 5,704,879 A | 1/1998 | Watterson et al. |
| 5,710,884 A | 1/1998 | Dedrick |
| 5,711,746 A | 1/1998 | Carlson |
| 5,713,794 A | 2/1998 | Shimojima et al. |
| 5,719,825 A | 2/1998 | Dotter |
| 5,720,771 A | 2/1998 | Snell |
| 5,721,539 A | 2/1998 | Goetzl |
| 5,722,418 A | 3/1998 | Bro |
| 5,722,420 A | 3/1998 | Lee |
| 5,724,025 A | 3/1998 | Tavori |
| 5,733,228 A | 3/1998 | Stevens |
| 5,734,625 A | 3/1998 | Kondo |
| 5,738,612 A | 4/1998 | Tsuda |
| 5,739,457 A | 4/1998 | Devecka |
| 5,741,205 A | 4/1998 | Doll et al. |
| 5,743,833 A | 4/1998 | Watterson et al. |
| 5,743,835 A | 4/1998 | Trotter |
| 5,749,372 A | 5/1998 | Allen |
| 5,749,807 A | 5/1998 | Webb |
| 5,749,809 A | 5/1998 | Lin |
| 5,752,883 A | 5/1998 | Butcher et al. |
| 5,752,897 A | 5/1998 | Skowronski et al. |
| 5,754,765 A | 5/1998 | Danneels et al. |
| 5,755,645 A | 5/1998 | Miller et al. |
| 5,759,199 A | 6/1998 | Snell et al. |
| 5,760,353 A | 6/1998 | Rapp |
| 5,762,503 A | 6/1998 | Hoo et al. |
| 5,769,755 A | 6/1998 | Henry et al. |
| 5,769,759 A | 6/1998 | Alter |
| 5,771,354 A | 6/1998 | Crawford |
| 5,772,508 A | 6/1998 | Sugita et al. |
| 5,777,678 A | 7/1998 | Ogata et al. |
| 5,779,596 A | 7/1998 | Weber |
| 5,782,639 A | 7/1998 | Beal |
| 5,785,630 A | 7/1998 | Bobick et al. |
| 5,785,631 A | 7/1998 | Heidecke |
| 5,785,632 A | 7/1998 | Greenberg et al. |
| 5,790,785 A | 8/1998 | Klug et al. |
| 5,794,210 A | 8/1998 | Goldhaber et al. |
| 5,797,805 A | 8/1998 | Lubell et al. |
| 5,799,281 A | 8/1998 | Login et al. |
| 5,803,870 A | 9/1998 | Buhler |
| 5,810,696 A | 9/1998 | Webb |
| 5,810,747 A | 9/1998 | Brudny et al. |
| 5,813,142 A | 9/1998 | Demon |
| 5,813,864 A | 9/1998 | Ikuta |
| 5,813,945 A | 9/1998 | Bernacki |
| 5,813,947 A | 9/1998 | Densmore |
| 5,816,372 A | 10/1998 | Carlson et al. |
| 5,816,443 A | 10/1998 | Bustos |
| 5,820,525 A | 10/1998 | Riley |
| 5,823,913 A | 10/1998 | Aruin |
| 5,825,983 A | 10/1998 | Park et al. |
| 5,827,154 A | 10/1998 | Gill |
| 5,827,155 A | 10/1998 | Jensen et al. |
| 5,830,107 A | 11/1998 | Brigliadoro |
| 5,830,113 A | 11/1998 | Coody et al. |
| 5,833,577 A | 11/1998 | Hurt |
| 5,833,583 A | 11/1998 | Chuang |
| 5,836,770 A | 11/1998 | Powers |
| 5,838,906 A | 11/1998 | Doyle et al. |
| 5,839,990 A | 11/1998 | Virkkala |
| 5,845,230 A | 12/1998 | Lamberson |
| 5,848,396 A | 12/1998 | Gerace |
| 5,854,833 A | 12/1998 | Hogan et al. |
| 5,855,537 A | 1/1999 | Coody et al. |
| 5,855,538 A | 1/1999 | Argabright |
| 5,857,939 A | 1/1999 | Kaufman |
| 5,860,893 A | 1/1999 | Watterson et al. |
| 5,864,018 A | 1/1999 | Morser et al. |
| 5,865,733 A | 2/1999 | Malinouskas et al. |
| 5,868,648 A | 2/1999 | Coody et al. |
| 5,873,369 A | 2/1999 | Laniado et al. |
| 5,876,095 A | 3/1999 | Johnston |
| 5,879,270 A | 3/1999 | Huish et al. |
| 5,880,677 A | 3/1999 | Lestician |
| 5,888,172 A | 3/1999 | Andrus et al. |
| 5,890,149 A | 3/1999 | Schmonsees |
| 5,890,906 A | 4/1999 | Macri |
| 5,890,995 A | 4/1999 | Bobick et al. |
| 5,890,996 A | 4/1999 | Frame et al. |
| 5,890,997 A | 4/1999 | Roth |
| 5,891,042 A | 4/1999 | Sham et al. |
| 5,897,463 A | 4/1999 | Maresh |
| 5,899,833 A | 5/1999 | Ryan et al. |
| 5,899,834 A | 5/1999 | Dalebout et al. |
| 5,899,963 A | 5/1999 | Hutchings |
| 5,902,214 A | 5/1999 | Makikawa et al. |
| 5,905,442 A | 5/1999 | Mosebrook et al. |
| 5,906,494 A | 5/1999 | Ogawa et al. |
| 5,906,581 A | 5/1999 | Tsuda |
| 5,909,544 A | 6/1999 | Anderson, II et al. |
| 5,910,070 A | 6/1999 | Henry et al. |
| 5,911,044 A | 6/1999 | Lo et al. |
| 5,911,132 A | 6/1999 | Sloane |
| 5,911,687 A | 6/1999 | Sato et al. |
| 5,913,310 A | 6/1999 | Brown |
| 5,913,830 A | 6/1999 | Miles |
| 5,916,063 A | 6/1999 | Alessandri |
| 5,916,065 A | 6/1999 | McBride et al. |
| 5,917,405 A | 6/1999 | Joao |
| 5,919,117 A | 7/1999 | Thompson et al. |
| 5,921,891 A | 7/1999 | Browne |
| 5,921,896 A | 7/1999 | Boland |
| 5,929,748 A | 7/1999 | Odinak |
| 5,929,782 A | 7/1999 | Stark |
| 5,929,848 A | 7/1999 | Albukerk et al. |
| 5,931,763 A | 8/1999 | Alessandri |
| 5,937,387 A | 8/1999 | Summerell et al. |
| 5,938,571 A | 8/1999 | Stevens |
| 5,941,797 A | 8/1999 | Kashiwaguchi |
| 5,944,638 A | 8/1999 | Maresh |
| 5,947,868 A | 9/1999 | Dugan |
| 5,947,869 A | 9/1999 | Shea |
| 5,947,872 A | 9/1999 | Ryan et al. |
| 5,956,509 A | 9/1999 | Kevner |

(56) References Cited

U.S. PATENT DOCUMENTS

| | | |
|---|---|---|
| 5,957,699 A | 9/1999 | Peterson et al. |
| 5,961,561 A | 10/1999 | Wakefield, II |
| 5,961,593 A | 10/1999 | Gabber et al. |
| 5,964,701 A | 10/1999 | Asada et al. |
| 5,967,975 A | 10/1999 | Ridgeway |
| 5,970,340 A | 10/1999 | Edgar |
| 5,971,902 A | 10/1999 | Robertson et al. |
| 5,973,696 A | 10/1999 | Agranat et al. |
| 5,976,083 A | 11/1999 | Richardson et al. |
| 5,980,429 A | 11/1999 | Nashner |
| 5,981,168 A | 11/1999 | Reiner et al. |
| 5,984,798 A | 11/1999 | Gilmour |
| 5,984,839 A | 11/1999 | Corkum |
| 5,990,405 A | 11/1999 | Auten et al. |
| 5,993,356 A | 11/1999 | Houston et al. |
| 5,993,362 A | 11/1999 | Ghobadi |
| 5,995,868 A | 11/1999 | Dorfmeister et al. |
| 5,997,476 A | 12/1999 | Brown |
| 6,002,982 A | 12/1999 | Fry |
| 6,004,243 A | 12/1999 | Ewert |
| 6,010,451 A | 1/2000 | Clawson |
| 6,013,007 A | 1/2000 | Root et al. |
| 6,013,009 A | 1/2000 | Karkanen |
| 6,013,011 A | 1/2000 | Moore et al. |
| 6,014,432 A | 1/2000 | Modney |
| 6,014,634 A | 1/2000 | Scroggie et al. |
| 6,018,705 A | 1/2000 | Gaudet et al. |
| 6,027,428 A | 2/2000 | Thomas et al. |
| 6,027,429 A | 2/2000 | Daniels |
| 6,033,227 A | 3/2000 | Ishige |
| 6,033,344 A | 3/2000 | Trulaske et al. |
| 6,039,677 A | 3/2000 | Spletzer |
| 6,042,516 A | 3/2000 | Norton |
| 6,042,519 A | 3/2000 | Shea |
| 6,045,487 A | 4/2000 | Miller |
| 6,045,490 A | 4/2000 | Shafer |
| 6,050,822 A | 4/2000 | Faughn |
| 6,050,921 A | 4/2000 | Wang |
| 6,050,923 A | 4/2000 | Yu |
| 6,050,924 A | 4/2000 | Shea |
| 6,050,942 A | 4/2000 | Rust et al. |
| 6,053,737 A | 4/2000 | Babbitt et al. |
| 6,053,844 A | 4/2000 | Clem |
| 6,055,513 A | 4/2000 | Katz et al. |
| 6,055,573 A | 4/2000 | Gardenswartz et al. |
| 6,056,670 A | 5/2000 | Shu et al. |
| 6,059,576 A | 5/2000 | Brann |
| 6,059,692 A | 5/2000 | Hickman |
| 6,065,572 A | 5/2000 | Schober et al. |
| 6,066,075 A | 5/2000 | Poulton |
| 6,066,077 A | 5/2000 | Horst |
| 6,066,705 A | 5/2000 | Calderon et al. |
| 6,068,578 A | 5/2000 | Wang |
| 6,075,525 A | 6/2000 | Hsieh |
| 6,086,379 A | 7/2000 | Pendergast et al. |
| 6,090,017 A | 7/2000 | Wang |
| 6,099,439 A | 8/2000 | Ryan et al. |
| 6,102,832 A | 8/2000 | Tani |
| 6,102,846 A | 8/2000 | Patton et al. |
| 6,103,203 A | 8/2000 | Fischer |
| 6,106,297 A | 8/2000 | Pollak et al. |
| 6,110,076 A | 8/2000 | Hurt |
| 6,113,537 A | 9/2000 | Castano |
| 6,122,340 A | 9/2000 | Darley et al. |
| 6,126,577 A | 10/2000 | Chang |
| 6,128,663 A | 10/2000 | Thomas |
| 6,132,337 A | 10/2000 | Krupka et al. |
| 6,132,340 A | 10/2000 | Wang |
| 6,133,610 A | 10/2000 | Bolam et al. |
| 6,135,924 A | 10/2000 | Gibbs et al. |
| 6,142,870 A | 11/2000 | Wada et al. |
| 6,142,912 A | 11/2000 | Profaci |
| 6,142,913 A | 11/2000 | Ewert |
| 6,146,313 A | 11/2000 | Whan-Tong et al. |
| 6,148,262 A | 11/2000 | Fry |
| 6,151,586 A | 11/2000 | Brown |
| 6,152,854 A | 11/2000 | Carmein |
| 6,152,856 A | 11/2000 | Studor et al. |
| 6,159,131 A | 12/2000 | Pfeffer |
| 6,162,151 A | 12/2000 | Tani et al. |
| 6,162,183 A | 12/2000 | Hoover |
| 6,162,189 A | 12/2000 | Girone et al. |
| 6,171,186 B1 | 1/2001 | Kurosawa et al. |
| 6,171,218 B1 | 1/2001 | Shea |
| 6,174,267 B1 | 1/2001 | Dalebout |
| 6,174,268 B1 | 1/2001 | Novak |
| 6,175,608 B1 | 1/2001 | Pyles et al. |
| 6,176,241 B1 | 1/2001 | Blau et al. |
| 6,176,814 B1 | 1/2001 | Ryan et al. |
| 6,179,746 B1 | 1/2001 | Delman |
| 6,179,753 B1 | 1/2001 | Barker et al. |
| 6,183,259 B1 | 2/2001 | Macri et al. |
| 6,183,425 B1 | 2/2001 | Whalen |
| 6,186,145 B1 | 2/2001 | Brown |
| 6,186,290 B1 | 2/2001 | Carlson |
| 6,186,929 B1 | 2/2001 | Endelman et al. |
| 6,193,631 B1 | 2/2001 | Hickman |
| 6,198,394 B1 | 3/2001 | Jacobsen et al. |
| 6,211,451 B1 | 4/2001 | Tohgi et al. |
| 6,220,865 B1 | 4/2001 | Macri et al. |
| 6,221,451 B1 | 4/2001 | Lauer et al. |
| 6,221,667 B1 | 4/2001 | Reiner et al. |
| 6,224,387 B1 | 5/2001 | Jones |
| 6,224,516 B1 | 5/2001 | Disch |
| 6,225,977 B1 | 5/2001 | Li |
| 6,227,968 B1 | 5/2001 | Suzuki et al. |
| 6,230,501 B1 | 5/2001 | Bailey, Sr. et al. |
| 6,231,481 B1 | 5/2001 | Brock |
| 6,231,482 B1 | 5/2001 | Thompson |
| 6,234,936 B1 | 5/2001 | Wang |
| 6,238,323 B1 | 5/2001 | Simonson |
| 6,241,524 B1 | 6/2001 | Aoshima et al. |
| 6,244,987 B1 | 6/2001 | Ohsuga et al. |
| 6,244,988 B1 | 6/2001 | Delman |
| 6,251,048 B1 | 6/2001 | Kaufman |
| 6,252,153 B1 | 6/2001 | Toyama |
| 6,254,513 B1 | 7/2001 | Takenaka et al. |
| 6,259,944 B1 | 7/2001 | Margulis et al. |
| 6,260,970 B1 | 7/2001 | Horn |
| 6,278,378 B1 | 8/2001 | Feiner et al. |
| 6,280,362 B1 | 8/2001 | Dalebout et al. |
| 6,283,760 B1 | 9/2001 | Wakamoto |
| 6,283,859 B1 | 9/2001 | Carlson et al. |
| 6,283,896 B1 | 9/2001 | Grunfeld |
| 6,287,239 B1 | 9/2001 | Hernandez |
| 6,292,688 B1 | 9/2001 | Patton |
| 6,293,802 B1 | 9/2001 | Ahlgren |
| 6,307,167 B1 | 10/2001 | Kajio et al. |
| 6,308,565 B1 | 10/2001 | French |
| 6,312,363 B1 | 11/2001 | Watterson et al. |
| 6,312,366 B1 | 11/2001 | Prusick |
| 6,313,363 B1 | 11/2001 | Joly et al. |
| 6,314,058 B1 | 11/2001 | Lee |
| 6,317,151 B1 | 11/2001 | Ohsuga et al. |
| 6,322,451 B1 | 11/2001 | Miura |
| 6,328,677 B1 | 12/2001 | Drapeau |
| 6,334,624 B1 | 1/2002 | Giglio |
| 6,336,891 B1 | 1/2002 | Fedrigon et al. |
| 6,342,028 B1 | 1/2002 | De Sane |
| 6,345,197 B1 | 2/2002 | Fabrizio |
| 6,350,218 B1 | 2/2002 | Dalebout et al. |
| 6,356,856 B1 | 3/2002 | Damen et al. |
| 6,358,187 B1 | 3/2002 | Smith |
| 6,368,251 B1 | 4/2002 | Casler |
| 6,369,313 B2 | 4/2002 | Devecka |
| 6,371,123 B1 | 4/2002 | Stark et al. |
| 6,371,850 B1 | 4/2002 | Sonoda |
| 6,385,651 B2 | 5/2002 | Dancs et al. |
| 6,390,923 B1 | 5/2002 | Yoshitomi et al. |
| 6,398,695 B2 | 6/2002 | Miller |
| 6,402,520 B1 | 6/2002 | Freer |
| 6,402,558 B1 | 6/2002 | Hung-Ju et al. |
| 6,404,418 B1 | 6/2002 | Leem |
| 6,405,077 B1 | 6/2002 | Birnbaum et al. |

(56) References Cited

U.S. PATENT DOCUMENTS

| | | |
|---|---|---|
| 6,409,513 B1 | 6/2002 | Kawamura et al. |
| 6,418,394 B1 | 7/2002 | Puolakanaho et al. |
| 6,419,611 B1 | 7/2002 | Levine et al. |
| 6,421,358 B1 | 7/2002 | Stimmel et al. |
| 6,428,449 B1 | 8/2002 | Apseloff |
| 6,446,745 B1 | 9/2002 | Lee |
| 6,447,424 B1 | 9/2002 | Ashby et al. |
| 6,450,922 B1 | 9/2002 | Henderson et al. |
| 6,458,060 B1 | 10/2002 | Watterson et al. |
| 6,458,061 B2 | 10/2002 | Simonson |
| 6,461,279 B1 | 10/2002 | Kuo |
| 6,463,385 B1 | 10/2002 | Fry |
| 6,464,618 B1 | 10/2002 | Shea |
| 6,473,483 B2 | 10/2002 | Pyles |
| 6,474,193 B1 | 11/2002 | Farney |
| 6,475,115 B1 | 11/2002 | Candito |
| 6,475,122 B2 | 11/2002 | Wu |
| 6,478,736 B1 | 11/2002 | Mault |
| 6,484,062 B1 | 11/2002 | Kim |
| 6,493,652 B1 | 12/2002 | Ohlenbusch et al. |
| 6,497,426 B2 | 12/2002 | Vanpelt |
| 6,503,173 B2 | 1/2003 | Clem |
| 6,511,402 B2 | 1/2003 | Shu et al. |
| 6,513,381 B2 | 2/2003 | Fyfe et al. |
| 6,513,532 B2 | 2/2003 | Mault et al. |
| 6,515,593 B1 | 2/2003 | Stark et al. |
| 6,527,674 B1 | 3/2003 | Clem |
| 6,527,685 B2 | 3/2003 | Endelman et al. |
| 6,527,711 B1 | 3/2003 | Stivoric et al. |
| 6,527,712 B1 | 3/2003 | Brown et al. |
| 6,530,864 B1 | 3/2003 | Parks |
| 6,539,931 B2 | 4/2003 | Trajkovic et al. |
| 6,547,702 B1 | 4/2003 | Heidecke |
| 6,551,220 B1 | 4/2003 | Schroeder |
| 6,560,903 B1 | 5/2003 | Darley |
| 6,561,951 B2 | 5/2003 | Cannon et al. |
| 6,561,955 B1 | 5/2003 | Dreissigacker et al. |
| 6,563,489 B1 | 5/2003 | Latypov et al. |
| 6,572,511 B1 | 6/2003 | Volpe |
| 6,572,512 B2 | 6/2003 | Anderson et al. |
| 6,579,214 B1 | 6/2003 | Crump |
| 6,582,342 B2 | 6/2003 | Kaufman |
| 6,585,622 B1 | 7/2003 | Shum et al. |
| 6,592,502 B1 | 7/2003 | Phillips |
| 6,599,223 B2 | 7/2003 | Wang |
| 6,601,016 B1 | 7/2003 | Brown et al. |
| 6,601,358 B2 | 8/2003 | Panatta |
| 6,602,191 B2 | 8/2003 | Quy |
| 6,604,008 B2 | 8/2003 | Chudley et al. |
| 6,604,023 B1 | 8/2003 | Brown et al. |
| 6,604,419 B2 | 8/2003 | Guzman |
| 6,605,020 B1 | 8/2003 | Huang |
| 6,605,038 B1 | 8/2003 | Teller et al. |
| 6,605,044 B2 | 8/2003 | Bimbaum |
| 6,606,374 B1 | 8/2003 | Rokoff et al. |
| 6,611,789 B1 | 8/2003 | Darley |
| 6,612,170 B2 | 9/2003 | Brown |
| 6,612,492 B1 | 9/2003 | Yen |
| 6,616,578 B2 | 9/2003 | Alessandri |
| 6,619,835 B2 | 9/2003 | Kita |
| 6,626,799 B2 | 9/2003 | Watterson et al. |
| 6,626,800 B1 | 9/2003 | Casler |
| 6,626,803 B1 | 9/2003 | Oglesby et al. |
| 6,629,909 B1 | 10/2003 | Stearns et al. |
| 6,634,992 B1 | 10/2003 | Ogawa |
| 6,635,015 B2 | 10/2003 | Sagel |
| 6,638,160 B2 | 10/2003 | Yoshitomi |
| 6,645,124 B1 | 11/2003 | Clem |
| 6,645,125 B1 | 11/2003 | Stearns et al. |
| 6,645,126 B1 | 11/2003 | Martin et al. |
| 6,648,353 B1 | 11/2003 | Cabal |
| 6,648,798 B2 | 11/2003 | Yoo |
| 6,648,802 B2 | 11/2003 | Ware |
| 6,656,091 B1 | 12/2003 | Abelbeck |
| 6,659,916 B1 | 12/2003 | Shea |
| 6,659,946 B1 | 12/2003 | Batchelor et al. |
| 6,660,949 B2 | 12/2003 | Kamino et al. |
| 6,669,600 B2 | 12/2003 | Warner |
| 6,672,991 B2 | 1/2004 | O'Malley |
| 6,672,994 B1 | 1/2004 | Stearns et al. |
| 6,676,569 B1 | 1/2004 | Radow |
| 6,677,299 B2 | 1/2004 | Stern et al. |
| 6,681,014 B1 | 1/2004 | Ghassabian |
| 6,685,480 B2 | 2/2004 | Nishimoto et al. |
| 6,685,607 B1 | 2/2004 | Olson |
| 6,687,535 B2 | 2/2004 | Hautala et al. |
| 6,689,057 B1 | 2/2004 | Shinsel et al. |
| 6,691,839 B1 | 2/2004 | El-Kassouf |
| 6,695,694 B2 | 2/2004 | Ishikawa et al. |
| 6,695,799 B2 | 2/2004 | Kitadou et al. |
| 6,700,788 B2 | 3/2004 | Matsushita et al. |
| 6,701,271 B2 | 3/2004 | Willner et al. |
| 6,702,719 B1 | 3/2004 | Brown et al. |
| 6,712,737 B1 | 3/2004 | Nusbaum |
| 6,716,139 B1 | 4/2004 | Hosseinzadeh-Dolkhani |
| 6,719,667 B2 | 4/2004 | Wong et al. |
| 6,722,888 B1 | 4/2004 | Macri et al. |
| 6,726,113 B2 | 4/2004 | Guo |
| 6,730,002 B2 | 5/2004 | Hald et al. |
| 6,736,759 B1 | 5/2004 | Stubbs et al. |
| 6,740,007 B2 | 5/2004 | Gordon et al. |
| 6,740,009 B1 | 5/2004 | Hall |
| 6,746,247 B2 | 6/2004 | Barton |
| 6,746,371 B1 | 6/2004 | Brown et al. |
| 6,749,432 B2 | 6/2004 | French et al. |
| 6,749,536 B1 | 6/2004 | Cuskaden et al. |
| 6,749,537 B1 | 6/2004 | Hickman |
| 6,749,540 B1 | 6/2004 | Pasero et al. |
| 6,749,546 B2 | 6/2004 | Yang |
| 6,751,439 B2 | 6/2004 | Tice et al. |
| 6,757,572 B1 | 6/2004 | Forest |
| 6,761,667 B1 | 7/2004 | Cutler et al. |
| 6,764,429 B1 | 7/2004 | Michalow |
| 6,764,431 B2 | 7/2004 | Yoss |
| 6,769,689 B1 | 8/2004 | Shimomura et al. |
| 6,776,740 B1 | 8/2004 | Anderson et al. |
| 6,783,482 B2 | 8/2004 | Oglesby et al. |
| 6,786,415 B2 | 9/2004 | Yiu |
| 6,786,821 B2 | 9/2004 | Nobe et al. |
| 6,786,848 B2 | 9/2004 | Yamashita et al. |
| 6,790,163 B1 | 9/2004 | Van De Laarschot |
| 6,790,178 B1 | 9/2004 | Mault et al. |
| 6,793,607 B2 | 9/2004 | Neil |
| 6,796,927 B2 | 9/2004 | Toyama |
| 6,798,378 B1 | 9/2004 | Walters |
| 6,807,869 B2 | 10/2004 | Farringdon et al. |
| 6,808,472 B1 | 10/2004 | Hickman |
| 6,808,473 B2 | 10/2004 | Hisano et al. |
| 6,811,516 B1 | 11/2004 | Dugan |
| 6,811,520 B2 | 11/2004 | Wu |
| 6,817,979 B2 | 11/2004 | Nihtilä |
| 6,823,036 B1 | 11/2004 | Chen |
| 6,823,327 B1 | 11/2004 | Klug |
| 6,824,502 B1 | 11/2004 | Huang |
| 6,825,164 B1 | 11/2004 | Stern et al. |
| 6,825,876 B1 | 11/2004 | Easwar et al. |
| 6,827,669 B2 | 12/2004 | Cohen et al. |
| 6,827,670 B1 | 12/2004 | Stark et al. |
| 6,827,822 B2 | 12/2004 | Tao et al. |
| 6,830,540 B2 | 12/2004 | Watterson |
| 6,830,541 B2 | 12/2004 | Wu |
| 6,835,166 B1 | 12/2004 | Stearns et al. |
| 6,837,827 B1 | 1/2005 | Lee et al. |
| 6,840,904 B2 | 1/2005 | Goldberg |
| 6,846,270 B1 | 1/2005 | Etnyre |
| 6,852,068 B2 | 2/2005 | Ogawa |
| 6,852,069 B2 | 2/2005 | Park |
| 6,859,215 B1 | 2/2005 | Brown et al. |
| 6,863,641 B1 | 3/2005 | Brown et al. |
| 6,866,613 B1 | 3/2005 | Brown et al. |
| 6,872,077 B2 | 3/2005 | Yeager |
| 6,872,187 B1 | 3/2005 | Stark et al. |
| 6,875,157 B1 | 4/2005 | Wang |
| 6,876,496 B2 | 4/2005 | French et al. |

(56) References Cited

U.S. PATENT DOCUMENTS

| | | |
|---|---|---|
| 6,876,947 B1 | 4/2005 | Darley et al. |
| 6,878,099 B2 | 4/2005 | Corbalis et al. |
| 6,881,176 B2 | 4/2005 | Oishi et al. |
| 6,882,955 B1 | 4/2005 | Ohlenbusch et al. |
| 6,885,971 B2 | 4/2005 | Vock et al. |
| 6,886,613 B1 | 5/2005 | Zahdeh |
| 6,887,190 B1 | 5/2005 | Azari |
| 6,902,513 B1 | 6/2005 | Mcclure |
| 6,905,440 B2 | 6/2005 | Heppert |
| 6,908,417 B2 | 6/2005 | Jackson |
| 6,915,271 B1 | 7/2005 | Meyer et al. |
| 6,918,858 B2 | 7/2005 | Watterson et al. |
| 6,918,860 B1 | 7/2005 | Nusbaum |
| 6,921,351 B1 | 7/2005 | Hickman et al. |
| 6,923,747 B1 | 8/2005 | Chu |
| 6,934,658 B2 | 8/2005 | Clabes et al. |
| 6,936,007 B2 | 8/2005 | Quy |
| 6,937,289 B1 | 8/2005 | Ranta et al. |
| 6,939,271 B1 | 9/2005 | Whan-Tong et al. |
| 6,942,599 B1 | 9/2005 | Racine |
| 6,945,916 B2 | 9/2005 | Schroeder |
| 6,949,054 B1 | 9/2005 | Stearns |
| 6,952,221 B1 | 10/2005 | Holtz et al. |
| 6,955,542 B2 | 10/2005 | Roncalez et al. |
| 6,960,156 B2 | 11/2005 | Smith |
| 6,971,972 B1 | 12/2005 | Mcgovern |
| 6,971,973 B2 | 12/2005 | Cohen et al. |
| 6,974,403 B2 | 12/2005 | Wong et al. |
| 6,974,404 B1 | 12/2005 | Watterson et al. |
| 6,975,910 B1 | 12/2005 | Brown et al. |
| 6,976,624 B2 | 12/2005 | Hsiao |
| 6,976,958 B2 | 12/2005 | Quy |
| 6,991,586 B2 | 1/2006 | Lapcevic |
| 6,996,852 B1 | 2/2006 | Cabrera |
| 6,997,852 B2 | 2/2006 | Watterson et al. |
| 6,997,853 B1 | 2/2006 | Cuskaden et al. |
| 7,008,356 B2 | 3/2006 | Hung |
| 7,015,950 B1 | 3/2006 | Pryor |
| 7,016,812 B2 | 3/2006 | Aritsuka et al. |
| 7,020,508 B2 | 3/2006 | Stivoric et al. |
| 7,022,047 B2 | 4/2006 | Cohen et al. |
| 7,022,048 B1 | 4/2006 | Fernandez |
| 7,022,049 B2 | 4/2006 | Ryan et al. |
| 7,033,176 B2 | 4/2006 | Feldman |
| 7,035,936 B2 | 4/2006 | Fouquet |
| 7,041,049 B1 | 5/2006 | Raniere |
| 7,044,891 B1 | 5/2006 | Rivera |
| 7,051,049 B2 | 5/2006 | Samn |
| 7,056,265 B1 | 6/2006 | Shea |
| 7,060,006 B1 | 6/2006 | Watterson et al. |
| 7,060,008 B2 | 6/2006 | Watterson et al. |
| 7,060,031 B2 | 6/2006 | Webb et al. |
| 7,063,644 B2 | 6/2006 | Albert et al. |
| 7,065,768 B1 | 6/2006 | Janzig et al. |
| 7,066,865 B2 | 6/2006 | Radow |
| 7,070,415 B2 | 7/2006 | Hojo et al. |
| 7,070,539 B2 | 7/2006 | Brown et al. |
| 7,070,542 B2 | 7/2006 | Reyes et al. |
| 7,070,545 B2 | 7/2006 | Lull et al. |
| 7,072,789 B2 | 7/2006 | Vock et al. |
| 7,091,635 B1 | 8/2006 | Gilliland et al. |
| 7,094,184 B1 | 8/2006 | Chen et al. |
| 7,097,593 B2 | 8/2006 | Chang |
| 7,108,641 B2 | 9/2006 | Pertegaz-Esteban |
| 7,113,166 B1 | 9/2006 | Rosenberg et al. |
| 7,115,076 B2 | 10/2006 | Oglesby et al. |
| 7,121,980 B2 | 10/2006 | Chen |
| 7,128,692 B2 | 10/2006 | Black |
| 7,128,693 B2 | 10/2006 | Brown et al. |
| 7,139,835 B2 | 11/2006 | Fouquet et al. |
| 7,148,879 B2 | 12/2006 | Amento et al. |
| 7,151,214 B2 | 12/2006 | Barry |
| 7,156,808 B2 | 1/2007 | Quy |
| 7,156,809 B2 | 1/2007 | Quy |
| 7,158,938 B2 | 1/2007 | Labbe et al. |
| 7,163,489 B1 | 1/2007 | Nelson |
| 7,166,062 B1 | 1/2007 | Watterson et al. |
| 7,166,064 B2 | 1/2007 | Watterson et al. |
| 7,169,093 B2 | 1/2007 | Simonson et al. |
| 7,170,016 B2 | 1/2007 | Dumornay |
| 7,171,331 B2 | 1/2007 | Vock et al. |
| 7,182,738 B2 | 2/2007 | Bonutti et al. |
| 7,187,961 B2 | 3/2007 | Yamashita et al. |
| 7,188,439 B2 | 3/2007 | DiBenedetto et al. |
| 7,192,387 B2 | 3/2007 | Mendel |
| 7,197,029 B1 | 3/2007 | Osterhout et al. |
| 7,200,517 B2 | 4/2007 | Darley et al. |
| 7,207,930 B2 | 4/2007 | Bonutti |
| 7,217,224 B2 | 5/2007 | Thomas |
| 7,220,219 B2 | 5/2007 | Papadopoulos et al. |
| 7,223,213 B2 | 5/2007 | Golesh |
| 7,224,326 B2 | 5/2007 | Sefton |
| 7,225,282 B1 | 5/2007 | Lyle |
| 7,225,565 B2 | 6/2007 | DiBenedetto et al. |
| 7,236,154 B1 | 6/2007 | Kerr et al. |
| 7,250,022 B2 | 7/2007 | Dalebout |
| 7,254,516 B2 | 8/2007 | Case, Jr. et al. |
| 7,257,468 B1 | 8/2007 | Costa et al. |
| 7,259,906 B1 | 8/2007 | Islam |
| 7,264,554 B2 | 9/2007 | Bentley |
| 7,278,955 B2 | 10/2007 | Giannelli et al. |
| 7,278,966 B2 | 10/2007 | Hjelt et al. |
| 7,285,090 B2 | 10/2007 | Stivoric et al. |
| 7,292,151 B2 | 11/2007 | Ferguson |
| 7,294,095 B2 | 11/2007 | Charnitski |
| 7,303,508 B2 | 12/2007 | Toyama et al. |
| 7,303,510 B2 | 12/2007 | Gebhardt |
| 7,308,818 B2 | 12/2007 | Considine et al. |
| 7,319,457 B2 | 1/2008 | Lin et al. |
| 7,322,907 B2 | 1/2008 | Bowser |
| 7,328,119 B1 | 2/2008 | Pryor |
| 7,329,684 B2 | 2/2008 | Mjalli et al. |
| 7,336,178 B2 | 2/2008 | Le |
| 7,350,787 B2 | 4/2008 | Voss |
| 7,351,187 B2 | 4/2008 | Seliber |
| 7,352,365 B2 | 4/2008 | Trachte |
| 7,354,380 B2 | 4/2008 | Volpe, Jr. |
| 7,357,756 B2 | 4/2008 | Demas |
| 7,365,647 B2 | 4/2008 | Nativ |
| 7,367,926 B2 | 5/2008 | Clark |
| 7,369,121 B2 | 5/2008 | Lane |
| 7,372,485 B1 | 5/2008 | Bodnar et al. |
| 7,373,820 B1 | 5/2008 | James |
| 7,374,519 B2 | 5/2008 | Naidus |
| 7,374,522 B2 | 5/2008 | Arnold |
| 7,383,081 B2 | 6/2008 | Butt et al. |
| 7,398,151 B1 | 7/2008 | Burrell et al. |
| 7,401,918 B2 | 7/2008 | Howell et al. |
| 7,402,125 B2 | 7/2008 | Wang |
| 7,412,206 B1 | 8/2008 | Hutchings et al. |
| 7,416,537 B1 | 8/2008 | Stark et al. |
| 7,418,862 B2 | 9/2008 | Gruben et al. |
| 7,432,184 B2 | 10/2008 | Hosokawa et al. |
| 7,432,454 B1 | 10/2008 | Sze et al. |
| 7,435,202 B2 | 10/2008 | Daly et al. |
| 7,452,336 B2 | 11/2008 | Thompson |
| 7,454,002 B1 | 11/2008 | Gardner et al. |
| 7,455,621 B1 | 11/2008 | Anthony |
| 7,455,622 B2 | 11/2008 | Watterson et al. |
| 7,455,626 B2 | 11/2008 | Trevino et al. |
| 7,462,141 B1 | 12/2008 | Raboin et al. |
| 7,465,257 B1 | 12/2008 | Morgan, Jr. |
| 7,477,890 B1 | 1/2009 | Narayanaswami |
| 7,480,512 B2 | 1/2009 | Graham et al. |
| 7,489,979 B2 | 2/2009 | Rosenberg |
| 7,491,159 B2 | 2/2009 | Patterson |
| 7,494,450 B2 | 2/2009 | Solomon |
| 7,503,476 B2 | 3/2009 | Bhavnani |
| 7,503,878 B1 | 3/2009 | Amsbury et al. |
| 7,507,183 B2 | 3/2009 | Anderson |
| 7,507,187 B2 | 3/2009 | Dyer et al. |
| 7,507,190 B2 | 3/2009 | Piane, Jr. |
| 7,510,509 B2 | 3/2009 | Hickman |
| 7,519,327 B2 | 4/2009 | White |

(56) References Cited

U.S. PATENT DOCUMENTS

| | | |
|---|---|---|
| 7,519,537 B2 | 4/2009 | Rosenberg |
| 7,521,623 B2 | 4/2009 | Bowen |
| 7,532,977 B2 | 5/2009 | Chen |
| 7,534,206 B1 | 5/2009 | Lovitt et al. |
| 7,537,546 B2 | 5/2009 | Watterson et al. |
| 7,537,549 B2 | 5/2009 | Nelson et al. |
| 7,537,552 B2 | 5/2009 | Dalebout et al. |
| 7,539,487 B2 | 5/2009 | Sinclair et al. |
| 7,542,816 B2 | 6/2009 | Rosenberg |
| 7,543,934 B2 | 6/2009 | Howell et al. |
| 7,549,947 B2 | 6/2009 | Hickman et al. |
| 7,553,260 B2 | 6/2009 | Piaget et al. |
| 7,556,590 B2 | 7/2009 | Watterson et al. |
| 7,561,989 B2 | 7/2009 | Banks et al. |
| 7,562,117 B2 | 7/2009 | Rosenberg |
| 7,575,536 B1 | 8/2009 | Hickman |
| 7,575,538 B1 | 8/2009 | Clark |
| 7,577,522 B2 | 8/2009 | Rosenberg |
| 7,579,946 B2 | 8/2009 | Case, Jr. |
| 7,585,251 B2 | 9/2009 | Doody, Jr. et al. |
| 7,585,254 B1 | 9/2009 | Vittone |
| 7,585,258 B2 | 9/2009 | Watson et al. |
| 7,586,032 B2 | 9/2009 | Louis |
| 7,591,795 B2 | 9/2009 | Whalen et al. |
| 7,598,255 B2 | 10/2009 | Dvorak |
| 7,601,096 B2 | 10/2009 | Negrin |
| 7,601,097 B2 | 10/2009 | Miyamaru et al. |
| 7,602,301 B1 | 10/2009 | Stirling et al. |
| 7,603,255 B2 | 10/2009 | Case, Jr. et al. |
| 7,607,243 B2 | 10/2009 | Berner, Jr. et al. |
| 7,616,097 B1 | 11/2009 | Whang |
| 7,618,345 B2 | 11/2009 | Corbalis et al. |
| 7,618,346 B2 | 11/2009 | Crawford et al. |
| 7,618,350 B2 | 11/2009 | Dalebout et al. |
| 7,619,514 B1 | 11/2009 | Stone |
| 7,621,850 B2 | 11/2009 | Piaget et al. |
| 7,625,314 B2 | 12/2009 | Ungari |
| 7,625,315 B2 | 12/2009 | Hickman |
| 7,625,316 B1 | 12/2009 | Amsbury et al. |
| 7,628,730 B1 | 12/2009 | Watterson et al. |
| 7,628,737 B2 | 12/2009 | Kowallis et al. |
| 7,631,382 B2 | 12/2009 | DiBenedetto et al. |
| 7,637,847 B1 | 12/2009 | Hickman |
| 7,641,592 B2 | 1/2010 | Roche |
| 7,643,895 B2 | 1/2010 | Gupta et al. |
| 7,645,212 B2 | 1/2010 | Ashby et al. |
| 7,645,213 B2 | 1/2010 | Watterson |
| 7,647,196 B2 | 1/2010 | Kahn et al. |
| 7,648,443 B2 | 1/2010 | Schenk |
| 7,648,446 B2 | 1/2010 | Chiles et al. |
| 7,648,463 B1 | 1/2010 | Elhag et al. |
| 7,648,858 B2 | 1/2010 | Tang et al. |
| 7,651,442 B2 | 1/2010 | Carlson |
| 7,654,229 B2 | 2/2010 | Smith |
| 7,654,948 B2 | 2/2010 | Kaplan et al. |
| 7,658,695 B1 | 2/2010 | Amsbury et al. |
| 7,662,065 B1 | 2/2010 | Kahn et al. |
| 7,662,282 B2 | 2/2010 | Lee et al. |
| 7,670,263 B2 | 3/2010 | Ellis |
| 7,676,332 B2 | 3/2010 | Damen |
| 7,677,723 B2 | 3/2010 | Howell et al. |
| 7,678,023 B1 | 3/2010 | Shea |
| 7,682,286 B2 | 3/2010 | Badarneh et al. |
| 7,683,252 B2 | 3/2010 | Oliver et al. |
| 7,689,437 B1 | 3/2010 | Teller et al. |
| 7,690,556 B1 | 4/2010 | Kahn et al. |
| 7,698,101 B2 | 4/2010 | Alten et al. |
| 7,698,359 B1 | 4/2010 | Wray et al. |
| 7,699,752 B1 | 4/2010 | Anderson |
| 7,699,753 B2 | 4/2010 | Daikeler |
| 7,699,754 B2 | 4/2010 | Schneider |
| 7,699,755 B2 | 4/2010 | Feldman et al. |
| 7,702,781 B2 | 4/2010 | Devolites |
| 7,703,974 B2 | 4/2010 | Bouille |
| 7,704,192 B2 | 4/2010 | Dyer et al. |
| 7,705,230 B2 | 4/2010 | Bowen |
| 7,713,171 B1 | 5/2010 | Hickman |
| 7,717,825 B2 | 5/2010 | Van Der Hoeven |
| 7,717,827 B2 | 5/2010 | Kurunmäki et al. |
| 7,717,866 B2 | 5/2010 | Damen |
| 7,722,503 B1 | 5/2010 | Smith et al. |
| 7,725,362 B2 | 5/2010 | Weathers, Jr. |
| 7,727,117 B2 | 6/2010 | Feldman et al. |
| 7,727,125 B2 | 6/2010 | Day |
| 7,728,214 B2 | 6/2010 | Oliver et al. |
| 7,736,272 B2 | 6/2010 | Martens |
| 7,739,076 B1 | 6/2010 | Vock et al. |
| 7,740,562 B2 | 6/2010 | Jones |
| 7,740,588 B1 | 6/2010 | Sciarra |
| 7,745,716 B1 | 6/2010 | Murphy |
| 7,747,671 B2 | 6/2010 | Ku |
| 7,749,137 B2 | 7/2010 | Watt et al. |
| 7,753,824 B2 | 7/2010 | Wang |
| 7,753,825 B2 | 7/2010 | Jaquish et al. |
| 7,753,861 B1 | 7/2010 | Kahn et al. |
| 7,758,469 B2 | 7/2010 | Dyer et al. |
| 7,758,523 B2 | 7/2010 | Collings et al. |
| 7,761,300 B2 | 7/2010 | Klingler |
| 7,762,931 B2 | 7/2010 | Fisher et al. |
| 7,762,934 B1 | 7/2010 | Munson, Jr. et al. |
| 7,764,990 B2 | 7/2010 | Martikka et al. |
| 7,765,348 B2 | 7/2010 | Dybsetter |
| 7,766,794 B2 | 8/2010 | Oliver et al. |
| 7,766,798 B2 | 8/2010 | Hamilton |
| 7,770,181 B2 | 8/2010 | Snover et al. |
| 7,771,319 B1 | 8/2010 | Lannon |
| 7,771,320 B2 | 8/2010 | Riley et al. |
| 7,771,325 B2 | 8/2010 | Baker |
| 7,771,329 B2 | 8/2010 | Dalebout et al. |
| 7,775,128 B2 | 8/2010 | Roessingh et al. |
| 7,775,936 B2 | 8/2010 | Wilkinson |
| 7,789,800 B1 | 9/2010 | Watterson et al. |
| 7,794,014 B2 | 9/2010 | Beall et al. |
| 7,798,942 B2 | 9/2010 | Digiulio |
| 7,805,149 B2 | 9/2010 | Werner et al. |
| 7,806,806 B2 | 10/2010 | Jaquish |
| 7,806,815 B2 | 10/2010 | Fernandez |
| 7,809,153 B2 | 10/2010 | Bravomalo et al. |
| 7,811,200 B2 | 10/2010 | Chiang |
| 7,811,201 B1 | 10/2010 | Mikan et al. |
| 7,813,715 B2 | 10/2010 | McKillop et al. |
| 7,815,549 B2 | 10/2010 | Crawford et al. |
| 7,822,547 B2 | 10/2010 | Lindroos |
| 7,825,319 B2 | 11/2010 | Turner |
| 7,827,000 B2 | 11/2010 | Stirling et al. |
| 7,830,570 B2 | 11/2010 | Morita et al. |
| 7,833,129 B2 | 11/2010 | Badarneh |
| 7,833,135 B2 | 11/2010 | Radow |
| 7,837,595 B2 | 11/2010 | Rice |
| 7,837,596 B2 | 11/2010 | Astilean |
| 7,837,599 B2 | 11/2010 | Kowalczewski et al. |
| 7,839,058 B1 | 11/2010 | Churchill et al. |
| 7,840,346 B2 | 11/2010 | Huhtala et al. |
| 7,841,967 B1 | 11/2010 | Kahn |
| 7,846,067 B2 | 12/2010 | Hanoun |
| 7,846,080 B2 | 12/2010 | Boren |
| 7,857,731 B2 | 12/2010 | Hickman et al. |
| 7,857,732 B2 | 12/2010 | Nielson |
| 7,862,476 B2 | 1/2011 | Radow |
| 7,862,478 B2 | 1/2011 | Watterson et al. |
| 7,862,483 B2 | 1/2011 | Hendrickson et al. |
| 7,867,088 B2 | 1/2011 | Prum |
| 7,874,957 B2 | 1/2011 | Hurwitz et al. |
| 7,894,177 B2 | 2/2011 | Rothkopf |
| 7,894,849 B2 | 2/2011 | Kass et al. |
| 7,896,782 B2 | 3/2011 | Tamari |
| 7,901,292 B1 | 3/2011 | Uhlir et al. |
| 7,901,323 B2 | 3/2011 | Olason et al. |
| 7,901,325 B2 | 3/2011 | Henderson |
| 7,909,741 B2 | 3/2011 | Kim et al. |
| 7,913,297 B2 | 3/2011 | Wyld |
| 7,914,421 B2 | 3/2011 | Weier et al. |
| 7,914,425 B2 | 3/2011 | Hanoun |
| 7,914,468 B2 | 3/2011 | Shalon et al. |

(56) References Cited

U.S. PATENT DOCUMENTS

| | | |
|---|---|---|
| 7,917,148 B2 | 3/2011 | Rosenberg |
| 7,918,732 B2 | 4/2011 | Van Noland |
| 7,922,635 B2 | 4/2011 | Lull et al. |
| 7,927,253 B2 | 4/2011 | Vincent |
| 7,927,258 B2 | 4/2011 | Irving et al. |
| 7,931,563 B2 | 4/2011 | Shaw et al. |
| 7,934,983 B1 | 5/2011 | Eisner |
| 7,938,752 B1 | 5/2011 | Wang |
| 7,946,959 B2 | 5/2011 | Shum et al. |
| 7,946,961 B2 | 5/2011 | Blum et al. |
| 7,949,295 B2 | 5/2011 | Kumar et al. |
| 7,950,297 B2 | 5/2011 | Moore et al. |
| 7,951,046 B1 | 5/2011 | Barber, Jr. |
| 7,953,549 B2 | 5/2011 | Graham et al. |
| 7,955,219 B2 | 6/2011 | Birrell et al. |
| 7,959,567 B2 | 6/2011 | Stivoric et al. |
| 7,963,889 B2 | 6/2011 | Badarneh et al. |
| 7,967,728 B2 | 6/2011 | Zavadsky |
| 7,968,574 B2 | 6/2011 | Hangauer, Jr. |
| 7,972,245 B2 | 7/2011 | Temple et al. |
| 7,972,247 B2 | 7/2011 | Daikeler |
| 7,972,249 B1 | 7/2011 | Napalan |
| 7,973,231 B2 | 7/2011 | Bowen |
| 7,974,889 B2 | 7/2011 | Raimbeault |
| 7,976,518 B2 | 7/2011 | Shaughnessy et al. |
| 7,978,081 B2 | 7/2011 | Shears et al. |
| 7,980,996 B2 | 7/2011 | Hickman |
| 7,981,000 B2 | 7/2011 | Watterson et al. |
| 7,988,598 B2 | 8/2011 | Trzecieski |
| 7,988,599 B2 | 8/2011 | Ainsworth et al. |
| 8,001,472 B2 | 8/2011 | Gilley et al. |
| 8,002,671 B1 | 8/2011 | Vigilia |
| RE42,698 E | 9/2011 | Kuo et al. |
| 8,012,064 B2 | 9/2011 | Martens |
| 8,012,073 B2 | 9/2011 | Barnett |
| 8,021,270 B2 | 9/2011 | D Eredita |
| 8,021,277 B2 | 9/2011 | Baudhuin |
| 8,025,607 B2 | 9/2011 | Ranky et al. |
| 8,025,612 B1 | 9/2011 | Buzzanco |
| 8,028,443 B2 | 10/2011 | Case, Jr. |
| 8,029,415 B2 | 10/2011 | Ashby et al. |
| 8,033,959 B2 | 10/2011 | Oleson et al. |
| 8,034,294 B1 | 10/2011 | Goldberg |
| 8,037,017 B2 | 10/2011 | Samn |
| 8,038,577 B2 | 10/2011 | Mcintosh |
| 8,040,758 B1 | 10/2011 | Dickinson |
| 8,043,173 B2 | 10/2011 | Menalagha et al. |
| 8,046,803 B1 | 10/2011 | Lee |
| 8,047,965 B2 | 11/2011 | Shea |
| 8,047,966 B2 | 11/2011 | Dorogusker et al. |
| 8,052,580 B2 | 11/2011 | Saalasti et al. |
| 8,052,584 B2 | 11/2011 | Keiser |
| 8,056,687 B2 | 11/2011 | Golden et al. |
| 8,057,360 B2 | 11/2011 | Shea |
| 8,062,182 B2 | 11/2011 | Somers |
| 8,062,192 B1 | 11/2011 | Arstein |
| 8,065,185 B2 | 11/2011 | Foladare et al. |
| 8,066,514 B2 | 11/2011 | Clarke |
| 8,070,655 B1 | 12/2011 | Napolitano |
| 8,073,304 B2 | 12/2011 | Rohlicek |
| 8,075,453 B1 | 12/2011 | Wilkinson |
| 8,078,426 B2 | 12/2011 | Pipinich et al. |
| 8,083,643 B2 | 12/2011 | Ng et al. |
| 8,086,421 B2 | 12/2011 | Case, Jr. et al. |
| 8,088,043 B2 | 1/2012 | Andren et al. |
| 8,088,044 B2 | 1/2012 | Tchao et al. |
| 8,092,381 B2 | 1/2012 | Edwards |
| 8,101,843 B2 | 1/2012 | Turner |
| 8,103,517 B2 | 1/2012 | Hinnebusch |
| 8,105,207 B1 | 1/2012 | Lannon |
| 8,106,563 B2 | 1/2012 | Stengel et al. |
| 8,109,858 B2 | 2/2012 | Redmann |
| 8,112,281 B2 | 2/2012 | Yeung et al. |
| 8,113,990 B2 | 2/2012 | Kolman et al. |
| 8,113,991 B2 | 2/2012 | Kutliroff |
| 8,116,841 B2 | 2/2012 | Bly et al. |
| 8,121,785 B2 | 2/2012 | Swisher et al. |
| 8,123,527 B2 | 2/2012 | Holljes |
| 8,128,533 B2 | 3/2012 | Nakagawa et al. |
| 8,142,298 B2 | 3/2012 | King et al. |
| 8,142,370 B2 | 3/2012 | Weinberg et al. |
| 8,152,693 B2 | 4/2012 | Nurmela et al. |
| 8,152,695 B2 | 4/2012 | Riley et al. |
| 8,157,706 B2 | 4/2012 | Ainsworth et al. |
| 8,157,731 B2 | 4/2012 | Teller et al. |
| 8,162,804 B2 | 4/2012 | Tagliabue |
| 8,162,857 B2 | 4/2012 | Lanfermann et al. |
| 8,165,893 B1 | 4/2012 | Goldberg et al. |
| 8,167,776 B2 | 5/2012 | Lannon |
| 8,172,723 B1 | 5/2012 | Yanev et al. |
| 8,172,882 B2 | 5/2012 | Klyce et al. |
| 8,176,101 B2 | 5/2012 | Rosenberg |
| 8,177,611 B2 | 5/2012 | Kang |
| 8,177,688 B2 | 5/2012 | Burnfield et al. |
| 8,188,868 B2 | 5/2012 | Case, Jr. |
| 8,192,332 B2 | 6/2012 | Baker et al. |
| 8,200,323 B2 | 6/2012 | Dibenedetto et al. |
| 8,213,908 B2 | 7/2012 | Sangster et al. |
| 8,221,290 B2 | 7/2012 | Vincent et al. |
| 8,221,292 B2 | 7/2012 | Barker et al. |
| 8,224,429 B2 | 7/2012 | Prstojevich et al. |
| 8,225,024 B2 | 7/2012 | Dybsetter |
| 8,231,506 B2 | 7/2012 | Molyneux et al. |
| 8,235,724 B2 | 8/2012 | Gilley et al. |
| 8,241,118 B2 | 8/2012 | Camhi |
| 8,241,186 B2 | 8/2012 | Brodess et al. |
| 8,249,686 B2 | 8/2012 | Libbus et al. |
| 8,251,874 B2 | 8/2012 | Ashby et al. |
| 8,253,586 B1 | 8/2012 | Matak |
| 8,257,228 B2 | 9/2012 | Quatrochi et al. |
| 8,260,667 B2 | 9/2012 | Graham et al. |
| 8,260,858 B2 | 9/2012 | Belz et al. |
| 8,269,093 B2 | 9/2012 | Naik et al. |
| 8,272,996 B2 | 9/2012 | Weier |
| 8,275,143 B2 | 9/2012 | Johnson |
| 8,275,265 B2 | 9/2012 | Kobyakov et al. |
| 8,276,434 B2 | 10/2012 | Senoo |
| 8,280,259 B2 | 10/2012 | George et al. |
| 8,287,434 B2 | 10/2012 | Zavadsky et al. |
| 8,296,172 B2 | 10/2012 | Marci et al. |
| 8,298,123 B2 | 10/2012 | Hickman |
| 8,306,635 B2 | 11/2012 | Pryor |
| 8,308,794 B2 | 11/2012 | Martinson et al. |
| 8,314,840 B1 | 11/2012 | Funk |
| 8,315,823 B2 | 11/2012 | Berme et al. |
| 8,321,004 B2 | 11/2012 | Moon et al. |
| 8,332,544 B1 | 12/2012 | Ralls et al. |
| 8,337,335 B2 | 12/2012 | Dugan |
| 8,341,557 B2 | 12/2012 | Pisula et al. |
| 8,348,840 B2 | 1/2013 | Heit et al. |
| 8,360,785 B2 | 1/2013 | Park et al. |
| 8,360,904 B2 | 1/2013 | Oleson et al. |
| 8,360,935 B2 | 1/2013 | Olsen et al. |
| 8,360,936 B2 | 1/2013 | Dibenedetto et al. |
| 8,363,913 B2 | 1/2013 | Boushey et al. |
| 8,364,250 B2 | 1/2013 | Moon et al. |
| 8,364,389 B2 | 1/2013 | Dorogusker et al. |
| 8,369,936 B2 | 2/2013 | Farringdon et al. |
| 8,371,990 B2 | 2/2013 | Shea |
| 8,374,688 B2 | 2/2013 | Libbus et al. |
| 8,376,910 B2 | 2/2013 | Cheung et al. |
| 8,384,551 B2 | 2/2013 | Ross et al. |
| 8,398,546 B2 | 3/2013 | Pacione et al. |
| 8,403,845 B2 | 3/2013 | Stivoric et al. |
| 8,407,623 B2 | 3/2013 | Kerr et al. |
| 8,412,317 B2 | 4/2013 | Mazar |
| 8,419,593 B2 | 4/2013 | Ainsworth et al. |
| 8,429,223 B2 | 4/2013 | Gilley et al. |
| 8,430,770 B2 | 4/2013 | Dugan |
| 8,437,824 B2 | 5/2013 | Moon et al. |
| 8,446,275 B2 | 5/2013 | Utter, II |
| 8,452,259 B2 | 5/2013 | Ellis et al. |
| 8,454,437 B2 | 6/2013 | Dugan |
| 8,460,001 B1 | 6/2013 | Chuang |

(56) References Cited

U.S. PATENT DOCUMENTS

| | | |
|---|---|---|
| 8,460,189 B2 | 6/2013 | Libbus et al. |
| 8,475,338 B2 | 7/2013 | Greenhill et al. |
| 8,475,367 B1 | 7/2013 | Yuen et al. |
| 8,475,370 B2 | 7/2013 | McCombie et al. |
| 8,480,541 B1 | 7/2013 | Brunts |
| 8,485,982 B2 | 7/2013 | Gavish et al. |
| 8,485,996 B2 | 7/2013 | Bluman |
| 8,491,446 B2 | 7/2013 | Hinds et al. |
| 8,491,572 B2 | 7/2013 | Martinson et al. |
| 8,493,822 B2 | 7/2013 | Lee et al. |
| 8,503,086 B2 | 8/2013 | French et al. |
| 8,506,457 B2 | 8/2013 | Baudhuin |
| 8,506,458 B2 | 8/2013 | Dugan |
| 8,515,930 B2 | 8/2013 | Hong |
| 8,517,896 B2 | 8/2013 | Robinette et al. |
| 8,517,899 B2 | 8/2013 | Zhou |
| 8,523,789 B2 | 9/2013 | Keiser |
| 8,527,038 B2 | 9/2013 | Moon et al. |
| 8,529,409 B1 | 9/2013 | Lesea-Ames |
| 8,531,386 B1 | 9/2013 | Kerr et al. |
| 8,533,007 B2 | 9/2013 | Egami et al. |
| 8,533,620 B2 | 9/2013 | Hoffman et al. |
| 8,538,333 B2 | 9/2013 | Jain et al. |
| 8,538,723 B2 | 9/2013 | Chang |
| 8,540,641 B2 | 9/2013 | Kroll et al. |
| 8,543,185 B2 | 9/2013 | Yuen et al. |
| 8,545,417 B2 | 10/2013 | Banet et al. |
| 8,554,214 B2 | 10/2013 | Sweeney et al. |
| 8,554,802 B1 | 10/2013 | Barden et al. |
| 8,556,778 B1 | 10/2013 | Dugan |
| 8,560,951 B1 | 10/2013 | Snyder et al. |
| 8,562,489 B2 | 10/2013 | Burton et al. |
| 8,568,277 B2 | 10/2013 | Johnson |
| 8,568,278 B2 | 10/2013 | Riley et al. |
| 8,571,880 B2 | 10/2013 | Goldberg |
| 8,572,576 B2 | 10/2013 | Elvanoglu et al. |
| 8,579,767 B2 | 11/2013 | Ellis et al. |
| 8,591,411 B2 | 11/2013 | Banet et al. |
| 8,594,772 B2 | 11/2013 | Eggenberger et al. |
| RE44,650 E | 12/2013 | Anderson |
| 8,597,093 B2 | 12/2013 | Engelberg et al. |
| 8,602,997 B2 | 12/2013 | Banet et al. |
| 8,605,048 B2 | 12/2013 | Ye et al. |
| 8,610,593 B2 | 12/2013 | Van Acht et al. |
| 8,613,689 B2 | 12/2013 | Dyer et al. |
| 8,622,873 B2 | 1/2014 | Mcgown |
| 8,628,333 B2 | 1/2014 | Prinzel, III et al. |
| 8,628,453 B2 | 1/2014 | Balakrishnan et al. |
| 8,639,020 B1 | 1/2014 | Kutliroff et al. |
| 8,647,240 B2 | 2/2014 | Heidecke |
| 8,649,890 B2 | 2/2014 | Martin |
| 8,652,010 B2 | 2/2014 | Ellis et al. |
| 8,654,198 B2 | 2/2014 | Pryor |
| 8,655,004 B2 | 2/2014 | Prest et al. |
| 8,662,901 B2 | 3/2014 | Tzao et al. |
| 8,663,106 B2 | 3/2014 | Stivoric et al. |
| 8,667,194 B2 | 3/2014 | Dybsetter et al. |
| 8,670,222 B2 | 3/2014 | Rothkopf |
| 8,672,852 B2 | 3/2014 | Gavish |
| 8,676,170 B2 | 3/2014 | Porrati et al. |
| 8,676,541 B2 | 3/2014 | Schrock et al. |
| 8,678,979 B2 | 3/2014 | Stark et al. |
| 8,684,925 B2 | 4/2014 | Manicka et al. |
| 8,690,578 B1 | 4/2014 | Nusbaum et al. |
| 8,690,735 B2 | 4/2014 | Watterson et al. |
| 8,702,430 B2 | 4/2014 | Dibenedetto et al. |
| 8,704,068 B2 | 4/2014 | Bowen |
| 8,706,530 B2 | 4/2014 | Ohnemus et al. |
| 8,708,842 B2 | 4/2014 | Ganuza |
| 8,712,510 B2 | 4/2014 | Quy |
| 8,718,752 B2 | 5/2014 | Libbus et al. |
| 8,719,202 B1 | 5/2014 | Maeng |
| 8,727,947 B2 | 5/2014 | Tagliabue |
| 8,734,157 B1 | 5/2014 | Hummel, III |
| 8,734,296 B1 | 5/2014 | Brumback et al. |
| 8,734,301 B2 | 5/2014 | Remelius |
| 8,738,732 B2 | 5/2014 | Karidi |
| 8,740,751 B2 | 6/2014 | Shum |
| 8,740,802 B2 | 6/2014 | Banet et al. |
| 8,740,807 B2 | 6/2014 | Banet et al. |
| 8,744,803 B2 | 6/2014 | Park et al. |
| 8,745,104 B1 | 6/2014 | Rosenberg |
| 8,745,496 B2 | 6/2014 | Gilley et al. |
| 8,747,330 B2 | 6/2014 | Banet et al. |
| 8,749,380 B2 | 6/2014 | Vock et al. |
| 8,758,201 B2 | 6/2014 | Ashby et al. |
| 8,762,101 B2 | 6/2014 | Yuen et al. |
| 8,762,167 B2 | 6/2014 | Blander et al. |
| 8,762,313 B2 | 6/2014 | Lahav et al. |
| 8,764,609 B1 | 7/2014 | Elahmadie |
| 8,764,651 B2 | 7/2014 | Tran |
| 8,768,769 B2 | 7/2014 | Foladare et al. |
| 8,770,742 B2 | 7/2014 | Howell et al. |
| 8,771,206 B2 | 7/2014 | Gettelman et al. |
| 8,775,454 B2 | 7/2014 | Geer |
| 8,776,264 B2 | 7/2014 | Kiernan |
| 8,777,815 B2 | 7/2014 | Case, Jr. et al. |
| 8,781,568 B2 | 7/2014 | Dugan |
| 8,784,271 B2 | 7/2014 | Brumback et al. |
| 8,784,273 B2 | 7/2014 | Dugan |
| 8,790,220 B2 | 7/2014 | Karvonen |
| 8,790,259 B2 | 7/2014 | Katra et al. |
| 8,795,138 B1 | 8/2014 | Yeh et al. |
| 8,799,200 B2 | 8/2014 | Lahav |
| 8,805,844 B2 | 8/2014 | Schorzman et al. |
| 8,805,941 B2 | 8/2014 | Barak et al. |
| 8,814,754 B2 | 8/2014 | Weast et al. |
| 8,821,350 B2 | 9/2014 | Maertz |
| 8,821,351 B2 | 9/2014 | Abuelsaad et al. |
| 8,825,445 B2 | 9/2014 | Hoffman et al. |
| 8,827,870 B2 | 9/2014 | Dyer et al. |
| 8,831,407 B2 | 9/2014 | Meschter et al. |
| 8,831,538 B2 | 9/2014 | Yuen |
| 8,838,471 B1 | 9/2014 | Shum et al. |
| 8,845,497 B2 | 9/2014 | Turner |
| 8,847,988 B2 | 9/2014 | Geisner et al. |
| 8,861,860 B2 | 10/2014 | Gupta |
| 8,864,587 B2 | 10/2014 | Framel et al. |
| 8,868,448 B2 | 10/2014 | Freishtat et al. |
| 8,870,791 B2 | 10/2014 | Sabatino |
| 8,882,637 B2 | 11/2014 | Ainsworth et al. |
| 8,882,666 B1 | 11/2014 | Goldberg et al. |
| 8,888,583 B2 | 11/2014 | Dugan et al. |
| 8,888,700 B2 | 11/2014 | Banet et al. |
| 8,897,868 B2 | 11/2014 | Mazar et al. |
| 8,900,099 B1 | 12/2014 | Boyette |
| 8,902,714 B2 | 12/2014 | Gossweiler, III et al. |
| 8,903,671 B2 | 12/2014 | Park et al. |
| 8,908,894 B2 | 12/2014 | Amento et al. |
| 8,915,823 B2 | 12/2014 | McKirdy et al. |
| 8,918,465 B2 | 12/2014 | Barak |
| 8,918,543 B2 | 12/2014 | Karstens |
| 8,920,332 B2 | 12/2014 | Hong et al. |
| 8,920,343 B2 | 12/2014 | Sabatino |
| 8,926,475 B2 | 1/2015 | Lin et al. |
| 8,939,831 B2 | 1/2015 | Dugan |
| 8,943,002 B2 | 1/2015 | Zelenko et al. |
| 8,944,958 B1 | 2/2015 | Brumback et al. |
| 8,944,968 B2 | 2/2015 | Baudhuin |
| 8,945,328 B2 | 2/2015 | Longinotti-Buitoni et al. |
| 8,947,226 B2 | 2/2015 | Dugan |
| 8,951,106 B2 | 2/2015 | Crowley |
| 8,951,164 B2 | 2/2015 | Morris et al. |
| 8,951,168 B2 | 2/2015 | Baudhuin |
| 8,954,135 B2 | 2/2015 | Yuen et al. |
| 8,954,290 B2 | 2/2015 | Yuen et al. |
| 8,956,268 B2 | 2/2015 | Huang et al. |
| 8,956,290 B2 | 2/2015 | Gilley et al. |
| 8,956,303 B2 | 2/2015 | Hong et al. |
| 8,958,631 B2 | 2/2015 | Kutliroff et al. |
| 8,961,371 B2 | 2/2015 | Sultan et al. |
| 8,961,413 B2 | 2/2015 | Teller et al. |
| 8,961,414 B2 | 2/2015 | Teller et al. |
| 8,965,348 B1 | 2/2015 | Cronin |

(56) References Cited

U.S. PATENT DOCUMENTS

| | | |
|---|---|---|
| 8,965,498 B2 | 2/2015 | Katra et al. |
| 8,965,541 B2 | 2/2015 | Martinez et al. |
| 8,965,732 B2 | 2/2015 | Robinette et al. |
| 8,968,161 B2 | 3/2015 | Shapiro et al. |
| 8,972,199 B2 | 3/2015 | Liang |
| 8,976,007 B2 | 3/2015 | Dugan |
| 8,977,194 B2 | 3/2015 | Jain et al. |
| 8,979,765 B2 | 3/2015 | Banet et al. |
| 8,992,383 B2 | 3/2015 | Bilang |
| 8,992,387 B2 | 3/2015 | Watterson et al. |
| 9,005,129 B2 | 4/2015 | Venkatraman et al. |
| 9,011,291 B2 | 4/2015 | Birrell |
| 9,011,292 B2 | 4/2015 | Weast et al. |
| 9,011,293 B2 | 4/2015 | Shavit et al. |
| 9,011,301 B2 | 4/2015 | Balandis et al. |
| 9,017,230 B1 | 4/2015 | Pitts |
| 9,026,927 B2 | 5/2015 | Brumback et al. |
| 9,028,368 B2 | 5/2015 | Ashby et al. |
| 9,028,441 B2 | 5/2015 | Kuhn |
| 9,031,812 B2 | 5/2015 | Roberts et al. |
| 9,037,578 B2 | 5/2015 | Brust et al. |
| 9,039,581 B2 | 5/2015 | Chia et al. |
| 9,039,614 B2 | 5/2015 | Yuen et al. |
| 9,042,596 B2 | 5/2015 | Connor |
| 9,050,498 B2 | 6/2015 | Lu et al. |
| 9,052,798 B1 | 6/2015 | Klassen et al. |
| 9,055,868 B2 | 6/2015 | Islam |
| 9,064,342 B2 | 6/2015 | Yuen et al. |
| 9,069,380 B2 | 6/2015 | Rahman et al. |
| 9,072,930 B2 | 7/2015 | Ashby et al. |
| 9,083,826 B2 | 7/2015 | Lu et al. |
| 9,084,912 B2 | 7/2015 | Jaquish et al. |
| 9,089,733 B2 | 7/2015 | Fisbein et al. |
| 9,107,586 B2 | 8/2015 | Tran |
| 9,114,275 B2 | 8/2015 | Lu et al. |
| 9,119,983 B2 | 9/2015 | Rhea |
| 9,123,317 B2 | 9/2015 | Watterson et al. |
| 9,123,380 B2 | 9/2015 | Holtz et al. |
| 9,128,981 B1 | 9/2015 | Geer |
| 9,135,347 B2 | 9/2015 | Damman et al. |
| 9,137,309 B2 | 9/2015 | Ananny et al. |
| 9,138,614 B2 | 9/2015 | Lu et al. |
| 9,138,615 B2 | 9/2015 | Olson et al. |
| 9,141,087 B2 | 9/2015 | Brown et al. |
| 9,143,881 B2 | 9/2015 | Fan et al. |
| 9,144,709 B2 | 9/2015 | Reich |
| 9,146,147 B1 | 9/2015 | Bakhsh |
| 9,162,142 B2 | 10/2015 | Shum et al. |
| 9,168,001 B2 | 10/2015 | Stivoric et al. |
| 9,173,593 B2 | 11/2015 | Banet et al. |
| 9,173,594 B2 | 11/2015 | Banet et al. |
| 9,174,084 B2 | 11/2015 | Morris et al. |
| 9,174,085 B2 | 11/2015 | Foley |
| 9,178,635 B2 | 11/2015 | Ben-Shlomo |
| 9,183,498 B2 | 11/2015 | Landers |
| 9,186,549 B2 | 11/2015 | Watterson et al. |
| 9,189,021 B2 | 11/2015 | Jerauld |
| 9,192,816 B2 | 11/2015 | Molyneux et al. |
| 9,201,405 B2 | 12/2015 | Clarkson et al. |
| 9,205,301 B2 | 12/2015 | Cohen |
| 9,208,764 B2 | 12/2015 | Ghosh et al. |
| 9,211,440 B2 | 12/2015 | Lagree |
| 9,213,803 B2 | 12/2015 | Rolley |
| 9,223,936 B2 | 12/2015 | Aragones et al. |
| 9,224,291 B2 | 12/2015 | Moll-Carrillo et al. |
| 9,229,476 B2 | 1/2016 | Yanev et al. |
| 9,230,064 B2 | 1/2016 | Yanev et al. |
| 9,233,269 B2 | 1/2016 | Lannon |
| 9,241,635 B2 | 1/2016 | Yuen et al. |
| 9,245,428 B2 | 1/2016 | Weddle et al. |
| 9,247,543 B2 | 1/2016 | Berlin et al. |
| 9,253,168 B2 | 2/2016 | Panther |
| 9,254,099 B2 | 2/2016 | Connor |
| 9,256,910 B2 | 2/2016 | Goldberg |
| 9,257,054 B2 | 2/2016 | Coza et al. |
| 9,258,670 B2 | 2/2016 | Goyal et al. |
| 9,259,633 B2 | 2/2016 | Meyers |
| 9,262,064 B2 | 2/2016 | Yanev et al. |
| 9,269,119 B2 | 2/2016 | Warner |
| 9,272,183 B2 | 3/2016 | Quy |
| 9,272,186 B2 | 3/2016 | Reich |
| 9,275,617 B2 | 3/2016 | Regnier |
| 9,279,734 B2 | 3/2016 | Walker |
| 9,283,429 B2 | 3/2016 | Aragones et al. |
| 9,288,298 B2 | 3/2016 | Choudhary et al. |
| 9,295,422 B2 | 3/2016 | Tai |
| 9,295,894 B2 | 3/2016 | Papadopolous |
| 9,305,141 B2 | 4/2016 | Fabrizio |
| 9,317,662 B2 | 4/2016 | Bangera et al. |
| 9,318,030 B2 | 4/2016 | Harris et al. |
| 9,329,053 B2 | 5/2016 | Lakovic et al. |
| 9,332,363 B2 | 5/2016 | Jain et al. |
| 9,339,209 B2 | 5/2016 | Banet et al. |
| 9,339,691 B2 | 5/2016 | Brammer |
| 9,339,692 B2 | 5/2016 | Hashish |
| 9,345,947 B2 | 5/2016 | Harris et al. |
| 9,349,280 B2 | 5/2016 | Baldwin et al. |
| 9,350,598 B2 | 5/2016 | Barak et al. |
| 9,357,551 B2 | 5/2016 | Gutman |
| 9,357,921 B2 | 6/2016 | Chang et al. |
| 9,358,422 B2 | 6/2016 | Brontman |
| 9,358,426 B2 | 6/2016 | Aragones et al. |
| 9,364,158 B2 | 6/2016 | Banet et al. |
| 9,364,714 B2 | 6/2016 | Koduri et al. |
| 9,367,668 B2 | 6/2016 | Flynt et al. |
| 9,370,679 B2 | 6/2016 | Lagree et al. |
| 9,374,279 B2 | 6/2016 | Yuen et al. |
| 9,375,629 B2 | 6/2016 | Schieffer et al. |
| 9,377,314 B2 | 6/2016 | Tseng et al. |
| 9,378,336 B2 | 6/2016 | Ohnemus et al. |
| 9,381,420 B2 | 7/2016 | Burroughs |
| 9,381,445 B2 | 7/2016 | Ventura et al. |
| 9,385,810 B2 | 7/2016 | Hazani |
| 9,389,057 B2 | 7/2016 | Meschter et al. |
| 9,389,718 B1 | 7/2016 | Letourneur |
| 9,389,754 B2 | 7/2016 | Reese et al. |
| 9,390,229 B1 | 7/2016 | Kahn et al. |
| 9,392,941 B2 | 7/2016 | Powch et al. |
| 9,395,754 B2 | 7/2016 | Cronin |
| 9,401,078 B2 | 7/2016 | Barrett |
| 9,403,048 B2 | 8/2016 | Balandis et al. |
| 9,403,053 B2 | 8/2016 | Kaiser et al. |
| 9,405,892 B2 | 8/2016 | Baldwin et al. |
| 9,409,052 B2 | 8/2016 | Werner |
| 9,411,936 B2 | 8/2016 | Landrum et al. |
| 9,411,940 B2 | 8/2016 | Burroughs et al. |
| 9,420,083 B2 | 8/2016 | Roberts et al. |
| 9,420,542 B2 | 8/2016 | Henia |
| 9,421,422 B2 | 8/2016 | Yuen et al. |
| 9,421,448 B2 | 8/2016 | Tropper et al. |
| 9,422,018 B2 | 8/2016 | Pelot et al. |
| 9,430,043 B1 | 8/2016 | Amento et al. |
| 9,430,920 B2 | 8/2016 | Munro et al. |
| 9,439,574 B2 | 9/2016 | McCombie et al. |
| 9,440,134 B2 | 9/2016 | Nicora |
| 9,442,100 B2 | 9/2016 | Connor |
| 9,446,288 B1 | 9/2016 | Pazan |
| 9,451,897 B2 | 9/2016 | Mazar et al. |
| 9,452,320 B2 | 9/2016 | Yang |
| 9,455,784 B2 | 9/2016 | Cune et al. |
| 9,457,256 B2 | 10/2016 | Aragones et al. |
| 9,460,421 B2 | 10/2016 | Lai et al. |
| 9,462,844 B2 | 10/2016 | Schrock et al. |
| 9,463,572 B2 | 10/2016 | Parente |
| 9,468,382 B2 | 10/2016 | Hanoun |
| 9,468,793 B2 | 10/2016 | Salmon |
| 9,468,794 B2 | 10/2016 | Barton |
| 9,473,593 B2 | 10/2016 | Wallace |
| 9,474,925 B1 | 10/2016 | Hsiung |
| 9,474,935 B2 | 10/2016 | Abbondanza et al. |
| 9,477,303 B2 | 10/2016 | Fleischmann et al. |
| 9,486,070 B2 | 11/2016 | Labrosse et al. |
| 9,486,382 B1 | 11/2016 | Boss |
| 9,491,562 B2 | 11/2016 | Cronin |

(56) References Cited

U.S. PATENT DOCUMENTS

| | | |
|---|---|---|
| 9,495,015 B1 | 11/2016 | Kahn et al. |
| 9,495,860 B2 | 11/2016 | Lett |
| 9,498,066 B2 | 11/2016 | Christianson et al. |
| 9,498,704 B1 | 11/2016 | Cohen et al. |
| 9,500,464 B2 | 11/2016 | Coza |
| 9,504,414 B2 | 11/2016 | Coza et al. |
| 9,509,269 B1 | 11/2016 | Rosenberg |
| 9,511,259 B2 | 12/2016 | Mountain |
| 9,517,378 B2 | 12/2016 | Ashby et al. |
| 9,517,406 B2 | 12/2016 | Shum et al. |
| 9,529,385 B2 | 12/2016 | Connor |
| 9,529,437 B2 | 12/2016 | Kahn et al. |
| 9,532,002 B2 | 12/2016 | Glass et al. |
| 9,532,734 B2 | 1/2017 | Hoffman et al. |
| 9,533,228 B2 | 1/2017 | Dugan |
| 9,535,505 B2 | 1/2017 | Erkkila et al. |
| 9,536,449 B2 | 1/2017 | Connor |
| 9,539,458 B1 | 1/2017 | Ross |
| 9,545,535 B2 | 1/2017 | Lagree |
| 9,545,541 B2 | 1/2017 | Aragones et al. |
| 9,549,585 B2 | 1/2017 | Amos et al. |
| 9,563,336 B2 | 2/2017 | Barak et al. |
| 9,563,700 B2 | 2/2017 | Garmark et al. |
| 9,579,534 B2 | 2/2017 | Sutkowski et al. |
| 9,582,071 B2 | 2/2017 | Baldwin et al. |
| 9,585,563 B2 | 3/2017 | Mensinger et al. |
| 9,586,090 B2 | 3/2017 | Watterson et al. |
| 9,589,482 B2 | 3/2017 | Baldwin et al. |
| 9,594,433 B2 | 3/2017 | Baldwin et al. |
| 9,597,540 B2 | 3/2017 | Arnold |
| 9,599,981 B2 | 3/2017 | Crabtree |
| 9,600,079 B2 | 3/2017 | Baldwin et al. |
| 9,602,210 B2 | 3/2017 | Berlin et al. |
| 9,604,096 B2 | 3/2017 | Arnold et al. |
| 9,604,099 B2 | 3/2017 | Taylor |
| 9,610,475 B1 | 4/2017 | DeKnock et al. |
| 9,610,506 B2 | 4/2017 | Dugan |
| 9,615,215 B2 | 4/2017 | Yuen et al. |
| 9,615,785 B2 | 4/2017 | Rocker et al. |
| 9,616,281 B2 | 4/2017 | Hsiung |
| 9,621,959 B2 | 4/2017 | Mountain |
| 9,622,537 B2 | 4/2017 | Amos et al. |
| 9,623,286 B1 | 4/2017 | Chen |
| 9,628,286 B1 | 4/2017 | Nguyen et al. |
| 9,632,746 B2 | 4/2017 | Keipert et al. |
| 9,636,543 B2 | 5/2017 | Dyer et al. |
| 9,636,567 B2 | 5/2017 | Brammer et al. |
| 9,642,764 B2 | 5/2017 | Kuehne et al. |
| 9,646,137 B2 | 5/2017 | Gilley et al. |
| 9,646,481 B2 | 5/2017 | Messenger et al. |
| 9,647,758 B2 | 5/2017 | Hazani |
| 9,655,053 B2 | 5/2017 | Park et al. |
| 9,658,066 B2 | 5/2017 | Yuen et al. |
| 9,661,355 B2 | 5/2017 | Ho |
| 9,661,781 B2 | 5/2017 | Anolik et al. |
| 9,669,261 B2 | 6/2017 | Eder |
| 9,672,196 B2 | 6/2017 | Shachar et al. |
| 9,672,754 B2 | 6/2017 | Yuen et al. |
| 9,673,904 B2 | 6/2017 | Palanisamy et al. |
| 9,678,626 B2 | 6/2017 | Whang |
| 9,681,313 B2 | 6/2017 | Malach |
| 9,682,306 B2 | 6/2017 | Lin et al. |
| 9,687,689 B2 | 6/2017 | Lin |
| 9,692,844 B2 | 6/2017 | Messenger et al. |
| RE46,481 E | 7/2017 | Sako et al. |
| 9,694,247 B2 | 7/2017 | Nurnberg |
| 9,697,740 B2 | 7/2017 | Zhang et al. |
| 9,700,802 B2 | 7/2017 | Dugan |
| 9,701,530 B2 | 7/2017 | Kline |
| 9,707,447 B1 | 7/2017 | Lopez Babodilla |
| 9,710,711 B2 | 7/2017 | Dibenedetto et al. |
| 9,712,629 B2 | 7/2017 | Molettiere et al. |
| 9,713,739 B2 | 7/2017 | Dalmia |
| 9,715,774 B2 | 7/2017 | Baldwin et al. |
| 9,719,797 B2 | 8/2017 | Fino et al. |
| 9,720,443 B2 | 8/2017 | Malhotra |
| 9,723,393 B2 | 8/2017 | Nguyen et al. |
| 9,724,563 B2 | 8/2017 | Schmidt |
| 9,724,589 B2 | 8/2017 | Baudhuin |
| 9,728,059 B2 | 8/2017 | Arnold et al. |
| 9,729,921 B2 | 8/2017 | Kim et al. |
| 9,729,989 B2 | 8/2017 | Marten |
| 9,730,025 B2 | 8/2017 | Yuen et al. |
| 9,730,228 B2 | 8/2017 | Harel |
| 9,730,619 B2 | 8/2017 | Messenger et al. |
| 9,734,184 B1 | 8/2017 | Lagace et al. |
| 9,737,261 B2 | 8/2017 | Coza et al. |
| 9,743,861 B2 | 8/2017 | Giedwoyn et al. |
| 9,756,895 B2 | 9/2017 | Rice et al. |
| 9,757,605 B2 | 9/2017 | Olson et al. |
| 9,757,611 B1 | 9/2017 | Colburn |
| 9,763,581 B2 | 9/2017 | Bonutti et al. |
| 9,767,212 B2 | 9/2017 | Lavi et al. |
| 9,769,522 B2 | 9/2017 | Richardson |
| 9,772,612 B2 | 9/2017 | McCarthy, III et al. |
| 9,775,123 B2 | 9/2017 | Harel |
| 9,776,039 B1 | 10/2017 | Xu |
| 9,776,042 B2 | 10/2017 | Prokhorov |
| 9,778,280 B2 | 10/2017 | Yuen et al. |
| 9,782,125 B2 | 10/2017 | Berner, Jr. et al. |
| 9,782,625 B1 | 10/2017 | Blum et al. |
| 9,789,362 B1 | 10/2017 | Su et al. |
| 9,792,361 B1 | 10/2017 | Geer |
| 9,795,828 B2 | 10/2017 | Andrade |
| 9,797,920 B2 | 10/2017 | Kahn et al. |
| 9,798,309 B2 | 10/2017 | Tirpak |
| 9,801,547 B2 | 10/2017 | Yuen et al. |
| 9,802,081 B2 | 10/2017 | Ridgel et al. |
| 9,808,202 B2 | 11/2017 | Wu et al. |
| 9,808,673 B2 | 11/2017 | Robinson |
| 9,811,639 B2 | 11/2017 | Aragones et al. |
| 9,814,920 B1 | 11/2017 | Monterrey |
| 9,814,928 B2 | 11/2017 | Taylor |
| 9,814,930 B2 | 11/2017 | Manzke et al. |
| 9,818,285 B2 | 11/2017 | Clarke et al. |
| 9,819,561 B2 | 11/2017 | Freishtat et al. |
| 9,819,754 B2 | 11/2017 | Park et al. |
| 9,821,191 B2 | 11/2017 | Abbondanza |
| 9,821,212 B2 | 11/2017 | Kolman et al. |
| 9,824,110 B2 | 11/2017 | Giudici et al. |
| 9,824,578 B2 | 11/2017 | Burton et al. |
| 9,829,327 B2 | 11/2017 | Nagy et al. |
| 9,833,141 B2 | 12/2017 | Kampman et al. |
| 9,833,658 B2 | 12/2017 | Wiener et al. |
| 9,838,736 B2 | 12/2017 | Smith et al. |
| 9,841,077 B2 | 12/2017 | Modrezejewski et al. |
| 9,849,333 B2 | 12/2017 | Fung |
| 9,849,361 B2 | 12/2017 | Coza et al. |
| 9,852,271 B2 | 12/2017 | Aragones et al. |
| 9,858,307 B2 | 1/2018 | Sultan et al. |
| 9,861,300 B2 | 1/2018 | Gettelman et al. |
| 9,866,596 B2 | 1/2018 | Das et al. |
| 9,880,805 B1 | 1/2018 | Guralnick |
| 9,881,326 B2 | 1/2018 | Gilley et al. |
| 9,882,736 B2 | 1/2018 | Lett |
| 9,882,992 B2 | 1/2018 | Baldwin et al. |
| 9,886,309 B2 | 2/2018 | Alles et al. |
| 9,886,871 B1 | 2/2018 | Rauhala et al. |
| 9,892,417 B2 | 2/2018 | Shachar et al. |
| 9,901,772 B2 | 2/2018 | Crowley et al. |
| 9,901,780 B2 | 2/2018 | DeLuca et al. |
| 9,906,572 B2 | 2/2018 | Wang et al. |
| 9,907,396 B1 | 3/2018 | Labrosse et al. |
| 9,910,498 B2 | 3/2018 | Kutliroff et al. |
| 9,914,003 B2 | 3/2018 | Kuehne et al. |
| 9,919,198 B2 | 3/2018 | Romeo et al. |
| 9,921,726 B1 | 3/2018 | Sculley et al. |
| 9,940,161 B1 | 4/2018 | Kahn et al. |
| 9,940,682 B2 | 4/2018 | Hoffman et al. |
| 9,943,159 B1 | 4/2018 | Novikova |
| 9,943,719 B2 | 4/2018 | Smith et al. |
| 9,943,722 B2 | 4/2018 | Dalebout |
| 9,946,857 B2 | 4/2018 | Beals |
| 9,948,349 B2 | 4/2018 | Malach |

(56) References Cited

U.S. PATENT DOCUMENTS

| | | |
|---|---|---|
| 9,948,477 B2 | 4/2018 | Marten |
| 9,950,209 B2 | 4/2018 | Yim et al. |
| 9,960,980 B2 | 5/2018 | Wilson |
| 9,962,081 B2 | 5/2018 | Mensinger et al. |
| 9,962,305 B2 | 5/2018 | Yamada et al. |
| 9,962,576 B2 | 5/2018 | Anderson |
| 9,965,059 B2 | 5/2018 | Myers et al. |
| 9,967,614 B2 | 5/2018 | McCarthy, III |
| 9,974,997 B2 | 5/2018 | Cei |
| 9,977,874 B2 | 5/2018 | Aragones et al. |
| 9,983,011 B2 | 5/2018 | Mountain |
| 9,986,315 B2 | 5/2018 | Oleson et al. |
| 9,987,513 B2 | 6/2018 | Yim et al. |
| 9,989,507 B2 | 6/2018 | Benn |
| 9,996,066 B2 | 6/2018 | Beals |
| 10,004,656 B2 | 6/2018 | Whalen et al. |
| 10,004,940 B2 | 6/2018 | Badarneh |
| 10,008,090 B2 | 6/2018 | Yuen et al. |
| 10,013,986 B1 | 7/2018 | Bhaya et al. |
| 10,015,216 B2 | 7/2018 | Wang et al. |
| 10,016,655 B2 | 7/2018 | Lagree |
| 10,021,188 B2 | 7/2018 | Oleson et al. |
| 10,022,589 B2 | 7/2018 | Case, Jr. et al. |
| 10,022,590 B2 | 7/2018 | Foley et al. |
| 10,029,172 B2 | 7/2018 | Galasso et al. |
| 10,035,010 B1 | 7/2018 | Wagstaff |
| 10,037,053 B2 | 7/2018 | Malhotra |
| 10,038,952 B2 | 7/2018 | Labrosse et al. |
| 2001/0001303 A1 | 5/2001 | Ohsuga et al. |
| 2001/0028350 A1 | 10/2001 | Matsuoka et al. |
| 2001/0049320 A1 | 12/2001 | Cohen |
| 2001/0053883 A1 | 12/2001 | Yoshimura et al. |
| 2002/0004439 A1 | 1/2002 | Galbraith et al. |
| 2002/0013717 A1 | 1/2002 | Ando |
| 2002/0016235 A1 | 2/2002 | Ashby et al. |
| 2002/0022555 A1 | 2/2002 | Nesci |
| 2002/0024521 A1 | 2/2002 | Goden |
| 2002/0026292 A1 | 2/2002 | Isami |
| 2002/0031756 A1 | 3/2002 | Holtz |
| 2002/0042912 A1 | 4/2002 | Iijima |
| 2002/0047867 A1 | 4/2002 | Mault |
| 2002/0054244 A1 | 5/2002 | Holtz |
| 2002/0055419 A1 | 5/2002 | Hinnebusch |
| 2002/0055422 A1 | 5/2002 | Airmet |
| 2002/0055857 A1 | 5/2002 | Mault |
| 2002/0060335 A1 | 5/2002 | Edgar |
| 2002/0062236 A1 | 5/2002 | Murashita |
| 2002/0068887 A1 | 6/2002 | Kikumoto |
| 2002/0068991 A1 | 6/2002 | Fitzsimmons, Jr. |
| 2002/0070954 A1 | 6/2002 | Lang |
| 2002/0077219 A1 | 6/2002 | Cohen |
| 2002/0077221 A1 | 6/2002 | Dalebout et al. |
| 2002/0083122 A1 | 6/2002 | Lemchen |
| 2002/0086779 A1 | 7/2002 | Wilkinson |
| 2002/0088337 A1 | 7/2002 | Devecka |
| 2002/0091043 A1 | 7/2002 | Rexach |
| 2002/0091796 A1 | 7/2002 | Higginson |
| 2002/0106617 A1 | 8/2002 | Hersh |
| 2002/0107058 A1 | 8/2002 | Namba et al. |
| 2002/0109710 A1 | 8/2002 | Holtz et al. |
| 2002/0111541 A1 | 8/2002 | Bibl et al. |
| 2002/0116266 A1 | 8/2002 | Marshall |
| 2002/0128119 A1 | 9/2002 | Arai |
| 2002/0138023 A1 | 9/2002 | Kume et al. |
| 2002/0151413 A1 | 10/2002 | Dalebout |
| 2002/0156387 A1 | 10/2002 | Dardik |
| 2002/0160883 A1 | 10/2002 | Dugan |
| 2002/0164929 A1 | 11/2002 | Pinson |
| 2002/0169634 A1 | 11/2002 | Nishi |
| 2002/0173407 A1 | 11/2002 | Bowman |
| 2002/0194604 A1 | 12/2002 | Sanchez et al. |
| 2002/0198776 A1 | 12/2002 | Nara |
| 2003/0004424 A1 | 1/2003 | Birnbaum |
| 2003/0013072 A1 | 1/2003 | Thomas |
| 2003/0033600 A1 | 2/2003 | Cliff et al. |
| 2003/0040348 A1 | 2/2003 | Martens |
| 2003/0041076 A1 | 2/2003 | Lucovsky |
| 2003/0043986 A1 | 3/2003 | Creamer et al. |
| 2003/0043989 A1 | 3/2003 | Creamer et al. |
| 2003/0044021 A1 | 3/2003 | Wilkinson et al. |
| 2003/0063133 A1 | 4/2003 | Foote et al. |
| 2003/0065561 A1 | 4/2003 | Brown et al. |
| 2003/0069108 A1 | 4/2003 | Rubinstein |
| 2003/0088196 A1 | 5/2003 | Steve |
| 2003/0092540 A1 | 5/2003 | Gillen |
| 2003/0100406 A1 | 5/2003 | Millington |
| 2003/0104907 A1 | 6/2003 | Sankrithi |
| 2003/0105390 A1 | 6/2003 | Alessandri |
| 2003/0115157 A1 | 6/2003 | Circenis |
| 2003/0126593 A1 | 7/2003 | Mault |
| 2003/0138761 A1 | 7/2003 | Pesnell |
| 2003/0139254 A1 | 7/2003 | Chang |
| 2003/0142951 A1 | 7/2003 | Tsurugai |
| 2003/0148857 A1 | 8/2003 | Yu |
| 2003/0149344 A1 | 8/2003 | Nizan |
| 2003/0153436 A1 | 8/2003 | Ho |
| 2003/0158014 A1 | 8/2003 | Valentin-Sivico |
| 2003/0163287 A1 | 8/2003 | Vock et al. |
| 2003/0165802 A1 | 9/2003 | Murphy |
| 2003/0166434 A1 | 9/2003 | Lopez-Santillana et al. |
| 2003/0171189 A1 | 9/2003 | Kaufman |
| 2003/0171190 A1 | 9/2003 | Rice |
| 2003/0171192 A1 | 9/2003 | Wu |
| 2003/0176815 A1 | 9/2003 | Baba et al. |
| 2003/0207237 A1 | 11/2003 | Glezerman |
| 2003/0208113 A1 | 11/2003 | Mault et al. |
| 2003/0211449 A1 | 11/2003 | Seiller |
| 2003/0211916 A1 | 11/2003 | Capuano |
| 2003/0212536 A1 | 11/2003 | Wang |
| 2003/0214530 A1 | 11/2003 | Wang |
| 2003/0216228 A1 | 11/2003 | Rast |
| 2003/0220143 A1 | 11/2003 | Shteyn et al. |
| 2003/0227473 A1 | 12/2003 | Shih |
| 2004/0005959 A1 | 1/2004 | Takizawa |
| 2004/0005961 A1 | 1/2004 | Iund |
| 2004/0008220 A1 | 1/2004 | Snyder et al. |
| 2004/0010420 A1 | 1/2004 | Rooks |
| 2004/0012335 A1 | 1/2004 | Shon et al. |
| 2004/0014014 A1 | 1/2004 | Hess |
| 2004/0019654 A1 | 1/2004 | Powers |
| 2004/0027368 A1 | 2/2004 | Snyder et al. |
| 2004/0030762 A1 | 2/2004 | Silverthorne |
| 2004/0046692 A1 | 3/2004 | Robson |
| 2004/0051392 A1 | 3/2004 | Badarneh |
| 2004/0054350 A1 | 3/2004 | Shaughnessy |
| 2004/0063549 A1 | 4/2004 | Kuo |
| 2004/0072652 A1 | 4/2004 | Alessandri et al. |
| 2004/0077462 A1 | 4/2004 | Brown |
| 2004/0077975 A1 | 4/2004 | Zimmerman |
| 2004/0078208 A1 | 4/2004 | Burwell |
| 2004/0097331 A1 | 5/2004 | Zillig |
| 2004/0103146 A1 | 5/2004 | Park |
| 2004/0116837 A1 | 6/2004 | Yamaguchi |
| 2004/0116899 A1 | 6/2004 | Shaughnessy |
| 2004/0117072 A1 | 6/2004 | Takeda |
| 2004/0117214 A1 | 6/2004 | Shea |
| 2004/0127285 A1 | 7/2004 | Kavana |
| 2004/0127335 A1* | 7/2004 | Watterson .......... A63B 22/0023 482/8 |
| 2004/0157546 A1 | 8/2004 | Fantaay |
| 2004/0160336 A1 | 8/2004 | Hoch |
| 2004/0162188 A1 | 8/2004 | Watterson |
| 2004/0171464 A1 | 9/2004 | Ashby et al. |
| 2004/0171465 A1 | 9/2004 | Hald |
| 2004/0180719 A1 | 9/2004 | Feldman |
| 2004/0186390 A1 | 9/2004 | Ross et al. |
| 2004/0208943 A1 | 10/2004 | Miketin |
| 2004/0210661 A1 | 10/2004 | Thompson |
| 2004/0220017 A1 | 11/2004 | Gordon |
| 2004/0224740 A1 | 11/2004 | Ball et al. |
| 2004/0225239 A1 | 11/2004 | Yamamoto |
| 2004/0225532 A1 | 11/2004 | Gadiyak |
| 2004/0229730 A1 | 11/2004 | Ainsworth et al. |
| 2004/0230138 A1 | 11/2004 | Inoue et al. |

(56) References Cited

U.S. PATENT DOCUMENTS

| | | |
|---|---|---|
| 2004/0242388 A1 | 12/2004 | Kusminsky |
| 2004/0248713 A1 | 12/2004 | Campanaro |
| 2005/0003338 A1 | 1/2005 | Norcott et al. |
| 2005/0003931 A1 | 1/2005 | Mills et al. |
| 2005/0008992 A1 | 1/2005 | Westergaard et al. |
| 2005/0009668 A1 | 1/2005 | Savettiere |
| 2005/0012622 A1 | 1/2005 | Sutton |
| 2005/0013433 A1 | 1/2005 | Ghassabian |
| 2005/0014571 A1 | 1/2005 | Varner |
| 2005/0015281 A1 | 1/2005 | Clark et al. |
| 2005/0020887 A1 | 1/2005 | Goldberg |
| 2005/0026811 A1 | 2/2005 | Mjalli |
| 2005/0038698 A1 | 2/2005 | Lukose |
| 2005/0038699 A1 | 2/2005 | Lillibridge |
| 2005/0043145 A1 | 2/2005 | Anderson et al. |
| 2005/0048461 A1 | 3/2005 | Lahteenmaki |
| 2005/0054492 A1 | 3/2005 | Neff |
| 2005/0054940 A1 | 3/2005 | Almen |
| 2005/0060238 A1 | 3/2005 | Gravina et al. |
| 2005/0062841 A1 | 3/2005 | Rivera-Cintron |
| 2005/0064994 A1 | 3/2005 | Matsumoto |
| 2005/0071462 A1 | 3/2005 | Bodin et al. |
| 2005/0071463 A1 | 3/2005 | Bodin et al. |
| 2005/0075213 A1 | 4/2005 | Arick |
| 2005/0075222 A1 | 4/2005 | Adley |
| 2005/0075903 A1 | 4/2005 | Piccionelli |
| 2005/0079905 A1 | 4/2005 | Martens |
| 2005/0102172 A1 | 5/2005 | Sirmans |
| 2005/0107216 A1 | 5/2005 | Lee et al. |
| 2005/0107723 A1 | 5/2005 | Wehman et al. |
| 2005/0107726 A1 | 5/2005 | Oyen |
| 2005/0112601 A1 | 5/2005 | Hassibi |
| 2005/0113158 A1 | 5/2005 | Sterchi et al. |
| 2005/0113652 A1 | 5/2005 | Stark et al. |
| 2005/0113723 A1 | 5/2005 | Ueyama |
| 2005/0124463 A1 | 6/2005 | Yeo et al. |
| 2005/0131319 A1 | 6/2005 | Der Meer |
| 2005/0143226 A1 | 6/2005 | Heidecke |
| 2005/0148442 A1 | 7/2005 | Watterson |
| 2005/0159277 A1 | 7/2005 | Mcvay |
| 2005/0159278 A1 | 7/2005 | Mcvay |
| 2005/0159712 A1 | 7/2005 | Andersen |
| 2005/0160141 A1 | 7/2005 | Galley |
| 2005/0164832 A1 | 7/2005 | Maschke |
| 2005/0164838 A1 | 7/2005 | Watterson |
| 2005/0164839 A1 | 7/2005 | Watterson |
| 2005/0167907 A1 | 8/2005 | Curkendall et al. |
| 2005/0172311 A1 | 8/2005 | Hjelt et al. |
| 2005/0178210 A1 | 8/2005 | Lanham |
| 2005/0179202 A1 | 8/2005 | French et al. |
| 2005/0181347 A1 | 8/2005 | Barnes et al. |
| 2005/0187704 A1 | 8/2005 | Peters |
| 2005/0195094 A1 | 9/2005 | White |
| 2005/0202862 A1 | 9/2005 | Shuman et al. |
| 2005/0209050 A1 | 9/2005 | Bartels |
| 2005/0209051 A1 | 9/2005 | Santomassimo et al. |
| 2005/0209887 A1 | 9/2005 | Pollner |
| 2005/0210169 A1 | 9/2005 | Chou |
| 2005/0212202 A1 | 9/2005 | Meyer |
| 2005/0213442 A1 | 9/2005 | Sako |
| 2005/0215335 A1 | 9/2005 | Marquardt |
| 2005/0227811 A1 | 10/2005 | Shum et al. |
| 2005/0228883 A1 | 10/2005 | Brown |
| 2005/0233859 A1 | 10/2005 | Takai |
| 2005/0233861 A1 | 10/2005 | Hickman |
| 2005/0233866 A1 | 10/2005 | Miyamaru et al. |
| 2005/0238182 A1 | 10/2005 | Shih et al. |
| 2005/0240444 A1 | 10/2005 | Wooten |
| 2005/0245370 A1 | 11/2005 | Boland |
| 2005/0245431 A1 | 11/2005 | Demmer et al. |
| 2005/0269601 A1 | 12/2005 | Tsubaki |
| 2005/0272561 A1 | 12/2005 | Cammerata |
| 2005/0272564 A1 | 12/2005 | Pyles et al. |
| 2005/0272577 A1 | 12/2005 | Olson |
| 2005/0274188 A1 | 12/2005 | Cabanis et al. |
| 2005/0288954 A1 | 12/2005 | McCarthy et al. |
| 2006/0004265 A1 | 1/2006 | Pulkkinen et al. |
| 2006/0009332 A1 | 1/2006 | Jones |
| 2006/0013351 A1 | 1/2006 | Crider |
| 2006/0019224 A1 | 1/2006 | Behar et al. |
| 2006/0020174 A1 | 1/2006 | Matsumura |
| 2006/0020556 A1 | 1/2006 | Hamnen |
| 2006/0020990 A1 | 1/2006 | McEneaney |
| 2006/0034161 A1 | 2/2006 | Muller |
| 2006/0035758 A1 | 2/2006 | Rogozinski |
| 2006/0035774 A1 | 2/2006 | Marks |
| 2006/0040244 A1 | 2/2006 | Kain |
| 2006/0040246 A1 | 2/2006 | Ding et al. |
| 2006/0046807 A1 | 3/2006 | Sanchez |
| 2006/0046898 A1 | 3/2006 | Harvey |
| 2006/0058155 A1 | 3/2006 | Kumar |
| 2006/0063644 A1 | 3/2006 | Yang |
| 2006/0063980 A1 | 3/2006 | Hwang et al. |
| 2006/0069102 A1 | 3/2006 | Leban et al. |
| 2006/0084551 A1 | 4/2006 | Volpe, Jr. |
| 2006/0084851 A1 | 4/2006 | Lee et al. |
| 2006/0089238 A1 | 4/2006 | Huang et al. |
| 2006/0097453 A1 | 5/2006 | Feldman |
| 2006/0100546 A1 | 5/2006 | Silk |
| 2006/0104047 A1 | 5/2006 | Guzman |
| 2006/0105888 A1 | 5/2006 | Piane, Jr. |
| 2006/0111944 A1 | 5/2006 | Sirmans, Jr. |
| 2006/0116558 A1 | 6/2006 | Jang |
| 2006/0122034 A1 | 6/2006 | Chen |
| 2006/0122035 A1 | 6/2006 | Felix |
| 2006/0122468 A1 | 6/2006 | Tavor |
| 2006/0122474 A1 | 6/2006 | Teller et al. |
| 2006/0128534 A1 | 6/2006 | Roque |
| 2006/0129432 A1 | 6/2006 | Choi et al. |
| 2006/0142665 A1 | 6/2006 | Garay et al. |
| 2006/0160639 A1 | 7/2006 | Klein |
| 2006/0160667 A1 | 7/2006 | Oglesby et al. |
| 2006/0161455 A1 | 7/2006 | Anastasia |
| 2006/0161621 A1 | 7/2006 | Rosenberg |
| 2006/0161656 A1 | 7/2006 | Sorvisto |
| 2006/0161850 A1 | 7/2006 | Seaberg |
| 2006/0173556 A1 | 8/2006 | Rosenberg |
| 2006/0173828 A1 | 8/2006 | Rosenberg |
| 2006/0179044 A1 | 8/2006 | Rosenberg |
| 2006/0179056 A1 | 8/2006 | Rosenberg |
| 2006/0183602 A1 | 8/2006 | Astilean |
| 2006/0183980 A1 | 8/2006 | Yang |
| 2006/0184427 A1 | 8/2006 | Singh |
| 2006/0186197 A1 | 8/2006 | Rosenberg |
| 2006/0189440 A1 | 8/2006 | Gravagne |
| 2006/0189854 A1 | 8/2006 | Webb et al. |
| 2006/0194679 A1 | 8/2006 | Hatcher |
| 2006/0195361 A1 | 8/2006 | Rosenberg |
| 2006/0198613 A1 | 9/2006 | Lee |
| 2006/0199155 A1 | 9/2006 | Mosher |
| 2006/0203972 A1 | 9/2006 | Hays |
| 2006/0205349 A1 | 9/2006 | Passier et al. |
| 2006/0205564 A1 | 9/2006 | Peterson |
| 2006/0217231 A1 | 9/2006 | Parks et al. |
| 2006/0218253 A1 | 9/2006 | Hays |
| 2006/0223635 A1 | 10/2006 | Rosenberg |
| 2006/0223637 A1 | 10/2006 | Rosenberg |
| 2006/0223674 A1 | 10/2006 | Korkie |
| 2006/0223680 A1 | 10/2006 | Chang |
| 2006/0223681 A1 | 10/2006 | Loane |
| 2006/0228683 A1 | 10/2006 | Jianping |
| 2006/0229058 A1 | 10/2006 | Rosenberg |
| 2006/0229163 A1 | 10/2006 | Waters |
| 2006/0229164 A1 | 10/2006 | Einav |
| 2006/0234840 A1 | 10/2006 | Watson |
| 2006/0240947 A1 | 10/2006 | Qu |
| 2006/0247095 A1 | 11/2006 | Rummerfield |
| 2006/0247098 A1 | 11/2006 | Raniere |
| 2006/0248965 A1 | 11/2006 | Wyatt |
| 2006/0251638 A1 | 11/2006 | Guenzler-Pukall |
| 2006/0252600 A1 | 11/2006 | Grogan |
| 2006/0252602 A1 | 11/2006 | Brown |
| 2006/0252608 A1 | 11/2006 | Kang et al. |
| 2006/0253010 A1 | 11/2006 | Brady et al. |

(56) References Cited

U.S. PATENT DOCUMENTS

| | | |
|---|---|---|
| 2006/0253210 A1 | 11/2006 | Rosenberg |
| 2006/0256007 A1 | 11/2006 | Rosenberg |
| 2006/0256008 A1 | 11/2006 | Rosenberg |
| 2006/0258515 A1 | 11/2006 | Kang et al. |
| 2006/0259275 A1 | 11/2006 | Maschke |
| 2006/0259574 A1 | 11/2006 | Rosenberg |
| 2006/0262752 A1 | 11/2006 | Moore et al. |
| 2006/0264299 A1 | 11/2006 | Farinelli et al. |
| 2006/0264730 A1 | 11/2006 | Stivoric et al. |
| 2006/0265469 A1 | 11/2006 | Estrade |
| 2006/0269251 A1 | 11/2006 | Hsu |
| 2006/0271286 A1 | 11/2006 | Rosenberg |
| 2006/0276306 A1 | 12/2006 | Pan et al. |
| 2006/0281605 A1 | 12/2006 | Lo |
| 2006/0283050 A1 | 12/2006 | Carnes et al. |
| 2006/0287089 A1 | 12/2006 | Addington et al. |
| 2006/0293608 A1 | 12/2006 | Rothman et al. |
| 2006/0293617 A1 | 12/2006 | Einav et al. |
| 2007/0004562 A1 | 1/2007 | Pan et al. |
| 2007/0004736 A1 | 1/2007 | Kubo |
| 2007/0005395 A1 | 1/2007 | Singh |
| 2007/0006489 A1 | 1/2007 | Case et al. |
| 2007/0011027 A1 | 1/2007 | Melendez |
| 2007/0011391 A1 | 1/2007 | Kim et al. |
| 2007/0011920 A1 | 1/2007 | DiBenedetto |
| 2007/0013655 A1 | 1/2007 | Rosenberg |
| 2007/0014422 A1 | 1/2007 | Wesemann et al. |
| 2007/0016444 A1 | 1/2007 | Holkkola |
| 2007/0016930 A1 | 1/2007 | Wesemann et al. |
| 2007/0026958 A1 | 2/2007 | Barasch et al. |
| 2007/0026999 A1 | 2/2007 | Merolle et al. |
| 2007/0027000 A1 | 2/2007 | Shirai et al. |
| 2007/0028749 A1 | 2/2007 | Basson |
| 2007/0032351 A1 | 2/2007 | Reyes |
| 2007/0033068 A1 | 2/2007 | Rao |
| 2007/0033069 A1 | 2/2007 | Rao |
| 2007/0038137 A1 | 2/2007 | Arand et al. |
| 2007/0038153 A1 | 2/2007 | Basson |
| 2007/0042866 A1 | 2/2007 | Skilken |
| 2007/0042868 A1 | 2/2007 | Fisher |
| 2007/0049461 A1 | 3/2007 | Kim et al. |
| 2007/0049462 A1 | 3/2007 | Asukai et al. |
| 2007/0049470 A1 | 3/2007 | Pyles et al. |
| 2007/0051369 A1 | 3/2007 | Choi et al. |
| 2007/0054778 A1 | 3/2007 | Blanarovich |
| 2007/0060408 A1 | 3/2007 | Schultz et al. |
| 2007/0060446 A1 | 3/2007 | Asukai et al. |
| 2007/0060898 A1 | 3/2007 | Shaughnessy |
| 2007/0061314 A1 | 3/2007 | Rosenberg |
| 2007/0063033 A1 | 3/2007 | Silverbrook |
| 2007/0072156 A1 | 3/2007 | Kaufman et al. |
| 2007/0074617 A1 | 4/2007 | Vergo |
| 2007/0075127 A1 | 4/2007 | Rosenberg |
| 2007/0083095 A1 | 4/2007 | Rippo et al. |
| 2007/0083323 A1 | 4/2007 | Rosenberg |
| 2007/0083975 A1 | 4/2007 | Senegal |
| 2007/0093360 A1 | 4/2007 | Neff |
| 2007/0093369 A1 | 4/2007 | Bocchicchio |
| 2007/0100595 A1 | 5/2007 | Earles |
| 2007/0100666 A1 | 5/2007 | Stivoric et al. |
| 2007/0106484 A1 | 5/2007 | Sweatman et al. |
| 2007/0111753 A1 | 5/2007 | Vock |
| 2007/0111858 A1 | 5/2007 | Dugan |
| 2007/0117680 A1 | 5/2007 | Neff |
| 2007/0117683 A1 | 5/2007 | Ercanbrack et al. |
| 2007/0117693 A1 | 5/2007 | Ilioi |
| 2007/0122786 A1 | 5/2007 | Relan et al. |
| 2007/0123390 A1 | 5/2007 | Mathis |
| 2007/0124762 A1 | 5/2007 | Chickering et al. |
| 2007/0129220 A1 | 6/2007 | Bardha |
| 2007/0129907 A1 | 6/2007 | Demon |
| 2007/0135264 A1 | 6/2007 | Rosenberg |
| 2007/0135738 A1 | 6/2007 | Bonutti |
| 2007/0136093 A1 | 6/2007 | Rankin et al. |
| 2007/0140403 A1 | 6/2007 | Yuguchi et al. |
| 2007/0142175 A1 | 6/2007 | Morgan |
| 2007/0142177 A1 | 6/2007 | Simms et al. |
| 2007/0142179 A1 | 6/2007 | Terao et al. |
| 2007/0146347 A1 | 6/2007 | Rosenberg |
| 2007/0149362 A1 | 6/2007 | Lee |
| 2007/0150188 A1 | 6/2007 | Rosenberg |
| 2007/0153639 A1 | 7/2007 | Lafever |
| 2007/0155589 A1 | 7/2007 | Feldman |
| 2007/0156335 A1 | 7/2007 | McBride et al. |
| 2007/0161459 A1 | 7/2007 | Watson |
| 2007/0161466 A1 | 7/2007 | Oglesby |
| 2007/0167291 A1 | 7/2007 | Kuo |
| 2007/0167293 A1 | 7/2007 | Nally |
| 2007/0169381 A1 | 7/2007 | Gordon |
| 2007/0173355 A1 | 7/2007 | Klein |
| 2007/0176035 A1 | 8/2007 | Campbell |
| 2007/0179023 A1 | 8/2007 | Dyer |
| 2007/0179359 A1 | 8/2007 | Goodwin |
| 2007/0180737 A1 | 8/2007 | DiBenedetto et al. |
| 2007/0184953 A1 | 8/2007 | Luberski et al. |
| 2007/0189544 A1 | 8/2007 | Rosenberg |
| 2007/0191141 A1 | 8/2007 | Weber |
| 2007/0197193 A1 | 8/2007 | Zhou |
| 2007/0197345 A1 | 8/2007 | Wallace et al. |
| 2007/0197920 A1 | 8/2007 | Adams |
| 2007/0201727 A1 | 8/2007 | Birrell et al. |
| 2007/0202992 A1 | 8/2007 | Grasshoff |
| 2007/0203004 A1 | 8/2007 | Campanaro et al. |
| 2007/0207733 A1 | 9/2007 | Wong et al. |
| 2007/0208392 A1 | 9/2007 | Kuschner et al. |
| 2007/0208530 A1 | 9/2007 | Vock |
| 2007/0213110 A1 | 9/2007 | Rosenberg |
| 2007/0213126 A1 | 9/2007 | Deutsch et al. |
| 2007/0213178 A1 | 9/2007 | Lemmela |
| 2007/0213183 A1 | 9/2007 | Menektchiev |
| 2007/0218432 A1 | 9/2007 | Glass |
| 2007/0219057 A1 | 9/2007 | Fleishman |
| 2007/0219058 A1 | 9/2007 | Fleishman |
| 2007/0219059 A1 | 9/2007 | Schwartz |
| 2007/0219068 A1 | 9/2007 | Korfmacher |
| 2007/0219074 A1 | 9/2007 | Pride |
| 2007/0219457 A1 | 9/2007 | Lo |
| 2007/0225118 A1 | 9/2007 | Giorno |
| 2007/0225119 A1 | 9/2007 | Schenk |
| 2007/0232450 A1 | 10/2007 | Hanoun |
| 2007/0232452 A1 | 10/2007 | Hanoun |
| 2007/0232455 A1 | 10/2007 | Hanoun |
| 2007/0232461 A1 | 10/2007 | Jenkins |
| 2007/0232463 A1 | 10/2007 | Wu |
| 2007/0233743 A1 | 10/2007 | Rosenberg |
| 2007/0239479 A1 | 10/2007 | Arrasvuori |
| 2007/0243974 A1 | 10/2007 | Li |
| 2007/0245258 A1 | 10/2007 | Ginggen et al. |
| 2007/0249467 A1 | 10/2007 | Hong et al. |
| 2007/0249468 A1 | 10/2007 | Chen |
| 2007/0265138 A1 | 11/2007 | Ashby |
| 2007/0270663 A1 | 11/2007 | Ng et al. |
| 2007/0271116 A1 | 11/2007 | Wysocki et al. |
| 2007/0271387 A1 | 11/2007 | Lydon et al. |
| 2007/0272011 A1 | 11/2007 | Chapa, Jr. |
| 2007/0275825 A1 | 11/2007 | O'brien |
| 2007/0275826 A1 | 11/2007 | Niemimaki et al. |
| 2007/0275830 A1 | 11/2007 | Lee |
| 2007/0276870 A1 | 11/2007 | Rosenberg |
| 2007/0281828 A1 | 12/2007 | Rice |
| 2007/0283853 A1 | 12/2007 | Sun |
| 2007/0287141 A1 | 12/2007 | Milner |
| 2007/0287597 A1 | 12/2007 | Cameron |
| 2007/0287930 A1 | 12/2007 | Sutton |
| 2007/0288204 A1 | 12/2007 | Gienke et al. |
| 2007/0288251 A1 | 12/2007 | Ebrom |
| 2007/0288331 A1 | 12/2007 | Ebrom |
| 2007/0288476 A1 | 12/2007 | Flanagan, III |
| 2007/0293781 A1 | 12/2007 | Sims et al. |
| 2007/0298405 A1 | 12/2007 | Ebrom |
| 2007/0298935 A1 | 12/2007 | Badarneh |
| 2008/0004162 A1 | 1/2008 | Chen |
| 2008/0005276 A1 | 1/2008 | Frederick |
| 2008/0015061 A1 | 1/2008 | Klein |

(56) References Cited

U.S. PATENT DOCUMENTS

| | | |
|---|---|---|
| 2008/0015088 A1 | 1/2008 | Del Monaco |
| 2008/0020898 A1 | 1/2008 | Pyles |
| 2008/0026838 A1 | 1/2008 | Dunstan et al. |
| 2008/0027673 A1 | 1/2008 | Trumm |
| 2008/0032864 A1 | 2/2008 | Hakki |
| 2008/0032865 A1 | 2/2008 | Wu |
| 2008/0032870 A1 | 2/2008 | Wu |
| 2008/0037375 A1 | 2/2008 | Ellner |
| 2008/0045384 A1 | 2/2008 | Matsubara |
| 2008/0051258 A1 | 2/2008 | Schmehl |
| 2008/0051261 A1 | 2/2008 | Lewis |
| 2008/0051919 A1 | 2/2008 | Sakai et al. |
| 2008/0058170 A1 | 3/2008 | Giannascoli et al. |
| 2008/0059064 A1 | 3/2008 | Werner |
| 2008/0062818 A1 | 3/2008 | Plancon |
| 2008/0064571 A1 | 3/2008 | Lee |
| 2008/0076969 A1 | 3/2008 | Kraft |
| 2008/0076972 A1 | 3/2008 | Dorogusker et al. |
| 2008/0077489 A1 | 3/2008 | Gilley et al. |
| 2008/0082311 A1 | 4/2008 | Meijer et al. |
| 2008/0089551 A1 | 4/2008 | Heather et al. |
| 2008/0090703 A1 | 4/2008 | Rosenberg |
| 2008/0097633 A1 | 4/2008 | Jochelson et al. |
| 2008/0098797 A1 | 5/2008 | Considine |
| 2008/0103023 A1 | 5/2008 | Chung |
| 2008/0103024 A1 | 5/2008 | Habing |
| 2008/0108481 A1 | 5/2008 | Limma |
| 2008/0108917 A1 | 5/2008 | Joutras et al. |
| 2008/0109121 A1 | 5/2008 | Takeda |
| 2008/0109243 A1 | 5/2008 | Ebrom et al. |
| 2008/0109295 A1 | 5/2008 | McConochie |
| 2008/0109310 A1 | 5/2008 | Ebrom et al. |
| 2008/0109841 A1 | 5/2008 | Heather et al. |
| 2008/0109851 A1 | 5/2008 | Heather et al. |
| 2008/0119332 A1 | 5/2008 | Roman |
| 2008/0119333 A1 | 5/2008 | Bowser |
| 2008/0119337 A1 | 5/2008 | Wilkins |
| 2008/0120436 A1 | 5/2008 | Cowgill et al. |
| 2008/0129825 A1 | 6/2008 | DeAngelis et al. |
| 2008/0132798 A1 | 6/2008 | Hong et al. |
| 2008/0139370 A1 | 6/2008 | Charnitski |
| 2008/0146334 A1 | 6/2008 | Kil |
| 2008/0146336 A1 | 6/2008 | Feldman |
| 2008/0146416 A1 | 6/2008 | Mueller et al. |
| 2008/0146890 A1 | 6/2008 | LeBoeuf et al. |
| 2008/0146892 A1 | 6/2008 | LeBoeuf et al. |
| 2008/0147502 A1 | 6/2008 | Baker |
| 2008/0153670 A1 | 6/2008 | Mckirdy |
| 2008/0153671 A1 | 6/2008 | Ogg et al. |
| 2008/0155077 A1 | 6/2008 | James |
| 2008/0161168 A1 | 7/2008 | Hsiao |
| 2008/0161653 A1 | 7/2008 | Lin et al. |
| 2008/0167535 A1 | 7/2008 | Stivoric et al. |
| 2008/0167536 A1 | 7/2008 | Teller |
| 2008/0167958 A1 | 7/2008 | Balaban et al. |
| 2008/0171636 A1 | 7/2008 | Usui et al. |
| 2008/0171922 A1 | 7/2008 | Teller |
| 2008/0171945 A1 | 7/2008 | Dotter |
| 2008/0172328 A1 | 7/2008 | Ajilian |
| 2008/0176655 A1 | 7/2008 | James |
| 2008/0176713 A1 | 7/2008 | Olivera Brizzio |
| 2008/0176721 A1 | 7/2008 | Boren |
| 2008/0179214 A1 | 7/2008 | Hall |
| 2008/0182685 A1 | 7/2008 | Marty et al. |
| 2008/0182724 A1 | 7/2008 | Guthrie |
| 2008/0183049 A1 | 7/2008 | Karkanias et al. |
| 2008/0183052 A1 | 7/2008 | Teller |
| 2008/0188354 A1 | 8/2008 | Pauws et al. |
| 2008/0189733 A1 | 8/2008 | Apostolopoulos |
| 2008/0191864 A1 | 8/2008 | Wolfson |
| 2008/0195258 A1 | 8/2008 | Schendel |
| 2008/0200778 A1 | 8/2008 | Taskinen |
| 2008/0204225 A1 | 8/2008 | Kitchen |
| 2008/0207401 A1 | 8/2008 | Harding |
| 2008/0207402 A1 | 8/2008 | Fisher et al. |
| 2008/0214358 A1 | 9/2008 | Ogg et al. |
| 2008/0214359 A1 | 9/2008 | Niva et al. |
| 2008/0214903 A1 | 9/2008 | Orbach |
| 2008/0218307 A1 | 9/2008 | Schoettle |
| 2008/0224988 A1 | 9/2008 | Whang |
| 2008/0229875 A1 | 9/2008 | Ray |
| 2008/0234023 A1 | 9/2008 | Mullahkhel et al. |
| 2008/0234113 A1 | 9/2008 | Einav |
| 2008/0242510 A1 | 10/2008 | Topel |
| 2008/0242511 A1 | 10/2008 | Munoz et al. |
| 2008/0242513 A1 | 10/2008 | Skilken et al. |
| 2008/0249736 A1 | 10/2008 | Prstojevich |
| 2008/0253378 A1 | 10/2008 | Curry |
| 2008/0254420 A1 | 10/2008 | Nerenberg |
| 2008/0254947 A1 | 10/2008 | Mackay |
| 2008/0255430 A1 | 10/2008 | Alexandersson et al. |
| 2008/0261636 A1 | 10/2008 | Lau et al. |
| 2008/0261776 A1 | 10/2008 | Skiba |
| 2008/0262381 A1 | 10/2008 | Kolen |
| 2008/0262392 A1 | 10/2008 | Ananny et al. |
| 2008/0267444 A1 | 10/2008 | Simons-Nikolova et al. |
| 2008/0269017 A1 | 10/2008 | Ungari |
| 2008/0273008 A1 | 11/2008 | Chang |
| 2008/0287262 A1 | 11/2008 | Chou |
| 2008/0293023 A1 | 11/2008 | Diehl |
| 2008/0295129 A1 | 11/2008 | Laut |
| 2008/0296883 A1 | 12/2008 | Burkhardtsmaier |
| 2008/0300109 A1 | 12/2008 | Karkanias et al. |
| 2008/0300110 A1 | 12/2008 | Smith et al. |
| 2008/0300914 A1 | 12/2008 | Karkanias et al. |
| 2008/0305934 A1 | 12/2008 | Medina |
| 2008/0306762 A1 | 12/2008 | James |
| 2008/0312039 A1 | 12/2008 | Bucay-Bissu |
| 2008/0312041 A1 | 12/2008 | Schwabe et al. |
| 2008/0319787 A1 | 12/2008 | Stivoric |
| 2008/0319796 A1 | 12/2008 | Stivoric |
| 2008/0319855 A1 | 12/2008 | Stivoric |
| 2009/0005224 A1 | 1/2009 | Davis et al. |
| 2009/0017991 A1 | 1/2009 | Hung |
| 2009/0023554 A1 | 1/2009 | Shim |
| 2009/0023556 A1 | 1/2009 | Daly |
| 2009/0024233 A1 | 1/2009 | Shirai et al. |
| 2009/0028005 A1 | 1/2009 | You et al. |
| 2009/0029831 A1 | 1/2009 | Weier |
| 2009/0040231 A1 | 2/2009 | Sano et al. |
| 2009/0040301 A1 | 2/2009 | Sandler et al. |
| 2009/0041298 A1 | 2/2009 | Sandler et al. |
| 2009/0042174 A1 | 2/2009 | Aries |
| 2009/0048073 A1 | 2/2009 | Roimicher |
| 2009/0048493 A1 | 2/2009 | James et al. |
| 2009/0048939 A1 | 2/2009 | Williams |
| 2009/0049092 A1 | 2/2009 | Capio et al. |
| 2009/0054207 A1 | 2/2009 | Lin et al. |
| 2009/0061870 A1 | 3/2009 | Finkelstein et al. |
| 2009/0062598 A1 | 3/2009 | Haisma et al. |
| 2009/0069722 A1 | 3/2009 | Flaction et al. |
| 2009/0075781 A1 | 3/2009 | Schwarzberg et al. |
| 2009/0076335 A1 | 3/2009 | Schwarzberg et al. |
| 2009/0076903 A1 | 3/2009 | Schwarzberg et al. |
| 2009/0082880 A1 | 3/2009 | Saunders |
| 2009/0085873 A1 | 4/2009 | Betts et al. |
| 2009/0088248 A1 | 4/2009 | Stevens |
| 2009/0088299 A1 | 4/2009 | Chen |
| 2009/0093341 A1 | 4/2009 | James |
| 2009/0098980 A1 | 4/2009 | Waters |
| 2009/0105047 A1 | 4/2009 | Guidi et al. |
| 2009/0105052 A1 | 4/2009 | Dalebout et al. |
| 2009/0105560 A1 | 4/2009 | Solomon |
| 2009/0109346 A1 | 4/2009 | Viarani et al. |
| 2009/0111656 A1 | 4/2009 | Sullivan et al. |
| 2009/0111658 A1 | 4/2009 | Juan |
| 2009/0111670 A1 | 4/2009 | Williams |
| 2009/0117890 A1 | 5/2009 | Jacobsen et al. |
| 2009/0118099 A1 | 5/2009 | Fisher |
| 2009/0119032 A1 | 5/2009 | Meyer |
| 2009/0120208 A1 | 5/2009 | Meyer |
| 2009/0120210 A1 | 5/2009 | Phillips et al. |
| 2009/0124460 A1 | 5/2009 | Chen |
| 2009/0128342 A1 | 5/2009 | Cohen |

(56) References Cited

U.S. PATENT DOCUMENTS

| | | |
|---|---|---|
| 2009/0128516 A1 | 5/2009 | Rimon et al. |
| 2009/0144080 A1 | 6/2009 | Gray et al. |
| 2009/0144084 A1 | 6/2009 | Neumaier |
| 2009/0144639 A1 | 6/2009 | Nims et al. |
| 2009/0149299 A1 | 6/2009 | Tchao et al. |
| 2009/0149721 A1 | 6/2009 | Yang |
| 2009/0150178 A1 | 6/2009 | Sutton et al. |
| 2009/0156364 A1 | 6/2009 | Simeoni |
| 2009/0163321 A1 | 6/2009 | Watterson |
| 2009/0163323 A1 | 6/2009 | Bocchicchio |
| 2009/0171229 A1 | 7/2009 | Saldarelli |
| 2009/0174558 A1 | 7/2009 | White |
| 2009/0176526 A1 | 7/2009 | Altman |
| 2009/0176581 A1 | 7/2009 | Barnes et al. |
| 2009/0176625 A1 | 7/2009 | Giannelli et al. |
| 2009/0177068 A1 | 7/2009 | Stivoric et al. |
| 2009/0181826 A1 | 7/2009 | Turner |
| 2009/0191988 A1 | 7/2009 | Klein |
| 2009/0192391 A1 | 7/2009 | Lovitt et al. |
| 2009/0192871 A1 | 7/2009 | Deacon et al. |
| 2009/0193344 A1 | 7/2009 | Smyers |
| 2009/0195350 A1 | 8/2009 | Tsern et al. |
| 2009/0197739 A1 | 8/2009 | Hashimoto |
| 2009/0197740 A1 | 8/2009 | Julskjaer et al. |
| 2009/0204422 A1 | 8/2009 | James |
| 2009/0204668 A1 | 8/2009 | Huang |
| 2009/0205482 A1 | 8/2009 | Shirai et al. |
| 2009/0209393 A1 | 8/2009 | Crater et al. |
| 2009/0210078 A1 | 8/2009 | Crowley |
| 2009/0216629 A1 | 8/2009 | James |
| 2009/0217178 A1 | 8/2009 | Niyogi et al. |
| 2009/0238400 A1 | 9/2009 | Im |
| 2009/0239714 A1 | 9/2009 | Sellers |
| 2009/0240858 A1 | 9/2009 | Takebayashi |
| 2009/0247366 A1 | 10/2009 | Frumer |
| 2009/0253109 A1 | 10/2009 | Anvari |
| 2009/0257323 A1 | 10/2009 | Soltani |
| 2009/0258710 A1 | 10/2009 | Quatrochi et al. |
| 2009/0262088 A1 | 10/2009 | Moll-Carrillo et al. |
| 2009/0263772 A1 | 10/2009 | Root |
| 2009/0264260 A1 | 10/2009 | Piaget et al. |
| 2009/0265649 A1 | 10/2009 | Schlossberg et al. |
| 2009/0267783 A1 | 10/2009 | Vock et al. |
| 2009/0269728 A1 | 10/2009 | Verstegen et al. |
| 2009/0270743 A1 | 10/2009 | Dugan |
| 2009/0278707 A1 | 11/2009 | Biggins et al. |
| 2009/0282080 A1 | 11/2009 | Schlossberg et al. |
| 2009/0286653 A1 | 11/2009 | Wiber |
| 2009/0288887 A1 | 11/2009 | Chen |
| 2009/0292178 A1 | 11/2009 | Ellis et al. |
| 2009/0309891 A1 | 12/2009 | Karkanias et al. |
| 2009/0312151 A1 | 12/2009 | Thieberger |
| 2009/0312158 A1 | 12/2009 | Trevino et al. |
| 2009/0312658 A1 | 12/2009 | Thieberger |
| 2010/0003647 A1 | 1/2010 | Brown et al. |
| 2010/0009809 A1 | 1/2010 | Carrington |
| 2010/0016742 A1 | 1/2010 | James |
| 2010/0017402 A1 | 1/2010 | Fleming et al. |
| 2010/0019593 A1 | 1/2010 | Ritchey |
| 2010/0022354 A1 | 1/2010 | Fisher |
| 2010/0024590 A1 | 2/2010 | O'neill |
| 2010/0031803 A1 | 2/2010 | Lozada et al. |
| 2010/0035726 A1 | 2/2010 | Fisher |
| 2010/0036736 A1 | 2/2010 | McGee et al. |
| 2010/0038149 A1 | 2/2010 | Corel |
| 2010/0041000 A1 | 2/2010 | Glass |
| 2010/0050082 A1 | 2/2010 | Katz et al. |
| 2010/0056339 A1 | 3/2010 | Chen |
| 2010/0056340 A1 | 3/2010 | Ellis |
| 2010/0056876 A1 | 3/2010 | Ellis |
| 2010/0062818 A1 | 3/2010 | Haughay, Jr. et al. |
| 2010/0064255 A1 | 3/2010 | Rottler et al. |
| 2010/0068684 A1 | 3/2010 | Sabel |
| 2010/0075812 A1 | 3/2010 | Piaget et al. |
| 2010/0076278 A1 | 3/2010 | van der Zande et al. |
| 2010/0077564 A1 | 4/2010 | Saier et al. |
| 2010/0079291 A1 | 4/2010 | Kroll et al. |
| 2010/0081116 A1 | 4/2010 | Barasch et al. |
| 2010/0081548 A1 | 4/2010 | Labedz |
| 2010/0087701 A1 | 4/2010 | Berka et al. |
| 2010/0093492 A1 | 4/2010 | Watterson et al. |
| 2010/0093493 A1 | 4/2010 | Eldridge |
| 2010/0099437 A1 | 4/2010 | Moerdijk |
| 2010/0099954 A1 | 4/2010 | Dickinson et al. |
| 2010/0112536 A1 | 5/2010 | Claassen et al. |
| 2010/0113222 A1 | 5/2010 | Radow |
| 2010/0113223 A1 | 5/2010 | Chiles et al. |
| 2010/0113948 A1 | 5/2010 | Yang et al. |
| 2010/0125183 A1 | 5/2010 | Vayalattu et al. |
| 2010/0137049 A1 | 6/2010 | Epstein |
| 2010/0137106 A1 | 6/2010 | Oshima et al. |
| 2010/0146055 A1 | 6/2010 | Hannuksela |
| 2010/0152546 A1 | 6/2010 | Behan et al. |
| 2010/0156625 A1 | 6/2010 | Ruha |
| 2010/0156760 A1 | 6/2010 | Cheswick |
| 2010/0160013 A1 | 6/2010 | Sanders |
| 2010/0160014 A1 | 6/2010 | Galasso et al. |
| 2010/0160115 A1 | 6/2010 | Morris et al. |
| 2010/0167801 A1 | 7/2010 | Karkanias et al. |
| 2010/0167876 A1 | 7/2010 | Cheng |
| 2010/0173276 A1 | 7/2010 | Vasin |
| 2010/0179035 A1 | 7/2010 | Carnahan |
| 2010/0179883 A1 | 7/2010 | Devolites |
| 2010/0182436 A1 | 7/2010 | Boman et al. |
| 2010/0184565 A1 | 7/2010 | Avellino |
| 2010/0188405 A1 | 7/2010 | Haughay, Jr. et al. |
| 2010/0190610 A1 | 7/2010 | Pryor |
| 2010/0191462 A1 | 7/2010 | Kobuya et al. |
| 2010/0197462 A1 | 8/2010 | Piane, Jr. |
| 2010/0204013 A1 | 8/2010 | Chen |
| 2010/0208038 A1 | 8/2010 | Kutliroff |
| 2010/0208082 A1 | 8/2010 | Buchner et al. |
| 2010/0211439 A1 | 8/2010 | Marci et al. |
| 2010/0216536 A1 | 8/2010 | Gagner |
| 2010/0216600 A1 | 8/2010 | Noffsinger |
| 2010/0217096 A1 | 8/2010 | Nanikashvili |
| 2010/0217099 A1 | 8/2010 | Leboeuf |
| 2010/0217102 A1 | 8/2010 | LeBoeuf et al. |
| 2010/0222165 A1 | 9/2010 | Nurnberg et al. |
| 2010/0227542 A1 | 9/2010 | Goldmann |
| 2010/0234184 A1 | 9/2010 | Le Page |
| 2010/0234693 A1 | 9/2010 | Srinivasan et al. |
| 2010/0240458 A1 | 9/2010 | Gaiba et al. |
| 2010/0240495 A1 | 9/2010 | Law |
| 2010/0240945 A1 | 9/2010 | Bikko |
| 2010/0241018 A1 | 9/2010 | Vogel |
| 2010/0243514 A1 | 9/2010 | Samain et al. |
| 2010/0247081 A1 | 9/2010 | Victoria Pons |
| 2010/0248901 A1 | 9/2010 | Martens |
| 2010/0255884 A1 | 10/2010 | Konkka et al. |
| 2010/0255965 A1 | 10/2010 | Chen |
| 2010/0259043 A1 | 10/2010 | Balsamo |
| 2010/0261580 A1 | 10/2010 | Lannon |
| 2010/0271367 A1 | 10/2010 | Vaden et al. |
| 2010/0274100 A1 | 10/2010 | Behar |
| 2010/0279823 A1 | 11/2010 | Waters |
| 2010/0281463 A1 | 11/2010 | Estrade |
| 2010/0283601 A1 | 11/2010 | Tai et al. |
| 2010/0289772 A1 | 11/2010 | Miller |
| 2010/0292599 A1 | 11/2010 | Oleson et al. |
| 2010/0298098 A1 | 11/2010 | Ercan |
| 2010/0298655 A1 | 11/2010 | McCombie et al. |
| 2010/0298656 A1 | 11/2010 | McCombie et al. |
| 2010/0298661 A1 | 11/2010 | McCombie et al. |
| 2010/0300272 A1 | 12/2010 | Scherf |
| 2010/0302250 A1 | 12/2010 | Hoebel |
| 2010/0312596 A1 | 12/2010 | Saffari et al. |
| 2010/0324387 A1 | 12/2010 | Moon |
| 2010/0327603 A1 | 12/2010 | Suaan |
| 2011/0003663 A1 | 1/2011 | Chiu et al. |
| 2011/0009240 A1 | 1/2011 | Chiu et al. |
| 2011/0009249 A1 | 1/2011 | Campanaro et al. |
| 2011/0015039 A1 | 1/2011 | Shea |
| 2011/0015468 A1 | 1/2011 | Aarts et al. |

(56) References Cited

U.S. PATENT DOCUMENTS

| | | |
|---|---|---|
| 2011/0021319 A1 | 1/2011 | Nissila et al. |
| 2011/0021953 A1 | 1/2011 | Sanematsu |
| 2011/0028277 A1 | 2/2011 | Merli |
| 2011/0032105 A1 | 2/2011 | Hoffman et al. |
| 2011/0034300 A1 | 2/2011 | Hall |
| 2011/0039659 A1 | 2/2011 | Kim et al. |
| 2011/0046519 A1 | 2/2011 | Raheman |
| 2011/0053131 A1 | 3/2011 | Regnier |
| 2011/0054242 A1 | 3/2011 | Bender |
| 2011/0054270 A1 | 3/2011 | Derchak |
| 2011/0054272 A1 | 3/2011 | Derchak |
| 2011/0054359 A1 | 3/2011 | Sazonov et al. |
| 2011/0054809 A1 | 3/2011 | Templeman |
| 2011/0063114 A1 | 3/2011 | Ikoyan |
| 2011/0066056 A1 | 3/2011 | Huang |
| 2011/0072955 A1 | 3/2011 | Turner |
| 2011/0082006 A1 | 4/2011 | Ishii |
| 2011/0082011 A1 | 4/2011 | Ellis |
| 2011/0082015 A1 | 4/2011 | Dreissigacker et al. |
| 2011/0082397 A1 | 4/2011 | Alberts |
| 2011/0086707 A1 | 4/2011 | Loveland |
| 2011/0087076 A1 | 4/2011 | Brynelsen et al. |
| 2011/0087137 A1 | 4/2011 | Hanoun |
| 2011/0087446 A1 | 4/2011 | Redmond |
| 2011/0091842 A1 | 4/2011 | Dugan |
| 2011/0096764 A1 | 4/2011 | Tunioli et al. |
| 2011/0098615 A1 | 4/2011 | Whalen et al. |
| 2011/0105278 A1 | 5/2011 | Fabbri |
| 2011/0105279 A1 | 5/2011 | Herranen |
| 2011/0105920 A1 | 5/2011 | Haataja |
| 2011/0106597 A1 | 5/2011 | Ferdman et al. |
| 2011/0117529 A1 | 5/2011 | Barash |
| 2011/0118084 A1 | 5/2011 | Tsai et al. |
| 2011/0118086 A1 | 5/2011 | Radow |
| 2011/0118089 A1 | 5/2011 | Ellis |
| 2011/0124469 A1 | 5/2011 | Uhlir |
| 2011/0124978 A1 | 5/2011 | Williams |
| 2011/0125063 A1 | 5/2011 | Shalon et al. |
| 2011/0131005 A1 | 6/2011 | Ueshima et al. |
| 2011/0136627 A1 | 6/2011 | Williams |
| 2011/0140904 A1 | 6/2011 | Kashi |
| 2011/0143769 A1 | 6/2011 | Jones |
| 2011/0152033 A1 | 6/2011 | Yang |
| 2011/0152635 A1 | 6/2011 | Morris et al. |
| 2011/0152696 A1 | 6/2011 | Ryan |
| 2011/0163939 A1 | 7/2011 | Tam et al. |
| 2011/0164044 A1 | 7/2011 | Huang |
| 2011/0164175 A1 | 7/2011 | Chung et al. |
| 2011/0165995 A1 | 7/2011 | Paulus |
| 2011/0165996 A1 | 7/2011 | Paulus |
| 2011/0165997 A1 | 7/2011 | Reich |
| 2011/0165998 A1 | 7/2011 | Lau et al. |
| 2011/0167447 A1 | 7/2011 | Wong |
| 2011/0172058 A1 | 7/2011 | Deaconu |
| 2011/0172059 A1 | 7/2011 | Watterson et al. |
| 2011/0172060 A1 | 7/2011 | Morales et al. |
| 2011/0175744 A1 | 7/2011 | Englert et al. |
| 2011/0175989 A1 | 7/2011 | Islam |
| 2011/0176943 A1 | 7/2011 | Tran et al. |
| 2011/0177919 A1 | 7/2011 | Tamari |
| 2011/0179068 A1 | 7/2011 | O'brien |
| 2011/0181420 A1 | 7/2011 | Mack et al. |
| 2011/0183307 A1 | 7/2011 | Shum et al. |
| 2011/0184225 A1 | 7/2011 | Whitall et al. |
| 2011/0184247 A1 | 7/2011 | Contant et al. |
| 2011/0188668 A1 | 8/2011 | Donaldson |
| 2011/0191123 A1 | 8/2011 | Buzynski |
| 2011/0195819 A1 | 8/2011 | Shaw |
| 2011/0199393 A1 | 8/2011 | Nurse et al. |
| 2011/0201476 A1 | 8/2011 | Solomon |
| 2011/0202236 A1 | 8/2011 | Galasso et al. |
| 2011/0214148 A1 | 9/2011 | Gossweiler, III et al. |
| 2011/0218086 A1 | 9/2011 | Boren |
| 2011/0221672 A1 | 9/2011 | Osterhout et al. |
| 2011/0222375 A1 | 9/2011 | Tsubata et al. |
| 2011/0224057 A1 | 9/2011 | Wu |
| 2011/0224498 A1 | 9/2011 | Banet et al. |
| 2011/0229862 A1 | 9/2011 | Parikh |
| 2011/0230732 A1 | 9/2011 | Edman et al. |
| 2011/0238217 A1 | 9/2011 | Kume |
| 2011/0245633 A1 | 10/2011 | Goldberg et al. |
| 2011/0263385 A1 | 10/2011 | Shea |
| 2011/0264305 A1 | 10/2011 | Choe |
| 2011/0267196 A1 | 11/2011 | Hu et al. |
| 2011/0270135 A1 | 11/2011 | Dooley |
| 2011/0275489 A1 | 11/2011 | Apau |
| 2011/0276312 A1 | 11/2011 | Shalon et al. |
| 2011/0283188 A1 | 11/2011 | Farrenkopf et al. |
| 2011/0283231 A1 | 11/2011 | Richstein et al. |
| 2011/0295083 A1 | 12/2011 | Doelling et al. |
| 2011/0311955 A1 | 12/2011 | Forsten et al. |
| 2011/0319229 A1 | 12/2011 | Corbalis et al. |
| 2011/0320380 A1 | 12/2011 | Zahn et al. |
| 2012/0004074 A1 | 1/2012 | Schelzig |
| 2012/0004076 A1 | 1/2012 | Fenster |
| 2012/0015778 A1 | 1/2012 | Lee et al. |
| 2012/0015784 A1 | 1/2012 | Reed |
| 2012/0021873 A1 | 1/2012 | Brunner |
| 2012/0024237 A1 | 2/2012 | Rice |
| 2012/0028761 A1 | 2/2012 | Dorogusker et al. |
| 2012/0035487 A1 | 2/2012 | Werner et al. |
| 2012/0036557 A1 | 2/2012 | Li |
| 2012/0050818 A1 | 3/2012 | Watanabe |
| 2012/0055718 A1 | 3/2012 | Chen |
| 2012/0065031 A1 | 3/2012 | Buzzanco |
| 2012/0071301 A1 | 3/2012 | Kaylor et al. |
| 2012/0078127 A1 | 3/2012 | McDonald et al. |
| 2012/0079429 A1 | 3/2012 | Stathacopoulos et al. |
| 2012/0079529 A1 | 3/2012 | Harris et al. |
| 2012/0081531 A1 | 4/2012 | DeAngelis et al. |
| 2012/0083669 A1 | 4/2012 | Abujbara |
| 2012/0083705 A1 | 4/2012 | Yuen et al. |
| 2012/0084807 A1 | 4/2012 | Thompson et al. |
| 2012/0084811 A1 | 4/2012 | Thompson |
| 2012/0084812 A1 | 4/2012 | Thompson et al. |
| 2012/0090446 A1 | 4/2012 | Moreno |
| 2012/0092327 A1 | 4/2012 | Adhikari |
| 2012/0096357 A1 | 4/2012 | Folgner et al. |
| 2012/0096405 A1 | 4/2012 | Seo |
| 2012/0105867 A1 | 5/2012 | Komatsu |
| 2012/0108914 A1 | 5/2012 | Bravomalo |
| 2012/0115695 A1 | 5/2012 | Watterson et al. |
| 2012/0116550 A1 | 5/2012 | Hoffman et al. |
| 2012/0116684 A1 | 5/2012 | Ingrassia et al. |
| 2012/0116806 A1 | 5/2012 | Stark et al. |
| 2012/0122063 A1 | 5/2012 | Chen et al. |
| 2012/0125559 A1 | 5/2012 | Fadell et al. |
| 2012/0129139 A1 | 5/2012 | Partovi |
| 2012/0143358 A1 | 6/2012 | Adams et al. |
| 2012/0149996 A1 | 6/2012 | Stivoric et al. |
| 2012/0153015 A1 | 6/2012 | Gomez et al. |
| 2012/0157265 A1 | 6/2012 | Kao |
| 2012/0159563 A1 | 6/2012 | Gomez et al. |
| 2012/0165703 A1 | 6/2012 | Bottum |
| 2012/0174608 A1 | 7/2012 | Kumamoto et al. |
| 2012/0179772 A1 | 7/2012 | Hinnebusch |
| 2012/0190504 A1 | 7/2012 | Lee et al. |
| 2012/0202656 A1 | 8/2012 | Dorsay |
| 2012/0208153 A1 | 8/2012 | Bolla |
| 2012/0214590 A1 | 8/2012 | Newhouse et al. |
| 2012/0217758 A1 | 8/2012 | Chen |
| 2012/0218184 A1 | 8/2012 | Wissmar |
| 2012/0225412 A1 | 9/2012 | Wagner |
| 2012/0228385 A1 | 9/2012 | Deluca |
| 2012/0233002 A1 | 9/2012 | Abujbara |
| 2012/0237906 A9 | 9/2012 | Glass |
| 2012/0237911 A1 | 9/2012 | Watterson |
| 2012/0238800 A1 | 9/2012 | Naujokat et al. |
| 2012/0238851 A1 | 9/2012 | Kamen |
| 2012/0251983 A1 | 10/2012 | Golden |
| 2012/0253234 A1 | 10/2012 | Yang et al. |
| 2012/0253489 A1 | 10/2012 | Dugan |
| 2012/0258433 A1 | 10/2012 | Hope et al. |
| 2012/0271121 A1 | 10/2012 | Della Torre et al. |

(56) References Cited

U.S. PATENT DOCUMENTS

| | | |
|---|---|---|
| 2012/0277040 A1 | 11/2012 | Vincent et al. |
| 2012/0285986 A1 | 11/2012 | Irvin |
| 2012/0315986 A1 | 12/2012 | Walling |
| 2012/0315987 A1 | 12/2012 | Walling |
| 2012/0316406 A1 | 12/2012 | Rahman et al. |
| 2012/0316455 A1 | 12/2012 | Rahman et al. |
| 2012/0316456 A1 | 12/2012 | Rahman et al. |
| 2012/0316458 A1 | 12/2012 | Rahman et al. |
| 2012/0317024 A1 | 12/2012 | Rahman et al. |
| 2012/0322628 A1 | 12/2012 | Gautier |
| 2012/0323496 A1 | 12/2012 | Burroughs |
| 2012/0326873 A1 | 12/2012 | Utter, II |
| 2012/0329027 A1 | 12/2012 | Lewolt |
| 2012/0329611 A1 | 12/2012 | Bouchard |
| 2013/0002533 A1 | 1/2013 | Burroughs et al. |
| 2013/0009993 A1 | 1/2013 | Horseman |
| 2013/0011818 A1 | 1/2013 | Shum et al. |
| 2013/0014155 A1 | 1/2013 | Clarke et al. |
| 2013/0015945 A1 | 1/2013 | Chang |
| 2013/0017888 A1 | 1/2013 | King |
| 2013/0018668 A1 | 1/2013 | Goldberg et al. |
| 2013/0029807 A1 | 1/2013 | Amsel |
| 2013/0035209 A1 | 2/2013 | Gilley et al. |
| 2013/0035612 A1 | 2/2013 | Mason et al. |
| 2013/0040271 A1 | 2/2013 | Rytky et al. |
| 2013/0040783 A1 | 2/2013 | Duda et al. |
| 2013/0041590 A1 | 2/2013 | Burich et al. |
| 2013/0041617 A1 | 2/2013 | Pease et al. |
| 2013/0053218 A1 | 2/2013 | Barker |
| 2013/0053717 A1 | 2/2013 | Vandine et al. |
| 2013/0053990 A1 | 2/2013 | Ackland |
| 2013/0065680 A1 | 3/2013 | Zavadsky |
| 2013/0073093 A1 | 3/2013 | Songkakul |
| 2013/0083003 A1 | 4/2013 | Perez et al. |
| 2013/0085038 A1 | 4/2013 | Fischer |
| 2013/0090565 A1 | 4/2013 | Quy |
| 2013/0097635 A1 | 4/2013 | Yerli |
| 2013/0105565 A1 | 5/2013 | Kamprath |
| 2013/0108995 A1 | 5/2013 | DePasqua et al. |
| 2013/0116091 A1 | 5/2013 | Fritz |
| 2013/0116514 A1 | 5/2013 | Kroner et al. |
| 2013/0127636 A1 | 5/2013 | Aryanpur et al. |
| 2013/0135115 A1 | 5/2013 | Johnson et al. |
| 2013/0137552 A1 | 5/2013 | Kemp et al. |
| 2013/0141235 A1 | 6/2013 | Utter, II |
| 2013/0144464 A1 | 6/2013 | Dorogusker et al. |
| 2013/0148861 A1 | 6/2013 | Ferlatte et al. |
| 2013/0154441 A1 | 6/2013 | Redmond |
| 2013/0158368 A1 | 6/2013 | Pacione et al. |
| 2013/0165195 A1 | 6/2013 | Watterson |
| 2013/0172152 A1 | 7/2013 | Watterson |
| 2013/0173156 A1 | 7/2013 | Wither et al. |
| 2013/0174273 A1 | 7/2013 | Grab et al. |
| 2013/0177884 A1 | 7/2013 | Root |
| 2013/0178334 A1 | 7/2013 | Brammer |
| 2013/0184843 A1 | 7/2013 | Ellis et al. |
| 2013/0190136 A1 | 7/2013 | Watterson |
| 2013/0191034 A1 | 7/2013 | Weast et al. |
| 2013/0196821 A1 | 8/2013 | Watterson et al. |
| 2013/0196822 A1 | 8/2013 | Watterson et al. |
| 2013/0203557 A1 | 8/2013 | Su |
| 2013/0208576 A1 | 8/2013 | Loree, IV et al. |
| 2013/0209972 A1 | 8/2013 | Carter et al. |
| 2013/0210581 A1 | 8/2013 | Watterson et al. |
| 2013/0210582 A1 | 8/2013 | Del Toro et al. |
| 2013/0216982 A1 | 8/2013 | Bennett et al. |
| 2013/0216990 A1 | 8/2013 | Chu et al. |
| 2013/0228063 A1 | 9/2013 | Turner |
| 2013/0231226 A1 | 9/2013 | Bonutti |
| 2013/0231575 A1 | 9/2013 | Erkkila et al. |
| 2013/0233097 A1 | 9/2013 | Hayner |
| 2013/0245966 A1 | 9/2013 | Burroughs et al. |
| 2013/0260965 A1 | 10/2013 | Chia et al. |
| 2013/0273509 A1 | 10/2013 | Mutti |
| 2013/0274067 A1 | 10/2013 | Watterson et al. |
| 2013/0274635 A1 | 10/2013 | Coza et al. |
| 2013/0280682 A1 | 10/2013 | Levine et al. |
| 2013/0282157 A1 | 10/2013 | Shin et al. |
| 2013/0282447 A1 | 10/2013 | Himanen et al. |
| 2013/0288223 A1 | 10/2013 | Watterson et al. |
| 2013/0289886 A1 | 10/2013 | Ricks |
| 2013/0289932 A1 | 10/2013 | Baechler |
| 2013/0290364 A1 | 10/2013 | Minvielle |
| 2013/0297642 A1 | 11/2013 | Minvielle |
| 2013/0298019 A1 | 11/2013 | Henderson |
| 2013/0303837 A1 | 11/2013 | Berka et al. |
| 2013/0310221 A1 | 11/2013 | Zuber et al. |
| 2013/0310230 A1 | 11/2013 | Norris |
| 2013/0310658 A1 | 11/2013 | Ricks |
| 2013/0316830 A1 | 11/2013 | Sedzin et al. |
| 2013/0325394 A1 | 12/2013 | Yuen et al. |
| 2013/0328416 A1 | 12/2013 | Whitworth et al. |
| 2013/0337974 A1 | 12/2013 | Yanev et al. |
| 2013/0345978 A1 | 12/2013 | Lush et al. |
| 2014/0011645 A1 | 1/2014 | Johnson et al. |
| 2014/0031174 A1 | 1/2014 | Huang |
| 2014/0031703 A1 | 1/2014 | Rayner et al. |
| 2014/0039329 A1 | 2/2014 | Kampman et al. |
| 2014/0039840 A1 | 2/2014 | Yuen et al. |
| 2014/0045656 A1 | 2/2014 | Zhang |
| 2014/0052280 A1 | 2/2014 | Yuen et al. |
| 2014/0058806 A1 | 2/2014 | Guenette et al. |
| 2014/0063180 A1 | 3/2014 | Sharma |
| 2014/0066264 A1 | 3/2014 | Haddon |
| 2014/0069838 A1 | 3/2014 | Minvielle |
| 2014/0074265 A1 | 3/2014 | Arginsky |
| 2014/0085077 A1 | 3/2014 | Luna et al. |
| 2014/0087923 A1 | 3/2014 | Warren |
| 2014/0089836 A1 | 3/2014 | Damani et al. |
| 2014/0094941 A1 | 4/2014 | Ellis et al. |
| 2014/0099614 A1 | 4/2014 | Hu et al. |
| 2014/0100464 A1 | 4/2014 | Kaleal et al. |
| 2014/0106322 A1 | 4/2014 | Durand |
| 2014/0113779 A1 | 4/2014 | Loach |
| 2014/0121471 A1 | 5/2014 | Walker |
| 2014/0125618 A1 | 5/2014 | Panther et al. |
| 2014/0129240 A1 | 5/2014 | Zhang |
| 2014/0134582 A1 | 5/2014 | Konishi |
| 2014/0135173 A1 | 5/2014 | Watterson |
| 2014/0135631 A1 | 5/2014 | Brumback et al. |
| 2014/0139450 A1 | 5/2014 | Levesque et al. |
| 2014/0141396 A1 | 5/2014 | Spratt |
| 2014/0142403 A1 | 5/2014 | Brumback et al. |
| 2014/0145935 A1 | 5/2014 | Sztuk |
| 2014/0150042 A1 | 5/2014 | Pacor et al. |
| 2014/0156041 A1 | 6/2014 | Martin |
| 2014/0156084 A1 | 6/2014 | Rahman et al. |
| 2014/0156228 A1 | 6/2014 | Molettiere et al. |
| 2014/0156308 A1 | 6/2014 | Ohnemus et al. |
| 2014/0156645 A1 | 6/2014 | Brust et al. |
| 2014/0162230 A1 | 6/2014 | Akopian |
| 2014/0163429 A1 | 6/2014 | Tropper et al. |
| 2014/0164611 A1 | 6/2014 | Molettiere et al. |
| 2014/0171272 A1 | 6/2014 | Hawkins, III et al. |
| 2014/0172873 A1 | 6/2014 | Varoglu et al. |
| 2014/0173660 A1 | 6/2014 | Correa et al. |
| 2014/0180480 A1 | 6/2014 | Lee et al. |
| 2014/0194260 A1 | 7/2014 | Campanaro et al. |
| 2014/0195103 A1 | 7/2014 | Nassef |
| 2014/0197946 A1 | 7/2014 | Park et al. |
| 2014/0200691 A1 | 7/2014 | Lee et al. |
| 2014/0203943 A1 | 7/2014 | Kates |
| 2014/0205980 A1 | 7/2014 | Braier et al. |
| 2014/0206506 A1 | 7/2014 | Huang |
| 2014/0212857 A1 | 7/2014 | Sullivan et al. |
| 2014/0213416 A1 | 7/2014 | Wang |
| 2014/0214446 A1 | 7/2014 | Pera, Jr. |
| 2014/0220514 A1 | 8/2014 | Waldron et al. |
| 2014/0221168 A1 | 8/2014 | Chen |
| 2014/0221784 A1 | 8/2014 | Pacione et al. |
| 2014/0221854 A1 | 8/2014 | Wai |
| 2014/0228118 A1 | 8/2014 | Hardy et al. |
| 2014/0228649 A1 | 8/2014 | Rayner et al. |
| 2014/0235411 A1 | 8/2014 | Dailey |

(56) References Cited

U.S. PATENT DOCUMENTS

| | | |
|---|---|---|
| 2014/0249440 A1 | 9/2014 | Banet |
| 2014/0257535 A1 | 9/2014 | Morris et al. |
| 2014/0257537 A1 | 9/2014 | Stroupe et al. |
| 2014/0265072 A1 | 9/2014 | Chiu |
| 2014/0266939 A1 | 9/2014 | Baringer et al. |
| 2014/0270375 A1 | 9/2014 | Canavan et al. |
| 2014/0272894 A1 | 9/2014 | Grimes et al. |
| 2014/0273858 A1 | 9/2014 | Panther et al. |
| 2014/0274564 A1 | 9/2014 | Greenbaum |
| 2014/0274574 A1 | 9/2014 | Shorten et al. |
| 2014/0275852 A1 | 9/2014 | Hong et al. |
| 2014/0275854 A1 | 9/2014 | Venkatraman et al. |
| 2014/0278139 A1 | 9/2014 | Hong et al. |
| 2014/0278218 A1 | 9/2014 | Chang |
| 2014/0278220 A1 | 9/2014 | Yuen |
| 2014/0288438 A1 | 9/2014 | Venkatraman et al. |
| 2014/0288679 A1 | 9/2014 | McNamee |
| 2014/0288680 A1 | 9/2014 | Hoffman et al. |
| 2014/0308629 A1 | 10/2014 | Dugan |
| 2014/0309085 A1 | 10/2014 | Watterson et al. |
| 2014/0316192 A1 | 10/2014 | de Zambotti et al. |
| 2014/0335490 A1 | 11/2014 | Baarman et al. |
| 2014/0336796 A1 | 11/2014 | Agnew |
| 2014/0351150 A1 | 11/2014 | Ainsworth et al. |
| 2014/0358012 A1 | 12/2014 | Richards et al. |
| 2014/0363797 A1 | 12/2014 | Hu et al. |
| 2014/0363800 A1 | 12/2014 | Harris et al. |
| 2014/0371887 A1 | 12/2014 | Hoffman et al. |
| 2014/0380167 A1 | 12/2014 | Bloch et al. |
| 2015/0004579 A1 | 1/2015 | Shelton |
| 2015/0004580 A1 | 1/2015 | Shum et al. |
| 2015/0011362 A1 | 1/2015 | Oh et al. |
| 2015/0019135 A1 | 1/2015 | Kacyvenski et al. |
| 2015/0025660 A1 | 1/2015 | Prassler et al. |
| 2015/0031964 A1 | 1/2015 | Bly et al. |
| 2015/0079562 A1 | 3/2015 | Yeh et al. |
| 2015/0081209 A1 | 3/2015 | Yeh et al. |
| 2015/0081210 A1 | 3/2015 | Yeh et al. |
| 2015/0082408 A1 | 3/2015 | Yeh et al. |
| 2015/0087478 A1 | 3/2015 | Zhang et al. |
| 2015/0092972 A1 | 4/2015 | Lai et al. |
| 2015/0097700 A1 | 4/2015 | Holthouse |
| 2015/0099952 A1 | 4/2015 | Lain et al. |
| 2015/0105220 A1 | 4/2015 | Hong |
| 2015/0105881 A1 | 4/2015 | Guerrero et al. |
| 2015/0106868 A1 | 4/2015 | Lo |
| 2015/0118657 A1 | 4/2015 | Shrake et al. |
| 2015/0119197 A1 | 4/2015 | Liu |
| 2015/0126873 A1 | 5/2015 | Connor |
| 2015/0135284 A1 | 5/2015 | Bogard |
| 2015/0141202 A1 | 5/2015 | Ellis et al. |
| 2015/0151160 A1 | 6/2015 | Balakrishnan et al. |
| 2015/0154452 A1 | 6/2015 | Bentley et al. |
| 2015/0157918 A1 | 6/2015 | Tracy |
| 2015/0165269 A1 | 6/2015 | Herrala et al. |
| 2015/0181314 A1 | 6/2015 | Swanson |
| 2015/0186609 A1 | 7/2015 | Utter, II |
| 2015/0190679 A1 | 7/2015 | Carbone |
| 2015/0199494 A1 | 7/2015 | Koduri et al. |
| 2015/0209617 A1 | 7/2015 | Hsiao |
| 2015/0224363 A1 | 8/2015 | Clark et al. |
| 2015/0238815 A1 | 8/2015 | Lee |
| 2015/0248844 A1 | 9/2015 | Ellis et al. |
| 2015/0250420 A1 | 9/2015 | Longinotti-Buitoni et al. |
| 2015/0251055 A1 | 9/2015 | Ashby |
| 2015/0253210 A1 | 9/2015 | Ashby et al. |
| 2015/0255002 A1 | 9/2015 | Harris et al. |
| 2015/0258382 A1 | 9/2015 | Nolan et al. |
| 2015/0258384 A1 | 9/2015 | Suzuki |
| 2015/0262459 A1 | 9/2015 | Munro |
| 2015/0265903 A1 | 9/2015 | Kolen et al. |
| 2015/0269354 A1 | 9/2015 | Klassen |
| 2015/0272262 A1 | 10/2015 | Escamilla |
| 2015/0272473 A1 | 10/2015 | Zafiroglu |
| 2015/0273272 A1 | 10/2015 | Wang |
| 2015/0288926 A1 | 10/2015 | Glass et al. |
| 2015/0296020 A1 | 10/2015 | Granqvist et al. |
| 2015/0305961 A1 | 10/2015 | Broerman et al. |
| 2015/0306456 A1 | 10/2015 | Pasini et al. |
| 2015/0310062 A1 | 10/2015 | Wang et al. |
| 2015/0318015 A1 | 11/2015 | Bose et al. |
| 2015/0320588 A1 | 11/2015 | Connor |
| 2015/0324751 A1 | 11/2015 | Orenstein et al. |
| 2015/0327804 A1 | 11/2015 | Lefever et al. |
| 2015/0331449 A1 | 11/2015 | Ng |
| 2015/0335288 A1 | 11/2015 | Toth et al. |
| 2015/0339946 A1 | 11/2015 | Pacione et al. |
| 2015/0342815 A1 | 12/2015 | Watson |
| 2015/0346994 A1 | 12/2015 | Chanyontpatanakul |
| 2015/0351690 A1 | 12/2015 | Toth et al. |
| 2015/0352404 A1 | 12/2015 | Schwenger |
| 2015/0360133 A1 | 12/2015 | MacCallum et al. |
| 2015/0364026 A1 | 12/2015 | Rubin et al. |
| 2015/0364058 A1 | 12/2015 | Lagree |
| 2015/0366746 A1 | 12/2015 | Ashby |
| 2015/0367158 A1 | 12/2015 | Pretz et al. |
| 2015/0370320 A1 | 12/2015 | Connor |
| 2015/0379239 A1 | 12/2015 | Basta et al. |
| 2015/0381736 A1 | 12/2015 | Seltzer |
| 2016/0012749 A1 | 1/2016 | Connor |
| 2016/0018119 A1 | 1/2016 | Desmet et al. |
| 2016/0051184 A1 | 2/2016 | Wisbey et al. |
| 2016/0058245 A1 | 3/2016 | Smith et al. |
| 2016/0059077 A1 | 3/2016 | Paul et al. |
| 2016/0059078 A1 | 3/2016 | Liao |
| 2016/0061300 A1 | 3/2016 | Aoto et al. |
| 2016/0063615 A1 | 3/2016 | Watterson |
| 2016/0066818 A1 | 3/2016 | Cowley et al. |
| 2016/0067537 A1 | 3/2016 | Bayerlein et al. |
| 2016/0071014 A1 | 3/2016 | Brand et al. |
| 2016/0074701 A1 | 3/2016 | Wiener |
| 2016/0077547 A1 | 3/2016 | Aimone et al. |
| 2016/0089569 A1 | 3/2016 | Blahnik |
| 2016/0107029 A1 | 4/2016 | Kim et al. |
| 2016/0112684 A1 | 4/2016 | Connor |
| 2016/0136483 A1 | 5/2016 | Reich |
| 2016/0148535 A1 | 5/2016 | Ashby |
| 2016/0148536 A1 | 5/2016 | Ashby |
| 2016/0151603 A1 | 6/2016 | Shouldice et al. |
| 2016/0157740 A1 | 6/2016 | Kampman et al. |
| 2016/0171110 A1 | 6/2016 | Gao et al. |
| 2016/0184635 A1 | 6/2016 | Kwon |
| 2016/0206922 A1 | 7/2016 | Dalebout et al. |
| 2016/0219968 A1 | 8/2016 | Martin |
| 2016/0232811 A9 | 8/2016 | Connor |
| 2016/0249365 A1 | 8/2016 | Harel |
| 2016/0250519 A1 | 9/2016 | Watterson |
| 2016/0253918 A1 | 9/2016 | Watterson |
| 2016/0256082 A1 | 9/2016 | Ely et al. |
| 2016/0256745 A1 | 9/2016 | Brammer |
| 2016/0263426 A1 | 9/2016 | Mueller et al. |
| 2016/0279462 A1 | 9/2016 | Sutherland |
| 2016/0279470 A1 | 9/2016 | Hampton |
| 2016/0296053 A1 | 10/2016 | Bakhsh |
| 2016/0321932 A1 | 11/2016 | Mitchell |
| 2016/0346616 A1 | 12/2016 | Kirby et al. |
| 2016/0351070 A1 | 12/2016 | Aillon-Sohl |
| 2016/0367857 A1 | 12/2016 | Aragones et al. |
| 2016/0371998 A1 | 12/2016 | Fazeel |
| 2016/0375307 A1 | 12/2016 | Durham |
| 2017/0007886 A1 | 1/2017 | Alessandri |
| 2017/0011210 A1 | 1/2017 | Cheong |
| 2017/0020440 A1 | 1/2017 | Flitsch et al. |
| 2017/0036106 A1 | 2/2017 | Stechschulte et al. |
| 2017/0050069 A1 | 2/2017 | Ky |
| 2017/0050102 A1 | 2/2017 | Kelly |
| 2017/0056726 A1 | 3/2017 | Dalebout et al. |
| 2017/0063567 A1 | 3/2017 | Tanaka et al. |
| 2017/0065187 A1 | 3/2017 | Hsieh et al. |
| 2017/0065947 A1 | 3/2017 | Haney et al. |
| 2017/0082983 A1 | 3/2017 | Katzer et al. |
| 2017/0093451 A1 | 3/2017 | Chen et al. |
| 2017/0097717 A1 | 4/2017 | Anisetti et al. |
| 2017/0100636 A1 | 4/2017 | Umetsu et al. |

(56) References Cited

U.S. PATENT DOCUMENTS

| | | |
|---|---|---|
| 2017/0104425 A1 | 4/2017 | Meloche |
| 2017/0128783 A1 | 5/2017 | Hasegawa et al. |
| 2017/0128784 A1 | 5/2017 | Molins et al. |
| 2017/0136293 A1 | 5/2017 | Caccia |
| 2017/0136301 A1 | 5/2017 | Cameron |
| 2017/0136339 A1 | 5/2017 | Habiche |
| 2017/0144051 A1 | 5/2017 | Oleson et al. |
| 2017/0164876 A1 | 6/2017 | Hyde et al. |
| 2017/0180535 A1 | 6/2017 | Esenwein et al. |
| 2017/0193578 A1 | 7/2017 | Watterson |
| 2017/0225034 A1 | 8/2017 | Kass et al. |
| 2017/0235922 A1 | 8/2017 | Weast et al. |
| 2017/0252623 A1 | 9/2017 | Sharifi |
| 2017/0252641 A1 | 9/2017 | Morimura et al. |
| 2017/0266503 A1 | 9/2017 | Watterson et al. |
| 2017/0266532 A1 | 9/2017 | Watterson |
| 2017/0266533 A1 | 9/2017 | Dalebout |
| 2017/0266534 A1 | 9/2017 | Watterson |
| 2017/0270820 A1 | 9/2017 | Ashby |
| 2017/0274237 A1 | 9/2017 | Chang |
| 2017/0311817 A9 | 11/2017 | Hsieh et al. |
| 2017/0333755 A1 | 11/2017 | Rider |
| 2017/0354846 A1 | 12/2017 | Von Rueckmann |
| 2017/0364661 A1 | 12/2017 | Hamilton et al. |
| 2017/0365048 A1 | 12/2017 | Hamilton et al. |
| 2018/0008865 A9 | 1/2018 | Lannon et al. |
| 2018/0036572 A1 | 2/2018 | Hsu |
| 2018/0056111 A1 | 3/2018 | Chiang et al. |
| 2018/0084817 A1 | 3/2018 | Capell et al. |
| 2018/0085630 A1 | 3/2018 | Capell et al. |
| 2018/0085654 A1 | 3/2018 | Black et al. |
| 2018/0089396 A1 | 3/2018 | Capell et al. |
| 2018/0092603 A1 | 4/2018 | Duan et al. |
| 2018/0099116 A1 | 4/2018 | Ashby |
| 2018/0099184 A1 | 4/2018 | Eder |
| 2018/0099205 A1 | 4/2018 | Watterson |
| 2018/0109838 A1 | 4/2018 | Garcia et al. |
| 2018/0111034 A1 | 4/2018 | Watterson |
| 2018/0116599 A1 | 5/2018 | Bastide et al. |
| 2018/0117383 A1 | 5/2018 | Workman |
| 2018/0154206 A1 | 6/2018 | Kim |

* cited by examiner

SYSTEM AND METHOD FOR CONTROLLING AN EXERCISE DEVICE

CROSS-REFERENCE TO RELATED APPLICATIONS

This application is a continuation of U.S. patent application Ser. No. 13/734,970, filed Jan. 5, 2013, which claims priority to U.S. Provisional Patent Application No. 61/583,524 filed Jan. 5, 2012. Each of the aforementioned applications are incorporated herein in its entirety by reference.

TECHNICAL FIELD

In general, the present invention relates to exercise equipment. More specifically, the present invention relates to methods, systems, and devices for providing workout files that are compatible with a plurality of different exercise devices.

BACKGROUND

Stationary exercise devices have become an increasingly popular way to exercise. To combat the boredom that is often experienced by individuals that exercise with these devices, stationary exercise devices are often sold with a number of different workout files that are saved within the electronics of the device. These workout files may include a "fat burn" workout, a "hills" workout and/or other workout files. Limited memory space however, restricts the number of different workout files that can be saved within the electronics of the exercise device.

Efforts have been made to increase the number of workout files available on stationary exercise devices. For example, U.S. Pat. Nos. 7,645,213, 6,193,631, and 6,053,844 relate to various ways of providing additional workout files or control commands to exercise devices. Due to the differences in exercise devices, however, workout files have to this point been specifically tailored for each exercise device. In other words, workout files that control moveable members and/or actuators in one type of exercise device may not control moveable members and/or actuators in another type of exercise device. Further, a workout file that is compatible with one exercise device may not be compatible with other exercise devices in the same class. This may be due to the fact that the operating parameter range on one exercise device is different from the operating parameter range on another exercise device. For example, a workout file that is compatible with a treadmill having a deck that is inclinable to a twenty percent grade may not be compatible with a treadmill whose deck is only inclinable to a fifteen percent grade.

SUMMARY OF THE INVENTION

In one aspect of the disclosure, an exercise device includes a moveable member having one or more operating parameters that are selectively adjustable within a limited range and one or more actuators that selectively adjust the one or more selectively adjustable operating parameters within the limited range.

In another aspect that may be combined with any of the aspects herein, the exercise device has a receiving port that receives workout files.

In another aspect of the invention that may be combined with any of the aspects herein, the workout files have a first control command subset that provides instructions for controlling the one or more actuators that selectively adjust the operating parameters of the moveable member.

In another aspect that may be combined with any of the aspects herein, the workout files have a second control command subset that does not provide instructions for controlling the one or more actuators that selectively adjust the operating parameters of the moveable member.

In another aspect that may be combined with any of the aspects herein, the exercise device has a processing unit that is in communication with the one or more actuators and the receiving port.

In another aspect that may be combined with any of the aspects herein, the processing unit includes reference data that enables the processing unit to select the first control command subset from the workout file.

In another aspect that may be combined with any of the aspects herein, the reference data enables the processing unit to analyze the first control command subset and, if necessary, apply a sizing restriction to the first control command subset creating a restricted control command subset, such that the restricted control command subset provides instructions for controlling the one or more actuators that selectively adjust the operating parameters of the moveable member within the limited range.

In another aspect that may be combined with any of the aspects herein, the sizing restriction applied by the processing unit is a scaling sizing restriction.

In another aspect that may be combined with any of the aspects herein, the sizing restriction applied by the processing unit is a capping sizing restriction.

In another aspect that may be combined with any of the aspects herein, the workout file further includes motivational content.

In another aspect that may be combined with any of the aspects herein, the motivational content is synchronized with or reflective of the control commands within a workout file.

In another aspect that may be combined with any of the aspects herein, the reference data enables the processing unit to modify the motivational content.

In another aspect that may be combined with any of the aspects herein, the motivational content includes a video of terrain to be traversed during performance of an exercise In another aspect that may be combined with any of the aspects herein, the processing unit modifies the horizon line on the video so that the horizon line on the video remains synchronized with the restricted control command subset.

In another aspect that may be combined with any of the aspects herein, the processing unit modifies the playback speed of the video so that the playback speed of the video remains synchronized with the restricted control command subset.

In another aspect that may be combined with any of the aspects herein, the motivational content includes a graphical representation of a workout file profile.

In another aspect that may be combined with any of the aspects herein, the processing unit modifies the graphical representation of the workout file profile so that the workout file profile remains reflective of the restricted control command subset.

In another aspect that may be combined with any of the aspects herein, the motivational content includes projected biological metrics In another aspect that may be combined with any of the aspects herein, the processing unit modifies the projected biological metrics so that the projected biological metrics remain reflective of the restricted control command subset.

In another aspect that may be combined with any of the aspects herein, the workout file is a universal workout file and includes control command subsets for at least two different types of exercise devices.

In another aspect that may be combined with any of the aspects herein, the first subset of control commands may be modified by the processing unit based on user input.

In another aspect that may be combined with any of the aspects herein, the receiving port is a memory device drive.

In another aspect that may be combined with any of the aspects herein, a remote computer makes available at least one workout file that includes a first subset of control commands and a second subset of control commands.

In another aspect that may be combined with any of the aspects herein, a first exercise device has a first processing unit and one or more operating parameters that are selectively adjustable within a limited range, based on the first subset of control commands from the workout file.

In another aspect that may be combined with any of the aspects herein, the first processing unit includes reference data that allows the first exercise device to identify and execute the first subset of control commands.

In another aspect that may be combined with any of the aspects herein, a second exercise device has a second processing unit and one or more operating parameters that are selectively adjustable within a limited range based on the second subset of control commands from the workout file.

In another aspect that may be combined with any of the aspects herein, the second processing unit includes reference data that allows the second exercise device to identify and execute the second subset of control commands.

In another aspect that may be combined with any of the aspects herein, a method for controlling one or more exercise devices includes providing a workout file having a plurality of control command subsets, including a first subset of control commands and a second subset of control commands.

In another aspect that may be combined with any of the aspects herein, the method further includes providing an exercise device that has a processing unit and a first moveable member that is selectively adjustable within a limited range and that is adjustable based on the first subset of control commands.

In another aspect that may be combined with any of the aspects herein, the method further includes selecting the first subset of control commands from the plurality of control command subsets.

In another aspect that may be combined with any of the aspects herein, the method further includes adjusting the first moveable member based on the first subset of control commands.

In another aspect that may be combined with any of the aspects herein, the method further includes applying a sizing restriction to the first subset of control commands such that the control commands adjust the moveable member within the limited range.

In another aspect that may be combined with any of the aspects herein, the method further includes providing a second exercise device having a processing unit and a second moveable member that is selectively adjustable within a limited range and that is adjustable based on the second subset of control commands.

In another aspect that may be combined with any of the aspects herein, the method further includes adjusting the second moveable member based on the second subset of control commands.

DETAILED DESCRIPTION

The present invention provides methods, systems, and devices for providing workout files that are compatible with a plurality of different exercise devices. Exercise devices of the present invention are able to identify control commands within the workout file that are compatible with the exercise device. Exercise devices of the present invention may also apply a sizing restriction to the compatible control commands within the workout file such that the control commands adjust operating parameters of the exercise device within a limited range.

Figure 1:
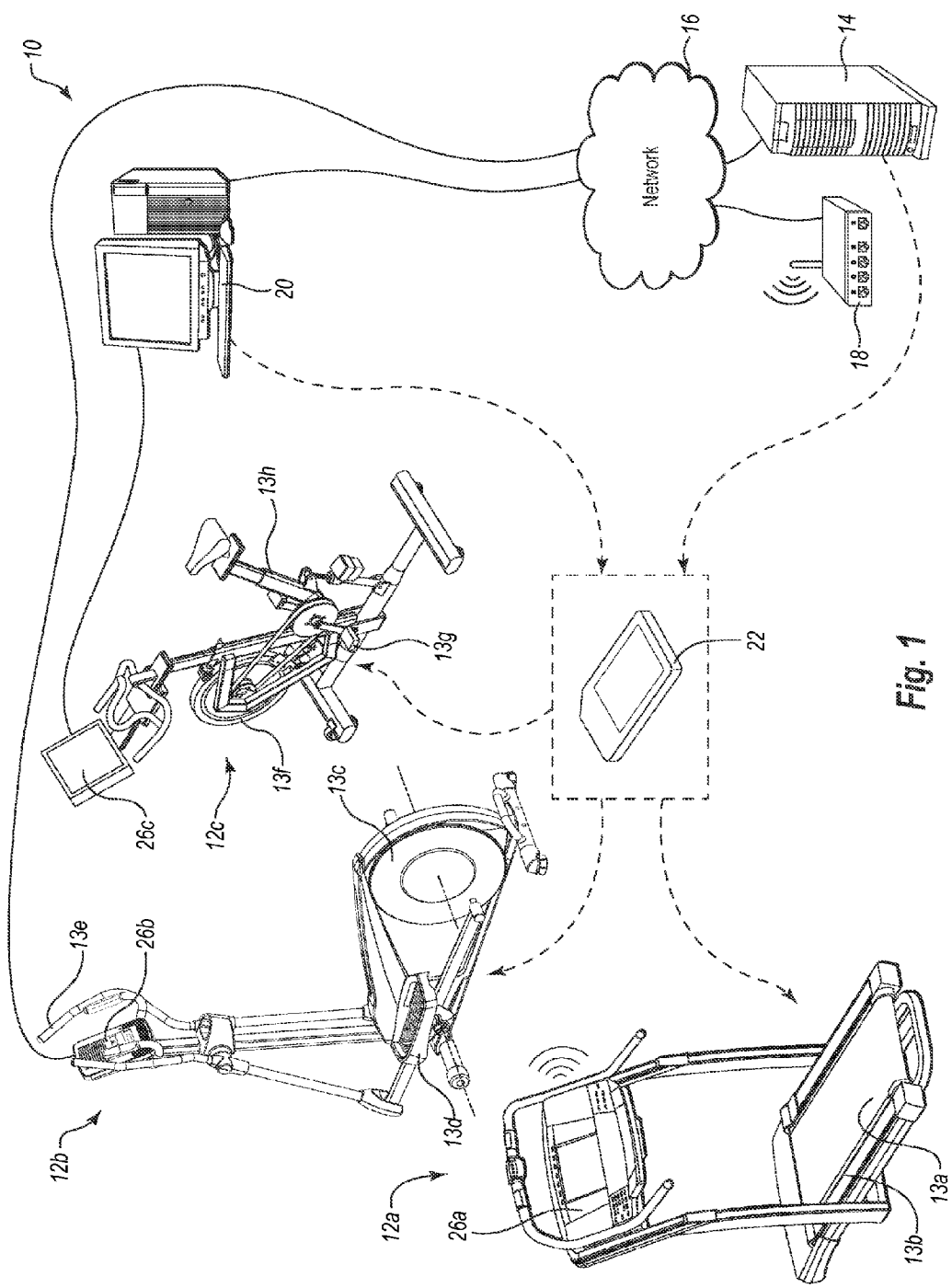
FIG. 1 illustrates an exercise system according to one embodiment of the present invention.

FIG. 1 illustrates an exercise system 10. Exercise system 10 includes exercise devices 12a-c, which have moveable members 13a-h, which move during performance of an exercise. Moveable members 13a-h have operating parameters that are selectively adjustable within a limited range. One or more actuators may selectively adjust the operating parameters of moveable members 13a-h within the limited range. Exercise devices 12a-c also include one or more receiving ports (see FIG. 2). Specifically, exercise devices 12a-c include wired connection ports, wireless connection ports, memory device drives, CD drives, DVD drives, disk drives, etc. Exercise devices 12a-c are capable of receiving data through these receiving ports.

Data received by exercise devices 12a-c through their receiving port(s) can include workout files. Workout files can comprise in whole or in part exercise programming, which may include control commands and motivational content. As described in more detail hereafter, control commands may provide instructions for adjusting the operating parameters (such as the speed, incline, difficulty level, time, distance, and the like) of a moveable member. Motivational content broadly refers to any video or visual material either alone or in combination with audio material, including dialog, narration, sound effects, and/or music. Control commands may or may not be synchronized with motivational content.

Exercise device 12a is illustrated as a treadmill. Exercise device 12a may include multiple different moveable members including a belt 13a and a deck 13b. Moveable members 13a-b include one or more operating parameters that are selectively adjustable within a limited range. One example of an operating parameter on exercise device 12a is the speed of belt 13a. Belt 13a may rotate at different speeds within a limited range. An actuator (see FIG. 2), for example a belt motor, may selectively adjust the speed at which belt 13a rotates within the limited range. Another example of an operating parameter on exercise device 12a is the inclination of deck 13b. Deck 13b may be selectively inclinable to different angles within a limited range. An actuator, for example an incline motor, may selectively adjust the incline of deck 13b within the limited range.

Exercise device 12b is illustrated as an elliptical machine. Exercise device 12b may include multiple different moveable members including a flywheel 13c, foot rails 13d, and arm rails 13e. During performance of an exercise on exercise device 12b, movement of foot rails 13d and arm rails 13e cause flywheel 13c to rotate. Moveable members 13c-e include one or more operating parameters that are selectively adjustable within a limited range. One example of an operating parameter on exercise device 12b is the amount of resistance applied to flywheel 13c. A differing amount of resistance can be applied to flywheel 13c to make the movement of foot rails 13d and arm rails 13e more or less difficult. An actuator, such as a brake, may be used to selectively adjust the amount of resistance that is applied to flywheel 13c. Another example of an operating parameter on exercise device 12b is the inclination of foot rails 13d. Foot rails 13d may be inclinable to different angles within a limited range. An actuator, such as an incline motor, may selectively adjust the incline of foot rails 13d within the limited range. Yet another example of an operating parameter on exercise device 12b is the stride length of foot rails 13d or arm rails 13e. The stride length of the foot rails 13d and/or arm rails 13e may be adjustable to different distances within a limited range. An actuator, for example a stride length motor, may selectively adjust the stride length of the foot rails 13d or arm rails 13e within the limited range.

Exercise device 12c is illustrated as an exercise bike. Exercise device 12c may include multiple different moveable members including a flywheel 13f, pedals 13g, and a frame 13h. During performance of an exercise on exercise device 12c, movement of pedals 13g cause flywheel 13f to rotate. These moveable members include one or more operating parameters that are selectively adjustable within a limited range. One example of an operating parameter on exercise device 12c is the amount of resistance applied to flywheel 13f. A differing amount of resistance can be applied to flywheel 13f to make rotation of the pedals 13g more or less difficult. An actuator, such as a brake, may be used to selectively adjust the amount of resistance that is applied to flywheel 13f within the limited range. Another example of an operating parameter on exercise device 12c is the configuration of frame 13h. Frame 13h may tilt forward, backward, or from side to side within a limited range. An actuator, such as tilt motor, may selectively adjust frame 13h within the limited range.

A communication system 14 (e.g., a remote computer or website) can provide data, including workout files, to exercise devices 12a-c through a network 16 or a portable memory device 22. Network 16, may be a local area network (LAN), wide area network (WAN), wireless network, packetized network, real-time network, and the like. Network 16 facilitates communication between exercise devices 12a-12c and communication system 14.

Connection between exercise devices 12a-12c and network 16 can be made via a variety of different communication line connections. For example, exercise device 12a is illustrated with a wireless receiving port and is capable of wireless communication with communication system 14 via network 16 through a wireless router 18. The wireless receiving port may also be receptive to communications via broadcast technology, including television broadcast over the airwaves, satellite, the Internet, DSL, G-Lite, infra-red (IR) technology, other high-speed data connections, or any other suitable wireless transmission technology or medium. Exercise device 12b includes a wired receiving port. Specifically, exercise device 12b is shown with a direct hardwire connection to network 16. Exercise device 12c also includes a wired receiving port. Specifically, exercise bike 12b is shown with a hardwire connection to personal computer 20, which has a hardwire connection with network 16. Thus, system 10 may allow for any type of connection between an exercise device 12 and network 16, whether wired or wireless.

Although each of the elements of system 10 are shown separated one from another, it may be appreciated by one skilled in the art that the hardware and/or software elements of the present invention may be incorporated within two or more elements. For example, personal computer 20 may be incorporated within exercise device 12a, exercise device 12b, or exercise device 12c.

A receiving port on any of exercise devices 12a-c could also be a memory device drive such as a USB port or a SD card drive. For example, exercise devices 12a-12c may each include a portable memory device drive that receives and is able to read portable memory device 22. Portable memory device 22 can receive workout files from communication system 14 via network 16 and personal computer 20. Alternatively, Portable memory device 22 can receive workout files directly from communication system 14.

Figure 2:
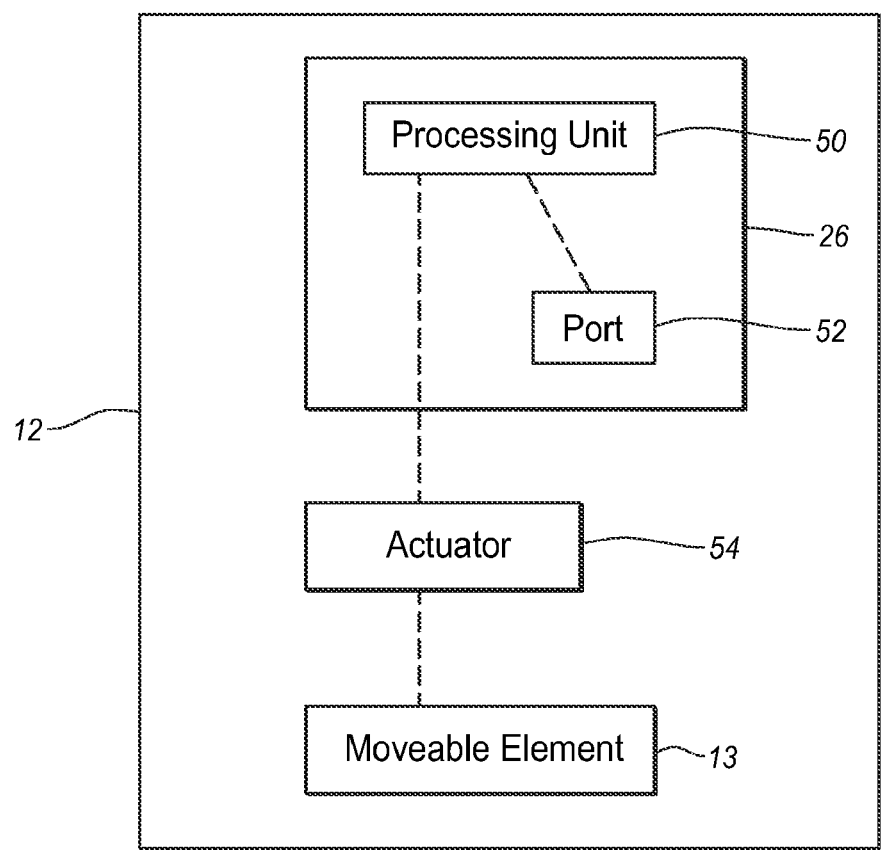
FIG. 2 illustrates a block diagram of exercise device components that can be used in connection with the present invention.

Exercise devices 12a-12c also include a processing unit (see FIG. 2). A processing unit can be a computer, a microprocessing unit, a microcontroller, state machine or other similar device that includes circuitry for controlling the operation of one or more features on an exercise device. For example, a processing unit on exercise device 12a may control the speed of belt 13a or inclination of deck 13b. A processing unit on exercise device 12b may control the actuators that adjust the resistance applied to flywheel 13c, or the inclination or stride length of foot rails 13d and/or arm rails 13e. A processing unit on exercise device 12c may control the actuators that adjust the resistance applied to flywheel 13f or the tilt of frame 13g. A processing unit may be located within the console of an exercise device or within another part of an exercise device. Alternatively, a processing unit may be external from the exercise device. A processing unit may include reference data, code, software, or other data or operating instructions for performing its function and executing commands. Reference data may include the limited range of operating parameters of a moveable member.

Exercise devices 12a-12c also include control consoles 26a-26c. Control consoles 26a-26c may include one or more interface devices. Interface devices may be either input devices or output devices. Input devices enable a user to manually input and vary the operating parameters of the moveable member on the exercise device. Examples of input devices include but are not limited to speed controls, incline controls, resistance controls, time controls, distance controls, a start button, a stop or pause button, and heart rate controls. These input devices may take the form of one or more buttons, switches, rheostats, potentiometers, touch sensitive controls, voice activated controllers, and the like.

In general, output devices provide information, either visually or audibly, to a person performing an exercise on exercise devices 12a-12c. This information, which can be referred to broadly as "motivational content," can include information regarding the exercise device. For example, an output device may provide information representative of the operating parameters of the exercise device, such as the speed, incline, resistance level, duration of workout, elevation climbed, etc. This information may be provided numerically, graphically, or through combinations thereof. To provide a more realistic experience, output devices may provide a representation of a trail, road, or path to be traversed by a person performing an exercise. Motivational content can also include information regarding the person exercising on the exercise device, such as biometric information. For example, an output device may provide information representative of the user's pulse, calories burned, blood pressure, etc.

Examples of output devices through which motivational content may be provided include but are not limited to speakers, video displays, liquid crystal display (LCD), light emitting diodes (LEDs), cathode ray tube (CRT) displays, electroluminescent displays (ELD), gas-plasma displays, thin film transistor (TFT) displays, virtual reality (VR) displays, and the like.

FIG. 2 illustrates a block diagram showing components that may be included in an exercise device 12, such as exercise devices 12a-c. For example, exercise device 12 may include a processing unit 50, a receiving port 52, an actuator 54, and a moveable member 13. Processing unit 50 is communicatively connected to the receiving port 52 and may be included within a console 26. Processing unit 50 is also communicatively connected to actuator 54. In response to control commands from processing unit 50, actuator 54 selectively adjusts one or more operating parameters of moveable member 13 within a limited range.

Data, including workout files, can be received by exercise device 12 through receiving port 52. As stated previously, workout files can include one or more control commands as well as motivational content. Control commands that provide control instructions to an exercise device (for example, a treadmill, elliptical machine, or exercise bike) may be referred to as a "control command subset." Thus, a control command subset may comprise a plurality of control commands that include, for example, control commands for a belt motor, an incline motor, and other actuators. In addition to actuator control commands, control command subsets may further include distance control commands and time control commands. These commands may provide a series of actuator control commands for execution at specific times or at specific distances. For example, a workout file may provide a control command for an actuator to be at a certain level for a specific amount of time or for a specific distance.

Using these control command subsets, processing unit 50 may control actuator 54 on an exercise device in the sequence and at the times or distances specified by the commands. For example, actuator control commands that provide a processing unit with commands for controlling a belt motor, incline motor, or other actuator may be included in a control command subset for exercise device 12a. Actuator control commands that provide a processing unit with commands for controlling a flywheel brake, incline motor, stride length motor, or other actuator may be included in a control command subset for exercise device 12b. Actuator control commands that provide a processing unit with commands for controlling a flywheel brake or other actuator may be included in a control command subset for exercise device 12c.

Actuator control commands can be received for different time segments or distance segments of an exercise program. For example, a ten minute exercise program may have twenty different control commands that provide a processing unit with a different command for controlling an actuator every thirty seconds. Alternatively, a ten mile exercise program may have twenty different control commands that provide a processing unit with a different command for controlling an actuator every half mile. Exercise programs may be of any duration or distance and different control commands may be received at any time or distance during the program.

These control command subsets may be executed by exercise device 12 or processing unit 50 in a number of different ways. For example, the control commands may be stored into a read/write memory that is included in processing unit 50. Alternatively, the control command subsets may be streamed to the exercise device. The control commands may also be received and/or executed from a portable memory device, such as a USB memory stick or an SD card.

Workout files, according to the present invention, may include a plurality of control command subsets that provide instructions for different types of exercise devices. For example, a workout file may include a first control command subset that includes control commands for controlling a belt motor and an incline motor on a treadmill. The workout file may also include a second control command subset that includes control commands for controlling a brake and a tilt motor on an exercise bike.

Workout files that include control command subsets that provide instruction for different types of exercise devices (e.g., treadmills, elliptical machines, exercise bikes) may be referred to herein as "universal workout files." When a universal workout file is received through receiving port 52 of an exercise device, the processing unit 50 recognizes the control command subset that is compatible with the actuators included on the exercise device. For example, reference data within processing unit 50 may be used to recognize the compatible control command subset. Once recognized, processing unit 50 may select the control command subset that is compatible with the actuators included on the exercise device. Processing unit 50 may ignore the control command subsets that are not compatible with actuators on the exercise device.

For example, a workout file that includes a control commands for controlling both the speed of a belt on a treadmill and the resistance applied to a flywheel on an exercise bike may be received by exercise device 12a and exercise device 12c. The processing unit within exercise device 12a recognizes and is able to select the control command subset that provides instructions for belt speed, while ignoring the control command subset that provides instructions for flywheel resistance. Similarly, the processing unit within exercise device 12c is able to select the control command subset that provides instructions for flywheel resistance, while ignoring the control command subset that provides instructions for belt speed.

In addition to recognizing and selecting the compatible control command subsets, processing unit 50 may also apply a sizing restriction to actuator control commands before the control commands can be executed by the exercise device. As with recognizing the compatible control command subsets, processing unit 50 may use reference data to determine whether a sizing restriction is necessary and, if so, apply the sizing restriction. Application of a sizing restriction to compatible control commands may be necessary due to the fact that the moveable members on exercise devices have operating parameters that are adjustable only within a limited range. Thus, even if two exercise devices have the same type of actuator (i.e., both have belt motors), a workout file that provides control commands for that actuator may not be compatible with both devices.

For example, a workout file may include an actuator control command that instructs a processing unit to set the speed of the belt motor on a treadmill to fifteen miles per hour. As long as fifteen miles per hour is within the operating parameters of the belt motor, the processing unit would be able execute this command. However, fifteen miles per hour is not within the operating parameters of all belt motors. Some belt motors may only achieve a belt speed of ten miles per hour, or less. To the extent a belt motor is not able to achieve a belt speed of fifteen miles per hour, processing unit 50 would apply a sizing restriction to the control commands such that the control commands after a sizing restriction has been applied fall within the limited range of operating parameters of the treadmill. Once processing unit 50 has applied a sizing restriction to a control command subset, the resized control command subset is referred to herein as a "restricted control command subset."

Figure 3A:
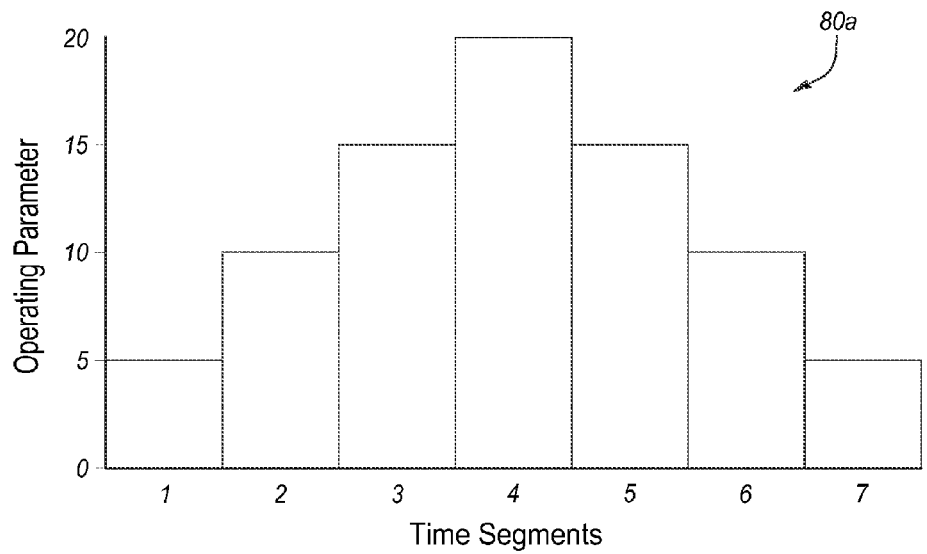
FIG. 3A illustrates graphically a profile of a workout file.
Figure 3B:
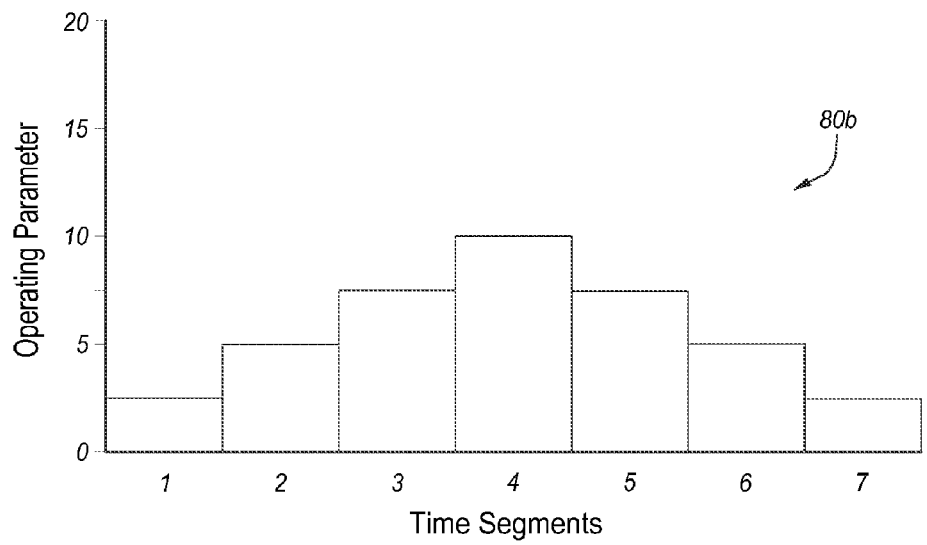
FIG. 3B illustrates graphically a profile of a workout file after application of a sizing restriction to the workout file.

Processing unit 50 can resize actuator control commands in different ways. For example, processing unit 50 may scale the size of the actuator control commands. FIG. 3A provides a graphical representation of a workout file profile 80*a*, with operating parameters on the y-axis and time segments in the x-axis. The operating parameters and time segments illustrated in FIG. 3A are representative of a series of timed control commands that may be included in a workout file. As can be seen in FIG. 3A, the highest operating parameter in workout file profile 80*a* is twenty. FIG. 3B illustrates workout file profile 80*a* of FIG. 3A after a scaling restriction has been applied by processing unit 50. As can be seen in FIG. 3B, each of the operating parameters has been reduced or scaled such that the highest operating parameter in the new workout file profile 80*b* is ten. In other words, to bring the highest operating parameter within the limited range, the highest operating parameter was reduced or scaled by fifty percent. In the present embodiment, all of the other operating parameters were also scaled by fifty percent.

With the sizing restriction applied, workout file profile 80*b* of FIG. 3B can now be executed by an exercise device that has a moveable member with an operating parameter limit of ten or less. This scaling adjustment may be performed by processing unit 50 automatically based on the limited range of operating parameters of the exercise device. Alternatively, this scaling adjustment may be performed by processing unit 50 based on user input.

Figure 4A:
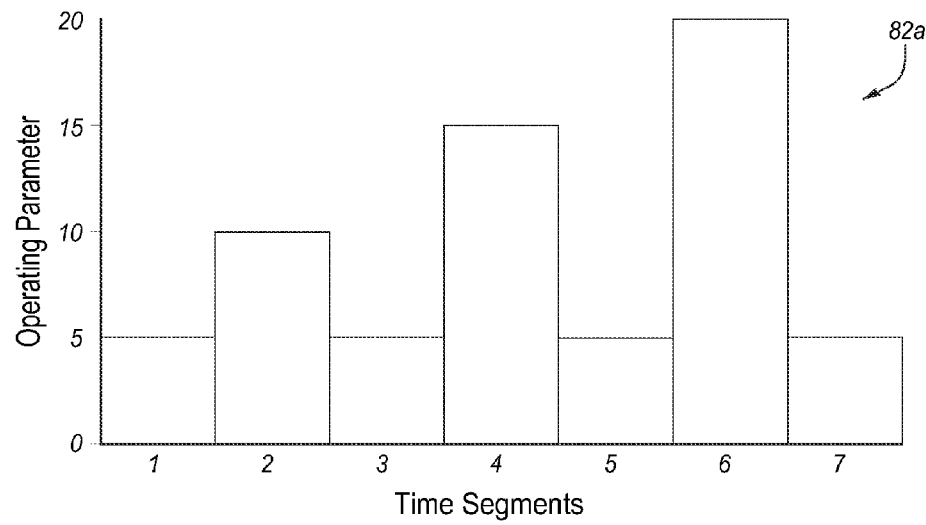
FIG. 4A illustrates graphically a profile of a workout file.
Figure 4B:
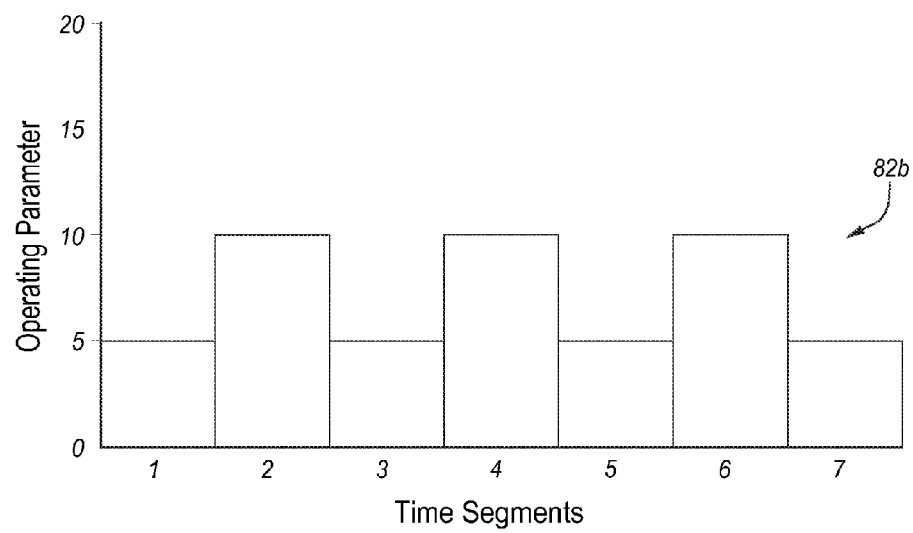
FIG. 4B illustrates graphically a profile of a workout file after application of a sizing restriction to the workout file.

Processing unit 50 may also resize actuator control commands by placing a cap on the size of actuator control commands. FIG. 4A provides a graphical representation of a workout file profile 82*a*, with operating parameters on the y-axis and time segments in the x-axis. As can be seen in FIG. 4A, exercise program 82*a* includes operating parameters of fifteen and twenty in time segments four and six, respectively. FIG. 4B illustrates workout file profile 82*a* of FIG. 4A after a capping restriction has been applied by processing unit 50. As can be seen in FIG. 4B, the highest operating parameter in the new workout file profile 82*b* is ten. That is, the operating parameter in time segments four and six were reduced down to ten each. As a result, workout file profile 82*a* has a maximum operating parameter level of ten. Workout file profile 82*b* of FIG. 4B can now be executed by an exercise device that has a moveable member with an operating parameter limit of ten or less. This capping adjustment may be applied by processing unit 50 to any control command that instructs actuator movement outside the limited range of operating parameters for a moveable member. This capping adjustment may be performed by processing unit 50 automatically based on the limited range of the operating parameters of the exercise device. Alternatively, this capping adjustment may be performed by processing unit 50 based on user input.

While a sizing restriction may be necessary due to the limited range of the operating parameters of a moveable member, sizing restrictions may also be performed in response to user input. For example, a user, using an input device, may scale actuator control commands in a workout file by a desired percentage. Referring back to FIGS. 3A and 3B, the actuator control commands of workout file profile 80*b* are fifty percent of the actuator control commands of workout file profile 80*a*. Thus, workout file profile 80*b* may be the result of a user's selection of fifty percent of original workout file profile 80*a*. Other percentages of the original workout file may be selected. For example, a user may want to scale the actuator control commands by seventy-five percent, ninety percent, etc. A user may also want to increase the actuator control commands of an original workout file by selecting, for example, one-hundred and ten percent or another percentage above one-hundred percent.

Figure 5A:
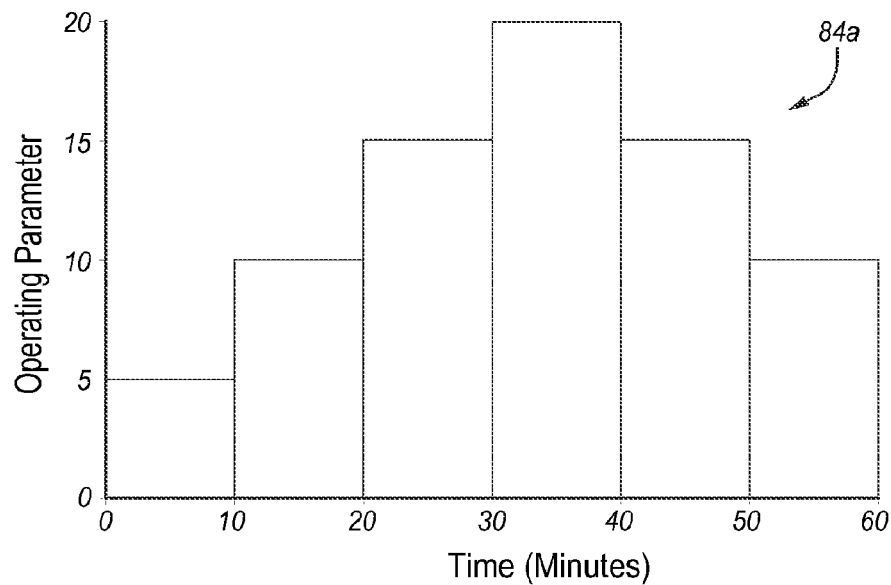
FIG. 5A illustrates graphically a profile of a workout file.
Figure 5B:
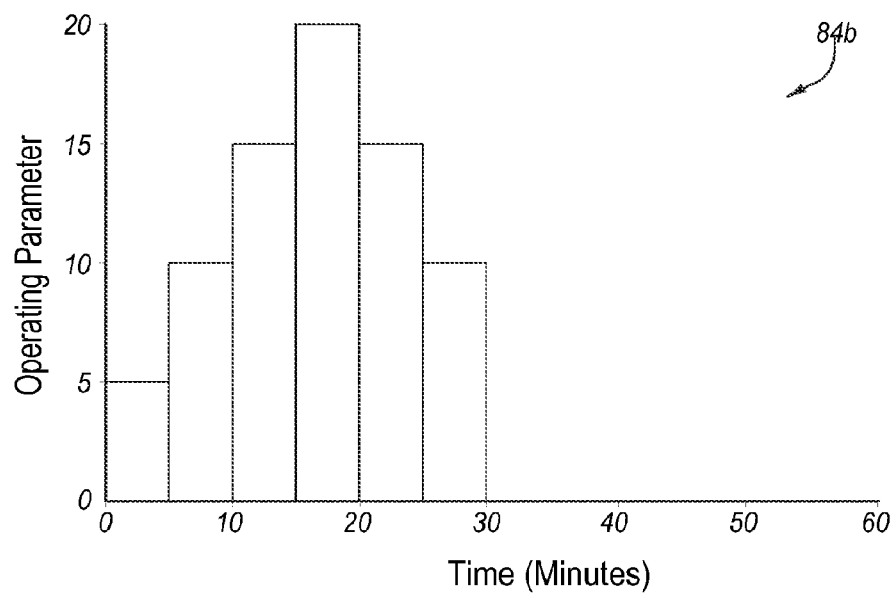
FIG. 5B illustrates graphically a profile of a workout file after application of a sizing restriction to the workout file.

In addition to size restrictions applied to actuator control commands, processing unit 50 may also modify or adjust the time commands associated with actuator control commands, to the extent time commands are included in the workout file. For example, FIG. 5A provides a graphical representation of workout file profile 84*a*, with actuator control commands on the y-axis and time, in minutes, in the x-axis. As can be seen in FIG. 5A, the total time duration for workout file profile 84*a* is sixty minutes. Different actuator control commands are provided at ten minute intervals creating six different time segments, each ten minutes long. FIG. 5B illustrates workout file profile 84*b* after a time restriction has been applied by processing unit 50. As can be seen in FIG. 5B, the total time duration for workout file profile 84*b* is thirty minutes. The duration of each of the six time segments has been reduced by fifty percent. Thus, instead of six time segments of ten minutes each as in workout file profile 84*a*, workout file profile 84*b* has six time segments of five minutes each. The time associated with an workout file profile may be modified based on user input. For example, the time modification reflected in FIGS. 5A and 5B may be the result of a user having input a desired workout time of thirty minutes.

Figure 6A:
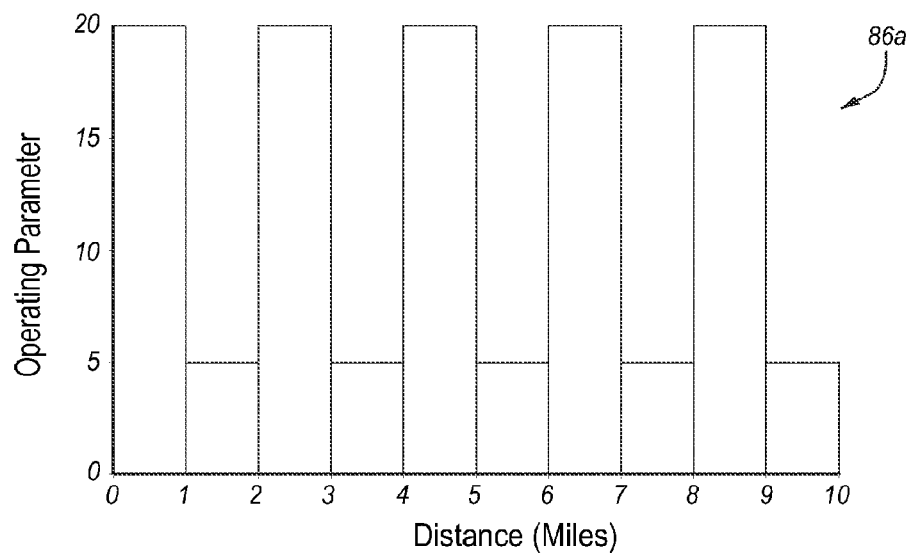
FIG. 6A illustrates graphically a profile of a workout file.
Figure 6B:
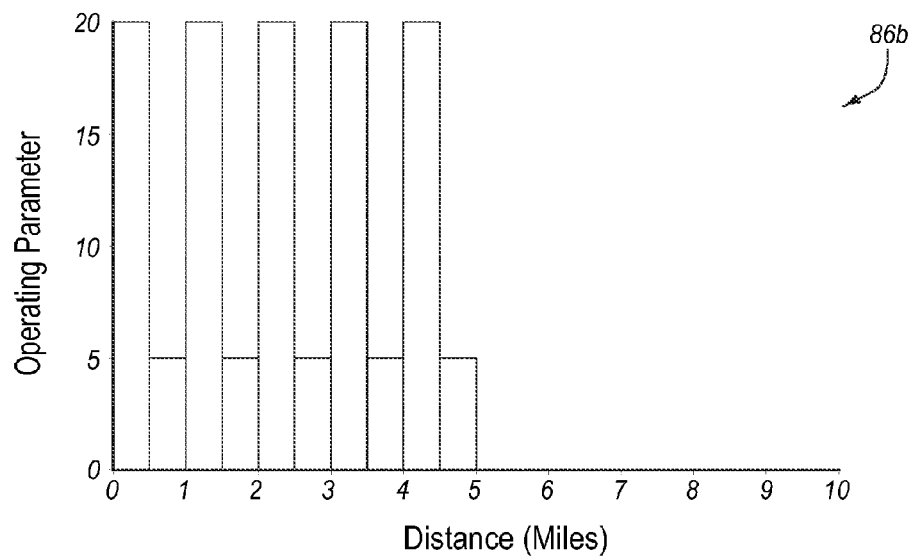
FIG. 6B illustrates graphically a profile of a workout file after application of a sizing restriction to the workout file.

Processing unit 50 may also modify or adjust the distance commands associated with actuator control commands, to the extent distance commands are included in the workout file. For example, FIG. 6A provides a graphical representation of an workout file profile 86*a*, with actuator control commands on the y-axis and distance, in miles, in the x-axis. As can be seen in FIG. 6A, the total distance of workout file profile 86*a* is ten miles. Different actuator control commands are provided at one mile intervals creating ten different distance segments. FIG. 6B illustrates workout file profile 86*b* after a distance restriction has been applied by processing unit 50. As can be seen in FIG. 6B, the total distance of workout file profile 86*b* is five miles. The distance of each of the ten distance segments has been reduced by fifty percent. Thus, instead of ten distance segments of one mile each as in workout file profile 86*a*, workout file profile 86*b* has ten distance segments of one-half mile each. The distance associated with an workout file profile may be modified based on user input. For example, the distance modification reflected in FIGS. 6A and 6B may be the result of a user having input a desired workout distance of five miles.

Workout files may also include motivational content. The motivational content may be synchronized with or reflective of the control commands within a workout file. For example, motivational content may include a video of terrain to be traversed that is displayed to a user. This video may be synchronized with control commands such that the control commands correspond to what is shown on the video. This may be accomplished by adjusting the horizon line on the video as an incline motor changes the incline on an exercise device. This may also be accomplished by increasing the rate at which the video is played back as a belt motor changes the speed of a belt on an exercise device.

Motivational content may also include a graphical representation of a workout file profile, such as those that are illustrated in FIGS. 3A-6B. This graphical representation of a workout file profile may be reflective of the control commands in the workout file such that the workout file profile shows the sequence of operating parameter adjustments in the workout.

Motivational content may further include projected biological metrics. These biological metrics may include but are not limited to caloric expenditure, metabolic equivalent of task, and carbohydrate expenditure. Biological metrics may be reflective of the control commands and the actual biological metrics that are anticipated for a person that performs and exercise that implements the control commands.

Processing unit 50 may adjust, alter, or otherwise modify the motivational content that is included in a workout file. Motivational content that has been modified by processing unit 50 is referred to herein as "modified motivational content." Motivational content may be modified by processing unit 50 in connection with or independently from modifications made to actuator control commands, time control commands, or distance control commands. Motivational content may be modified by processing unit 50 so that the modified motivational content remains synchronized with or reflective of a restricted control command subset.

Figure 7A:
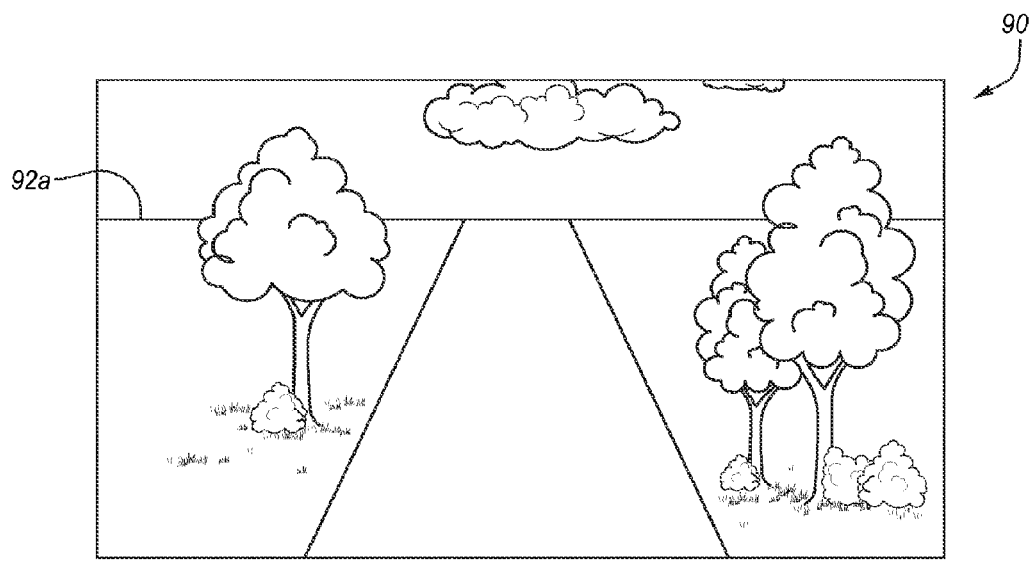
FIG. 7A illustrates a frame from a video showing terrain to be traversed by the user during performance of an exercise.
Figure 7B:
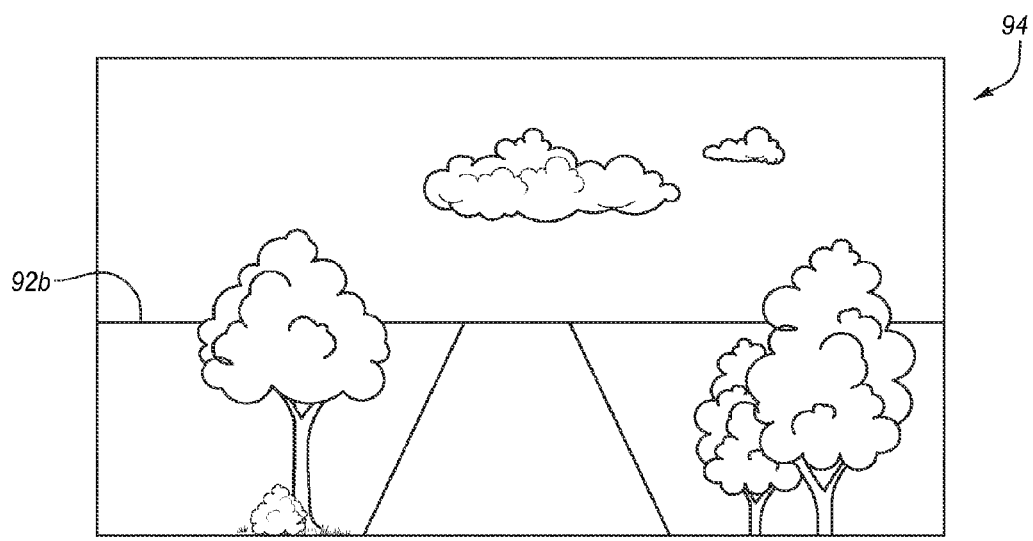
FIG. 7B illustrates a frame from a video showing terrain to be traversed by the user during performance of an exercise after an adjustment to the horizon line.

For example, an adjustment to a control command in a workout file may cause an adjustment to a video of terrain to be traversed that is displayed to the user. FIG. 7A illustrates a frame 90 from a video showing terrain to be traversed by the user during performance of an exercise. Frame 90 includes a horizon line 92*a*. Frame 90 illustrated in FIG. 7A may be shown on a display incorporated on the console of an exercise device or in another location. FIG. 7B illustrates a frame 94 from the video showing terrain to be traversed by the user during performance of an exercise after an adjustment to the horizon line on the video. As can be seen, the horizon line 92*a* shown in FIG. 7A is higher than the horizon line shown 92*b* in FIG. 7B. Processing unit 50 may modify the horizon line position so that the horizon line in a video remains synchronized with the inclination executed by the actuators of an exercise device. For example, the horizon line adjustment shown in FIGS. 7A and 7B can be made in connection with a modification to control commands which decreases the inclination implemented on a treadmill or elliptical machine.

In addition, if actuator control commands for a belt motor on a treadmill are modified, the playback speed of the video could be modified so that the video is played at a rate that corresponds with the speed that the belt is rotating. For example, if processing unit 50 cuts actuator control commands for a belt motor in half, processing unit 50 may also double the playback speed of a video so that the video remains synchronized with the restricted control command subset.

An adjustment to actuator control commands in a workout file may also cause an adjustment to a graphical representation of a workout file profile. For example, if processing unit 50 modifies control commands in a workout file, processing unit 50 may also modify a graphical representation of the workout file profile so that the workout file profile remains reflective of the restricted control command subset.

Further, an adjustment to actuator control commands in a workout file may also cause an adjustment to projected metrics for a user performing the exercise. For example, if control commands in a workout file are modified, processing unit 50 may also modify the projected metrics so that the projected metrics reflect the restricted control command subset.

Finally, in addition to motivational content, other control commands may be adjusted in response to adjustments to actuator control commands. For example, a workout file may include instructions for fan speed. If actuator control commands for the belt speed on a treadmill are modified, processing unit 50 may also modify control commands for the speed of a fan may so that the fan speed remains reflective of the belt speed, thus creating a more realistic workout experience for a user.

Figure 8:
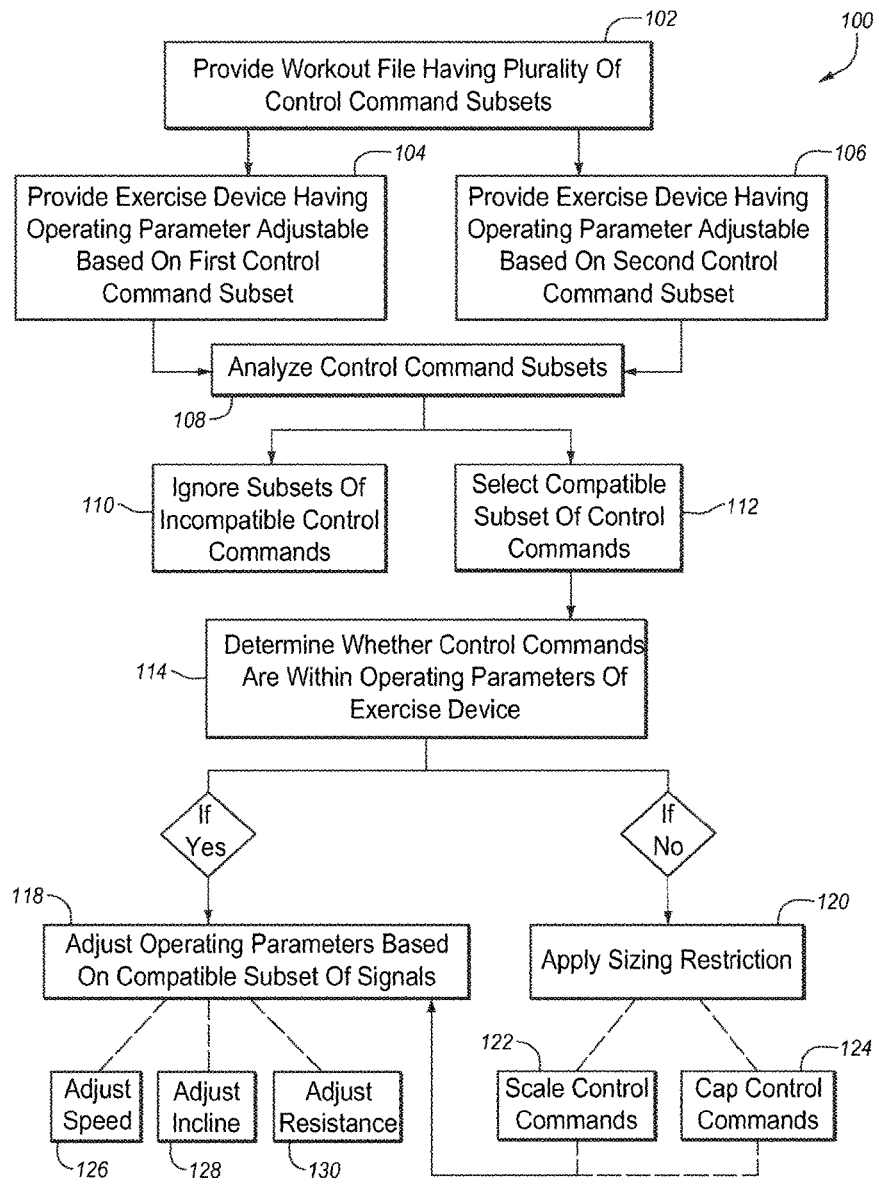
FIG. 8 illustrates steps that may be implemented in a method for controlling an exercise device.

The present invention also includes a method 100 for controlling an exercise device. FIG. 8 illustrates steps that may be implemented in method 100 for controlling an exercise device. In a first step 102, a workout file having a plurality of control command subsets, including a first subset of control commands and a second subset of control commands, is provided. In step 104, a first exercise device having at least one moveable member that is selectively adjustable within a limited range and that is adjustable based on the first subset of control commands is provided. The method of the present invention may be limited to a single exercise device. However, a method for controlling multiple exercise devices is disclosed. For example, method 100 includes steps for controlling a second exercise device. In step 106, a second exercise device having at least one moveable member that is selectively adjustable within a limited range and that is adjustable based on the second subset of control commands is provided.

In step 108, the first and second exercise devices each analyze the control command subsets included in the workout file. Control commands that are incompatible with each exercise device are ignored in step 110, while the compatible subset of control commands is selected in step 112. For example, if the first exercise device is a treadmill, the processing unit of the treadmill would ignore control command subsets for a flywheel brake and would select the control command subset for belt speed. If the second exercise device is an exercise bike, the processing unit of the exercise bike would ignore control command subset for belt speed and would select the control command subset for a flywheel brake.

In step 114, the first and second exercise devices each determine whether the selected control commands are within the limited range of the operating parameters of each machine's respective moveable members. If the selected control commands are within the operating parameters of each machine's respective moveable members, then each exercise device adjusts the operating parameters based on the compatible and selected subset of control commands in step 118.

Alternatively, if one or more control commands are outside the limited range of the operating parameter of the machine's moveable member, then a sizing restriction is applied in step 120. Sizing restrictions can be based on a scaling function (step 122) or a capping function (step 124), as those restrictions have been described hereinabove. Alternatively, a different sizing restriction could be applied to reduce the size of at least the control commands that are outside the operating parameter ranges of the exercise devices. Once a sizing restriction has been applied, then the exercise device adjusts the operating parameters based on the compatible subset of control commands in step 118.

Figure 9:
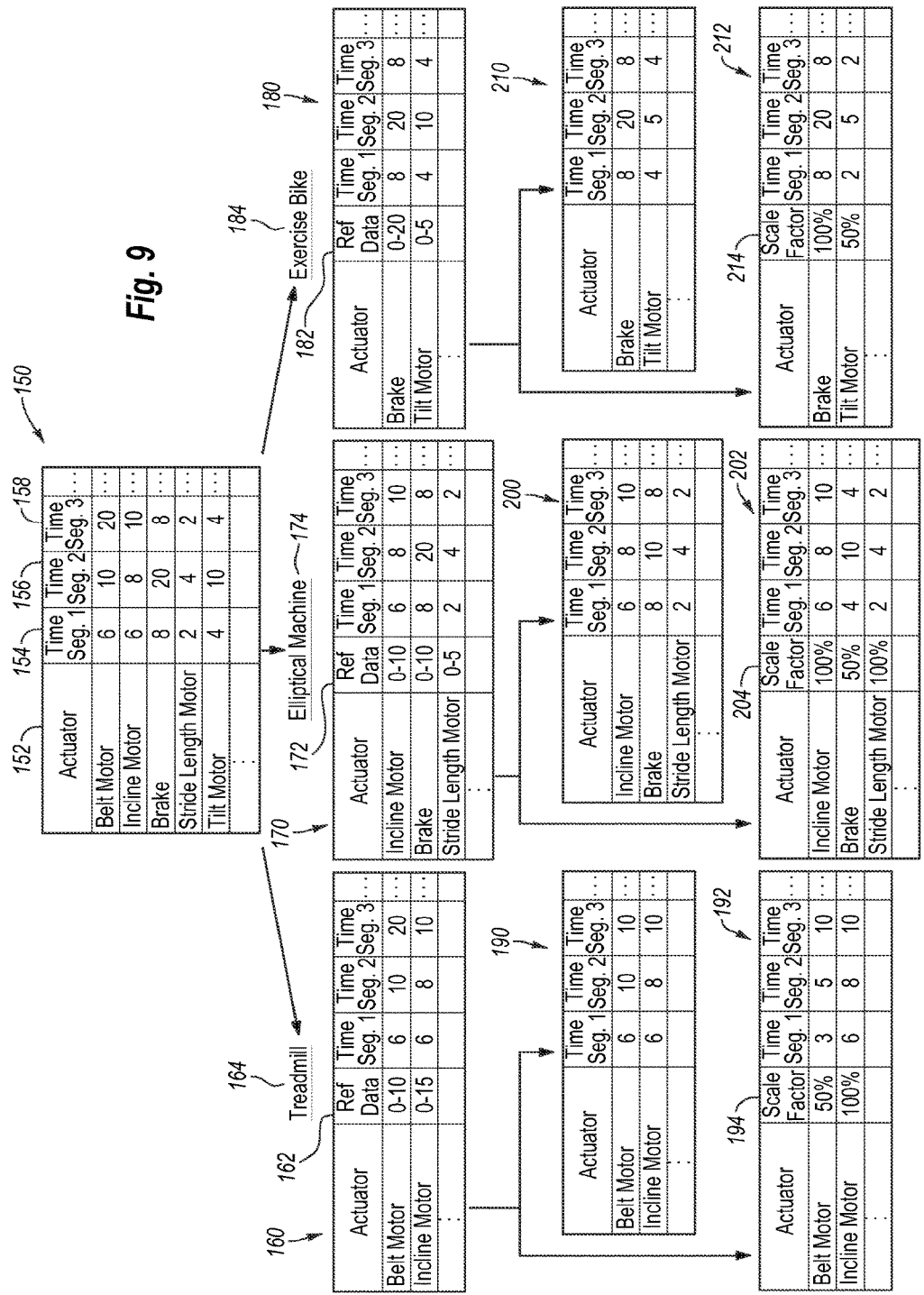
FIG. 9 illustrates tables arranged in a schematic representation of an implementation of the present invention.

FIG. 9 illustrates tables that include components of the present invention. For example, FIG. 9 illustrates a table 150, which identifies data that may be included in a workout file. The workout file illustrated in table 150 includes control commands that provide instructions for controlling the actuators 152 that selectively adjust the operating parameters of multiple moveable members during different time segments 154, 156, 158. More specifically, the workout file illustrated in table 150 includes control commands that provide instructions for controlling a belt motor, an incline motor, a brake, a stride length motor, and a tilt motor. Because these actuators correspond to different exercise devices, the workout file illustrated in table 150 is a universal workout file. A workout file may include instructions for controlling actuators in addition to or fewer than those explicitly identified in table 150.

The workout file illustrated in table 150 also includes three time segments 154, 156, and 158. Control commands for each of the actuators are provided for each of the time segments 154, 156, 158. Specifically, with regard to the belt motor, a control command of six is provided for time segment one 154, a control command of ten is provided for time segment two 156, and a control command of twenty is provided for time segment three 158. These control commands may represent a speed in miles per hour or another unit. Control commands are also provided for each time segment for the incline motor, brake, stride length motor, and tilt motor. The control commands for the incline motor may represent an angle, for example, degrees from horizontal. The control commands for the brake may represent a frictional resistance in Newtons or another unit. The control commands for the stride length motor may represent a distance or length in inches or another unit. The control commands for the tilt motor may represent an angle, for example, degrees from vertical. Workout file 150 may include time segments in addition to or fewer than those explicitly identified.

FIG. 9 also illustrates tables (160, 170, 180), which include control command subsets taken from the workout file in table 150. Specifically, table 160 includes a control command subset for a treadmill 164. For example, the control command subset illustrated in table 160 includes control commands from the workout file in table 150 that provide instructions for controlling a belt motor and an incline motor. Table 160 also includes reference data 162 that identifies the limited range of operating parameters for the actuators on treadmill 164. For instance, in the illustrated embodiment the belt motor has a range of operating parameters of zero to ten miles per hour and the incline motor has a range of operating parameters of zero to fifteen degrees/% grade. As can be seen, the workout file notably includes a belt motor control command of 20 miles per hour, which is outside the belt motor's range of operating parameters and which will be discussed in greater detail below.

Table 170 includes a control command subset for an elliptical machine 174. For example, the control command subset illustrated in table 170 includes control commands from the workout file in table 150 that provide instructions for controlling an incline motor, a brake, and a stride length motor. Table 170 also includes reference data 172 that identifies the limited range of operating parameters for the actuators on elliptical machine 174. Specifically, the incline motor has a range of operating parameters of zero to ten degrees and the brake has a range of operating parameters of zero to ten Newtons. The stride length motor has a range of operating parameters of zero to five inches. As can be seen, the workout file includes a brake control command of 20, which is outside the brake's operating parameter range of zero to ten Newtons.

Table 180 includes a control command subset for an exercise bike 184. For example, the control command subset illustrated in table 180 includes control commands from the workout file in table 150 that provide instructions for controlling a brake and a tilt motor. Table 180 also includes reference data 182 that identifies the limited range of operating parameters for the actuators on exercise bike 184. Specifically, the brake has a range of operating parameters of zero to twenty Newtons. The tilt motor has a range of operating parameters of zero to five degrees. As can be seen, the workout file includes a tilt motor control command of 10, which is outside the tilt motor's operating parameter range of zero to five degrees.

FIG. 9 also illustrates tables (190, 192, 200, 202, 210, 212), which include restricted control command subsets. Specifically, table 190 illustrates the control command subset of table 160 after application of a capping sizing restriction. As can be seen in table 190, the belt motor control commands have been capped such that each control command is within the belt motor's range of operating parameters. Table 192 illustrates the control command subset of table 160 after application of a scaling sizing restriction. Table 192 identifies the scaling factors that are applied to the belt motor control commands. These scaling factors may be stored in the processor of the exercise device or could be calculated by the processor based on the control commands included in the workout file and the reference data. Scaling factors applied to control commands for each actuator may be the same or different. As can be seen in table 192, after application of the scaling factors, each belt motor control command is within the belt motor's range of operating parameters.

Table 200 illustrates the control command subset of table 170 after application of a capping sizing restriction. As can be seen in table 200, the brake control commands have been capped such that each control command is within the brake's range of operating parameters. Table 202 illustrates the control command subset of table 170 after application of a scaling sizing restriction. Table 192 identifies the scaling factors that are applied to the brake control commands. As can be seen in table 192, after application of the scaling factors, each brake control command is within the brake's range of operating parameters.

Table 210 illustrates the control command subset of table 180 after application of a capping sizing restriction. As can be seen in table 210, the tilt motor control commands have been capped such that each control command is within the tilt motor's range of operating parameters. Table 212 illustrates the control command subset of table 180 after application of a scaling sizing restriction. Table 192 identifies the scaling factors that are applied to the tilt motor control commands. As can be seen in table 192, after application of the scaling factors, each tilt motor control command is within the tilt motor's range of operating parameters.

INDUSTRIAL APPLICABILITY

In general, the present invention relates to workout files that include control commands for controlling the actuators on a plurality of different exercise devices. Exercise devices of the present invention are able to receive, recognize, select, resize (if necessary) and execute compatible control commands while ignoring incompatible control commands. Exercise devices that are able to recognize and select compatible control command subsets allow a single universal workout file to be used by a variety of different exercise devices. This eliminates the need for consumers to obtain workout files that are uniquely designed for their type of exercise device. For example, a "Fat Burn" workout file could be stored onto a single SD card and be executed by a treadmill, elliptical machine, exercise bike, and other exercise devices.

While the invention has been described in the context of motorized treadmills, stationary exercise cycles, and elliptical machines, one of skill in the art will understand that the invention is not limited to any particular type of exercise device. To the contrary, the present invention can be readily adapted to any motorized device or any other device that utilizes motors, solenoids, or any other electrically driven actuators to control any operating parameter of a moveable member on an exercise device. For example, exercise devices may include treadmills, exercise bikes, Nordic style skiers, rowers, steppers, hikers, climbers, elliptical machines, and striding exercise machines. Operating parameters may include but are not limited to belt speed, resistance, incline, stride length or other similar operating parameter. A moveable member can be any part of an exercise device that moves during the performance of an exercise on that device. An actuator may be any device that selectively adjusts the operating parameters of a moveable member within the limited range.

Exercise devices of the present invention may obtain a workout file through one or more receiving ports. Exercise devices of the present invention may receive these workout files through the receiving ports and from any remote source, including but not limited to portable storage devices or from a remote communication system. The workout file may include only control commands. Alternatively, the workout file may contain both control commands and motivational content.

Control command subsets in the workout file may provide instructions to exercise device processing units for controlling actuators (for example, a belt motor). Workout files of the present invention may include a plurality of control command subsets. For example, a workout file may include a control command subset for controlling a belt motor, as well as other control command subsets for controlling an incline motor, a flywheel brake, and other actuators found on exercise devices.

Exercise devices of the present invention may include processing units that identify the control command subsets that provide instructions for controlling the actuators of the exercise device. Processing units may ignore control command subsets that provide instructions for controlling actuators that are not a part of the exercise device. For example, a treadmill processing unit may identify or recognize a control command subset that provides instructions for controlling a belt motor while ignoring control command subsets for controlling a flywheel brake. Processing units may include reference data or other software for identifying the relevant control command subset(s).

Once a processing unit has identified the relevant control command subsets within a workout file, the processing unit analyzes the control commands within the subset. The processing unit determines whether the control commands provide instructions for controlling the actuator within the limited range of the operating parameters of the moveable member. For example, a treadmill may include a belt motor that is only able to achieve a belt speed of up to ten miles per hour. Thus, the operating parameters of the belt have a limited range of zero to ten miles per hour within which it may be selectively adjusted by a belt motor.

To the extent that the processing unit determines that there is a control command that provides instructions for controlling an actuator outside of the limited range of the moveable member's operating parameters, the processing unit applies a sizing restriction to the control command(s), thereby creating a restricted control command subset. The processing unit may apply a sizing restriction to just the control command(s) that are outside of the limited range of moveable member's operating parameters. For example, the processing unit may simply cap the control command(s) that are outside of the limited range of operating parameters. For example, if a treadmill includes a belt motor that is only able to achieve a belt speed of ten miles per hour, any control command within the workout file may be capped at ten miles per hour.

Alternatively, the processing unit may apply a sizing restriction that scales all of the control commands within a workout file such that each of the control command provide instructions for controlling an actuator within the limited range of operating parameters of the moveable member. For example, if a treadmill includes a belt motor that is only able to achieve a belt speed of ten miles per hour and a control command provides instruction for setting the belt motor to twenty miles per hour, the processing unit may scale all of the control commands within the subset by fifty percent.

To the extent that the processing unit applies a sizing restriction to one or more control commands, the processing unit may also modify motivational content included in a workout file, thereby creating modified motivational content. For example, if a video of terrain to be traversed by a user is included in a workout file, the playback speed of that video or the horizon line may be modified when a sizing restriction is applied to a control command. Modifying the motivational content may be necessary so that the motivational content remains synchronized with or accurate with the restricted control command subset.

Other motivational content may be modified as well. For example, the timing of audible encouragement may be altered so that it is provided at a specific part of a workout (for example, just prior to a particularly intense part of a workout), a visual display of a workout profile, projected biological metrics, etc. In addition, other data or control commands within a workout file may also be modified. For example, fan speed may be modified to correspond to a restricted control command subset.

The invention claimed is:
1. An exercise device comprising:
   a first moveable member having a first operating parameter selectively adjustable within a first range;
   a second moveable member having a second operating parameter selectively adjustable within a second range;

a first actuator configured to selectively adjust the first operating parameter of the first moveable member within the first range;

a second actuator configured to selectively adjust the second operating parameter of the second moveable member within the second range;

a receiving port that receives a workout file, the workout file having multiple actuator control commands including a first actuator control command and a second actuator control command, the first actuator control command compatible with the first actuator, the second actuator control command compatible both with the second actuator and with a third actuator of a third moveable member of a different type of exercise device, the second actuator control command incompatible with the first actuator, the first actuator control command incompatible both with the second actuator and the third actuator; and a processing unit that is in communication with the first actuator and the second actuator and the receiving port, the processing unit including instructions, that when executed by the processing unit, cause the processing unit to scan the workout file received by the receiving port, to identify and select actuator control commands from the workout file that are compatible with the first actuator and with the second actuator.

2. The exercise device of claim 1, wherein the processing unit is further configured to analyze the first actuator control command and automatically apply a sizing restriction to the first actuator control command to create a restricted first actuator control command when the first actuator control command is outside a range of the e first operating parameter of the first moveable member.

3. The exercise device of claim 2, wherein the workout file further comprises motivational content.

4. The exercise device of claim 3, wherein the motivational content is synchronized with or reflective of the multiple actuator control commands within the workout file.

5. The exercise device of claim 4, wherein reference data enables the processing unit to modify the motivational content.

6. The exercise device of claim 5, wherein the motivational content includes a video of terrain to be traversed during performance of an exercise and wherein the processing unit modifies a horizon line on the video so that the horizon line on the video remains synchronized with the restricted first actuator control command.

7. The exercise device of claim 5, wherein the motivational content includes a video of terrain to be traversed during performance of an exercise and wherein the processing unit modifies playback speed of the video so that the playback speed of the video remains synchronized with the restricted first actuator control command.

8. The exercise device of claim 5, wherein the motivational content includes a graphical representation of a workout file profile and wherein the processing unit modifies the graphical representation of the workout file profile so that the workout file profile remains reflective of the restricted first actuator control command.

9. The exercise device of claim 5, wherein the motivational content includes projected biological metrics and wherein the processing unit modifies the projected biological metrics so that the projected biological metrics remain reflective of the restricted first actuator control command.

10. The exercise device of claim 2, wherein the sizing restriction applied by the processing unit comprises a scaling sizing restriction.

11. The exercise device of claim 2, wherein the sizing restriction applied by the processing unit comprises a capping sizing restriction.

12. The exercise device of claim 1, wherein the workout file is a universal workout file and includes actuator control commands for at least two different types of exercise devices.

13. The exercise device of claim 12, wherein the at least two different types of exercise devices are selected from the group consisting of treadmills, elliptical machines, and exercise bikes.

14. The exercise device of claim 1, wherein the first actuator control command is configured to be modified by the processing unit based on user input.

15. The exercise device of claim 1, wherein the receiving port is a memory device drive.

16. The exercise device of claim 1, wherein:

the second actuator of the exercise device is the same type of actuator as the third actuator of the different type of exercise device; and the second moveable member of the exercise device is a different type of moveable member than the third moveable member of the different type of exercise device.

17. An exercise system comprising:

a remote computer that makes available a workout file that includes multiple actuator control commands including a first actuator control command and a second actuator control command;

a first exercise device having a first processing unit, a first operating parameter that is selectively adjustable within a first range, and a second operating parameter that is selectively adjustable within a second range, wherein the first processing unit includes instructions, that when executed by the first processing unit, cause the first processing unit to scan the workout file to identify and select actuator control commands from the workout file that are compatible with a first actuator of the first exercise device and with a second actuator of the first exercise device; and a second exercise device of a different type having a second processing unit and a third operating parameter that is selectively adjustable within a third range, wherein the second processing unit includes instructions, that when executed by the second processing unit, cause the second processing unit to scan the workout file to identify and select actuator control commands from the workout file that are compatible with a third actuator of the second exercise device;

wherein the first actuator control command is compatible with the first actuator, the second actuator control command is compatible with both the second actuator and the third actuator, the first actuator control command is incompatible with both the second actuator and the third actuator, and the second actuator control command is incompatible with the first actuator.

18. The exercise system of claim 17, wherein the first processing unit automatically applies a sizing restriction to the first actuator control command to create a restricted first actuator control command when the first actuator control command is outside the first range of the first operating parameter; and wherein the second processing unit automatically applies a sizing restriction to the second actuator control command to create a second restricted second actuator control command when the second actuator control command is outside the third range of the third operating parameter.

19. A method for controlling one or more exercise devices, the method comprising:
   providing a workout file having multiple actuator control commands including a first actuator control command and a second actuator control command;
   providing a first exercise device having a processing unit, a first moveable member having a first operating parameter selectively adjustable within a first range, a first actuator configured to selectively adjust the first operating parameter of the first moveable member within the first range, a second moveable member having a second operating parameter selectively adjustable within a second range, and a second actuator configured to selectively adjust the second operating parameter of the second moveable member within the second range;
   identifying and selecting, with the processing unit, the first actuator control command and the second actuator control command from the workout file as being compatible with the first actuator and with the second actuator, respectively; and
   adjusting the first moveable member based on the first actuator control command and adjusting the second moveable member based on the second actuator control command; wherein the first actuator control command is compatible with the first actuator, the second actuator control command is compatible with both the second actuator and a third actuator of a third moveable member of a second exercise device that is a different type of exercise device from the first exercise device, the first actuator control command is incompatible with both the second actuator and the third actuator, and the second actuator control command is incompatible with the first actuator.

20. The method of claim 19, further comprising:
   adjusting an operating parameter of the third moveable member based on the second actuator control command.

* * * * *